US009291628B2

(12) United States Patent
Leonard et al.

(10) Patent No.: US 9,291,628 B2
(45) Date of Patent: Mar. 22, 2016

(54) DIRECT CLONE ANALYSIS AND SELECTION TECHNOLOGY

(75) Inventors: Paul Leonard, Ashbourne (IE); Ivan Dimov, Puerto Montt (CL); Richard O'Kennedy, Rathgar (IE); Valerie Fitzgerald, Ashbourne (IE)

(73) Assignee: Dublin City University, Glasnevin, Dublin (IE)

( * ) Notice: Subject to any disclaimer, the term of this patent is extended or adjusted under 35 U.S.C. 154(b) by 0 days.

(21) Appl. No.: 13/809,833

(22) PCT Filed: Jul. 13, 2011

(86) PCT No.: PCT/EP2011/062015
§ 371 (c)(1),
(2), (4) Date: Apr. 1, 2013

(87) PCT Pub. No.: WO2012/007537
PCT Pub. Date: Jan. 19, 2012

(65) Prior Publication Data
US 2013/0190206 A1    Jul. 25, 2013

Related U.S. Application Data

(60) Provisional application No. 61/363,715, filed on Jul. 13, 2010.

(30) Foreign Application Priority Data

Jul. 13, 2010 (EP) .................................... 10007198

(51) Int. Cl.
G01N 33/53   (2006.01)
G01N 33/68   (2006.01)
B01L 3/00    (2006.01)

(52) U.S. Cl.
CPC ............ *G01N 33/68* (2013.01); *B01L 3/50857* (2013.01); *G01N 33/53* (2013.01); *G01N 33/5302* (2013.01); *B01L 2300/0636* (2013.01); *B01L 2300/0819* (2013.01)

(58) Field of Classification Search
None
See application file for complete search history.

(56) References Cited

U.S. PATENT DOCUMENTS

| 6,129,896 A  | 10/2000 | Noonan et al.  |
| 6,542,691 B2 | 4/2003  | Mizuno et al.  |
| 7,169,577 B2 | 1/2007  | Wang et al.    |
| 7,179,638 B2 | 2/2007  | Anderson et al.|

(Continued)

FOREIGN PATENT DOCUMENTS

WO    WO 2007035633 A2 *   3/2007

OTHER PUBLICATIONS

International Preliminary Report on Patentability dated Jan. 15, 2013 for International Application No. PCT/EP2011/062015, filed Jul. 13, 2011.

*Primary Examiner* — Tracy Vivlemore
*Assistant Examiner* — Karen S Weiler
(74) *Attorney, Agent, or Firm* — Dickstein Shapiro LLP

(57) ABSTRACT

The present invention describes a spatial addressing technique that uses a very high-density micro-pore array for high-throughput screening of biological interactions. The therapeutic, diagnostic and drug-discovery implications of being able to identify, select and characterize specific protein-protein, protein-DNA and/or protein-carbohydrate interactions from heterogeneous populations of millions (to billions) of cells is discussed. Importantly, this technique possesses the screening and selection capacity of current display-based screening systems (i.e., millions-billions) but with greater efficiency and shorter time.

12 Claims, 30 Drawing Sheets

(56) References Cited

U.S. PATENT DOCUMENTS

| | | |
|---|---|---|
| 7,280,727 B1 | 10/2007 | Barbedette et al. |
| 2001/0012537 A1 | 8/2001 | Anderson et al. |
| 2003/0044855 A1* | 3/2003 | Anderson et al. ............... 435/7.9 |
| 2003/0044968 A1* | 3/2003 | Lafferty et al. ............ 435/287.2 |

* cited by examiner

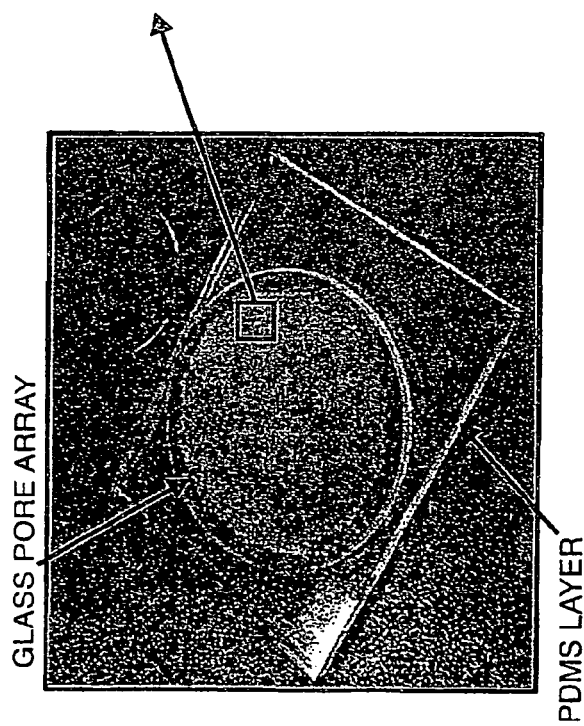
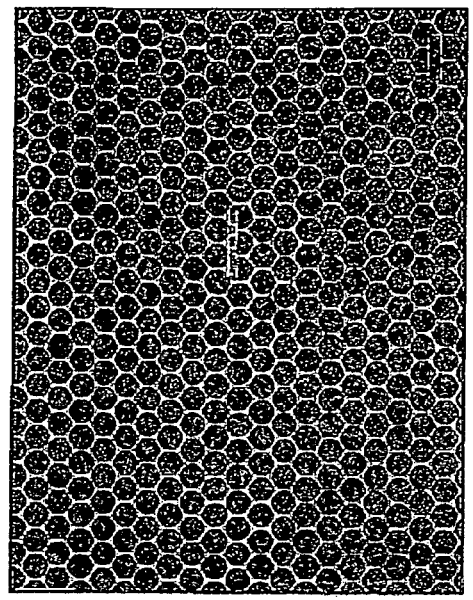
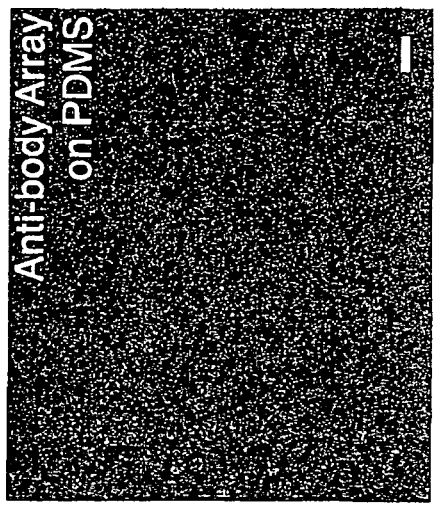
FIG. 7A
FIG. 7B
FIG. 7C

NEAT

CLUMPS OF *E.COLI* INSIDE PORE

1/100 OF NEAT

PROBABLY SINGLE *E.COLI* INSIDE PORE

| GAIN 81 READ AT TIME 0 | MEDIA | 1 IN 10,000 | 1 IN 1,000 | 1 IN 100 | 1 IN 10 | NEAT | |
|---|---|---|---|---|---|---|---|
| <> | 1 | 2 | 3 | 4 | 5 | 6 | |
| A | 3925 | 3195 | 3471 | 3335 | 6871 | 40411 | GFP CELLS |
| B | 3875 | 3477 | 2661 | 2619 | 4132 | 42921 | GFP CELLS |
| C | 11 | 9 | 10 | 10 | 10 | 9 | BLANK WELLS |

| GAIN 81 READ AT 10 AM | MEDIA | 1 IN 10,000 | 1 IN 1,000 | 1 IN 100 | 1 IN 10 | NEAT | |
|---|---|---|---|---|---|---|---|
| <> | 1 | 2 | 3 | 4 | 5 | 6 | |
| A | 3325 | 5871 | 6828 | 11200 | 35286 | 56425 | GFP CELLS |
| B | 3404 | 5251 | 5629 | 13668 | OVER | OVER | GFP CELLS |
| C | 9 | 10 | 9 | 9 | 9 | 10 | BLANK CELLS |

FIG. 12

BLACK LASER PRINTER INK PRINTED ON TRANSPARENT PLASTIC

LASER HOLE BURNT INTO THE PLASTIC (100μm IN DIAMETER)

RED FOOD COLORANT FILLED PORES

AREA EMPTIED OF RED FOOD COLORANT BY LASER HOLE AIR PRESSURE (~300μm IN DIAMETER)

DIRECT CLONE ANALYSIS AND SELECTION TECHNOLOGY

CROSS-REFERENCE TO RELATED APPLICATIONS

This application is the U.S. national phase application filed under 35 U.S.C, §371 claiming benefit to International Patent Application No. PCT/EP2011/062015, filed on Jul. 13, 2011, which claims priority to European Application No. 10007198.4, filed Jul. 13, 2010, and is entitled to priority under 35 U.S.C, §119(e) to U.S. Provisional Patent Application No. 61/363,715, filed on Jul. 13, 2010, each of which application is hereby incorporated herein by reference in its entirety.

FIELD OF INVENTION

The invention is related to high throughput assay screening technology platforms. The platforms described herein can be used to discover, characterize and select specific interaction pairs from a heterogeneous population of millions or even billions of cells (i.e., for example, bacterial clones). For example, a very high-density micro-pore array is screened and, after screening, cells are collected from selected micro-pores. Optionally, the micro-pore array is reversibly attached to a solid substrate, wherein, after screening, the array is removed from the substrate for cell collection from selected micro-pores.

BACKGROUND

There are many technologies used commercially to select and screen compounds from large diverse protein libraries. These technologies include Phage Display, Ribosome Display, Yeast Display and Bacterial Display, in vitro compartmentalization, microengraving and spatial addressing. Lin et al., (2002). "Screening and Selection Methods for Large-Scale Analysis of Protein Function" *Angew. Chem. Int. Ed.,* 41:4402-4425 (2002); Willats et al., (2002) "Phage display: practicalities and prospects" *Plant Molecular Biology* 50; 837-854; and Sergeeva et. al., (2006) "Display technologies: Applications for the discovery of drug and gene delivery agents" *Advanced Drug Delivery Reviews* 58:1622-1654.

The advent of phage display technology and alternative display systems allowed antibody screening by linking them to bacterial viruses and provided recovery of the antibody genes post screening by infection into bacteria. The technology has been widely commercialized. Due mainly to the costs of these licenses and the competitive nature of the lucrative antibody-based therapeutic market, alternative display technologies have also been developed. For example, microengraving microwells may capture single cells. Nonetheless, the current techniques lack the necessary robustness and selectivity to provide large-scale diagnostic and therapeutic screening.

A single-cell analysis in quantitative biology has been explored by various methods. Levsky et al., *Science* 297:836-840 2002; Hong et al., *Nat. Biotechnol.* 22:435-439 2004; Kurimoto et al., *Nucleic Acids Res.* 34:e42 (2006); Huang et al., *Science* 315:81-84 (2007); and Newman et al., *Nature* 441:840-846 (2006). However, these newly emerging methods have not been fully applied in the biological sciences as of yet. One of the reasons for this is the fact that these methods are too sophisticated and integrated to be used without appropriate investment of time, money, and labor. Thus, there is a strong need to simplify and make these methods more user-friendly for realization of quantitative biology at the single-cell level.

What is needed in the art is a better system for direct selection and characterization for processing cells and/or interacting biochemical pairs and selectively isolating each single cell.

SUMMARY

The invention is related to high throughput assay screening technology platforms. The platforms described herein can be used to discover, characterize and select specific interaction pairs from a heterogeneous population of millions or even billions of cells (i.e., for example, bacterial clones). For example, a very high-density micro-pore array is screened and, after screening, cells are collected from selected micro-pores. Optionally, the micro-pore array is reversibly attached to a solid substrate, wherein, after screening, the array is removed from the substrate for cell collection from selected micro-pores.

In one embodiment, the present invention contemplates a device comprising an array of micro-pores, the micro-pore array being reversibly attached to a solid substrate, wherein at least one binding partner is attached to said solid substrate, and wherein the internal diameter of the micro-pores ranges between approximately 1.0 micrometers and 500 micrometers. Optionally, the micro-pores are not coated with at least one binding partner. Optionally, said each of said micro-pores has an internal diameter in the range between approximately 1.0 micrometers and 300 micrometers; optionally between approximately 1.0 micrometers and 100 micrometers; further optionally between approximately 1.0 micrometers and 75 micrometers; still further optionally between approximately 1.0 micrometers and 50 micrometers, still further optionally between approximately 5.0 micrometers and 50 micrometers. Optionally, there are approximately 300 to 1,150,000 of said micro-pores, per $cm^2$ of said array. In one embodiment, the device further comprises a polymeric film, wherein said array is covered by said polymeric film, wherein said polymeric film further comprises at least one hole and wherein said hole is positioned over at least one of said micro-pores. In one embodiment, the device further comprises a pressure source configured proximal to said at least one hole. Such a pressure source may comprise a pressurized fluid source. Optionally, said micro-pores further comprise at least one biological cell; further optionally, said at least one biological cell is a transformed microbial or mammalian cell that, optionally, secretes a recombinant antibody. In one embodiment, the micro-pores range between approximately 10 micrometers and 1 millimeter long. In one embodiment, the micro-pores range between approximately 10 micrometers and 1 centimeter long. In one embodiment, the micro-pores range between approximately 10 micrometers and 10 millimeter long. In one embodiment, the micro-pores range between approximately 10 micrometers and 100 millimeter long. In one embodiment, the micro-pores range between approximately 0.5 millimeter and 1 meter long. In one embodiment, the micro-pores are approximately 1 millimeter long. In one embodiment, the micro-pores are approximately 10 millimeters long. In one embodiment, the micro-pores are approximately 1 centimeter long. In one embodiment, the micro-pores are approximately 1 meter long. In one embodiment, each of the micro-pores defines an opening that is approximately 5 micrometers in diameter. In one embodiment, each of the micro-pores defines an opening that is approximately 10 micrometers in diameter. In one embodiment, each of the micro-pores defines an opening that is approximately 15 micrometers in diameter. In one embodiment, each of the micro-pores defines an opening that is approximately 25 micrometers in diameter. In one embodiment, each of the micro-pores defines an opening that is approximately 50 micrometers in diameter. In one embodiment, each of the micro-pores defines an opening that is approximately 100 micrometers in diameter. In one embodiment, each of the micro-pores defines an opening that is approximately 300 micrometers in diameter. In one embodiment, each of the micro-pores defines an opening that is approximately 500 micrometers in diameter.

In one embodiment, the present invention contemplates a device comprising a plurality of longitudinally fused fibers reversibly bonded to a single degassed solid substrate that is gas permeable, wherein the solid substrate is attached to at least one binding partner. In one embodiment, the fibers comprise glass capillary fibers. In one embodiment, the fused capillary fibers are not attached to at least one binding partner. In one embodiment, the fused capillary fibers are attached to at least one binding partner. In one embodiment, the device comprises a micro-pore testbed array. In one embodiment, the fused capillary fibers range between approximately 10 micrometers and 1 millimeter long. In one embodiment, the fused capillary fibers range between approximately 0.5 millimeter and 1 meter long. In one embodiment, the fused capillary fibers are approximately 1 millimeter long. In one embodiment, the fused capillary fibers are approximately 10 millimeters long. In one embodiment, the fused capillary fibers are approximately 1 centimeter long. In one embodiment, the fused capillary fibers are approximately 1 meter long. In one embodiment, each of the fused capillary fibers range between approximately 5 micrometers and 500 micrometers in diameter. In one embodiment, each of the fused capillary fibers range between approximately 2 micrometers and 500 micrometers in diameter; or between approximately 1.0 micrometers and 500 micrometers, optionally between approximately 1.0 micrometers and 300 micrometers; further optionally between approximately 1.0 micrometers and 100 micrometers; further optionally between approximately 1.0 micrometers and 75 micrometers; still further optionally between approximately 1.0 micrometers and 50 micrometers, still further optionally, between approximately 5.0 micrometers and 50 micrometers. In one embodiment, each of the fused capillary fibers is approximately 5 micrometers in diameter. In one embodiment, each of the fused capillary fibers is approximately 10 micrometers in diameter. In one embodiment, each of the fused capillary fibers is approximately 15 micrometers in diameter. In one embodiment, each of the fused capillary fibers is approximately 25 micrometers in diameter. In one embodiment, each of the fused capillary fibers is approximately 50 micrometers in diameter. In one embodiment, each of the fused capillary fibers is approximately 100 micrometers in diameter. In one embodiment, each of the fused capillary fibers is approximately 300 micrometers in diameter. In one embodiment, each of the fused capillary fibers is approximately 500 micrometers in diameter. In one embodiment, the plurality of fused capillary fibers ranges between approximately 300,000 and 5,000,000,000 capillary fibers, each fiber defining a well. In one embodiment, there are between approximately 300 to 1,150,000 of said fused fibers, per $cm^2$ of the array. In one embodiment, there are between approximately 300 of said fused fibers, per $cm^2$ of the array. In one embodiment, there are between approximately 1,000 to 1,150,000 of said fused fibers, per $cm^2$ of the array. In one embodiment, there are between approximately 10,000 of said fused fibers, per $cm^2$ of the array. In one embodiment, there are between approximately 50,000 of said fused fibers, per $cm^2$ of the array. In one embodiment, there are between approximately 500,000 of said fused fibers, per $cm^2$ of the array. In one embodiment, there are between approximately 1,150,000 of said fused fibers, per $cm^2$ of the array. In one embodiment, the device further comprises at least one biological cell in each of the wells. In one embodiment, the plurality of fused capillary fibers is approximately 300,000 fused capillary fibers. In one embodiment, the plurality of fused capillary fibers is approximately 500,000 fused capillary fibers. In one embodiment, the plurality of fused capillary fibers is approximately 1,000,000 fused capillary fibers. In one embodiment, the plurality of fused capillary fibers is approximately 5,000,000 fused capillary fibers. In one embodiment, the plurality of fused capillary fibers is approximately 1,000,000,000 fused capillary fibers. In one embodiment, the plurality of fused capillary fibers is approximately 5,000,000,000 fused capillary fibers. In one embodiment, the solid substrate comprises silicon. In one embodiment, the solid substrate is polymer. In one embodiment, the gas permeable material comprises poly (dimethylsiloxane) (PDMS). In one embodiment, the solid substrate comprises glass. In one embodiment, the solid substrate comprises quartz. In one embodiment, the solid substrate is degassed and the solid substrate is a gas permeable material. In another embodiment, the solid substrate is coated with an agent such as vinyl silane or aminopropyltriethoxy silane (APTES), which may be useful to allow attachment of the solid substrate (for example, glass) to the at least one binding partner.

In one embodiment, the present invention contemplates a device comprising a plurality of longitudinally fused fibers and a polymeric film, wherein the fused fibers are bonded to the polymeric film. In one embodiment, the fused fibers comprise fused glass capillary fibers.

In one embodiment, the polymeric film further comprises at least one hole, wherein the hole is positioned over at least one of the capillary fibers. In one embodiment, the device further comprises a pressure source comprising a nozzle, wherein the nozzle is configured to fit within the circumference of the at least one hole. In one embodiment, the capillary fiber further comprises at least one biological cell. In one embodiment, the at least one biological cell is a transformed biological cell. In one embodiment, the biological cell comprises a microbial, fungal, mammalian, insect or animal cell. In one embodiment, the microbial cell comprises a bacterial cell. In one embodiment, the bacterial cell comprises an *E. coli* cell. In one embodiment, the cell comprises a fungal cell. In one embodiment, the cell comprises a mammalian cell. In one embodiment, the microbial cell is a transformed microbial cell. In one embodiment, the cell comprises a transformed fungal cell. In one embodiment, the cell comprises a transformed mammalian cell. In one embodiment, the transformed microbial cell secretes a recombinant antibody. In one embodiment, the transformed microbial cell secretes a recombinant protein and/or peptide. In one embodiment, the biological cell is an animal cell In one embodiment, the animal cell comprises a rare biochemical compound. In one embodiment, the rare biochemical compound is selected from the group comprising a protein, a peptide, a hormone, a nucleic acid, a carbohydrate.

In one embodiment, the fused capillary fibers range between approximately 0.5 millimeter and 1 meter long. In one embodiment, each of the fused capillary fibers range between approximately 5 micrometers and 500 micrometers in diameter. In one embodiment, the hole ranges between approximately 5 micrometers and 500 micrometers in diameter. In one embodiment, the plurality of fused capillary fibers ranges between approximately 300,000 and 5,000,000,000 capillary fibers. In one embodiment, the polymeric film is selected from the group including but not limited to polylactide, polygalactide, polypropylene, polybutylene, polycaprone, polyester and any combination thereof.

In one embodiment, the present invention contemplates a method for identifying a sub-population of cells from a heterologous population of biological cells, the method comprising: a) providing: i) an array of micro-pores, wherein the internal diameter of micro-pores ranges between approximately 1.0 micrometers and 500 micrometers; ii) said heterologous population of cells; iii) at least one binding partner; b) contacting said array with said heterologous population of cells and said at least one binding partner such that a sub-population comprising at least one of said biological cells settles into at least one of said micro-pores of said array; c) incubating said array under conditions to promote the secretion of molecules from said biological cells; and d) detecting desired secreted molecules in at least one of said micro-pores of said array, thereby identifying said sub-population of cells. In one embodiment, the providing step comprises providing an array of micro-pores not being coated with at least one binding partner. In one embodiment, the detecting step comprises detecting the desired secreted molecules in association with at least one binding partner.

In one embodiment, the present invention contemplates a method comprising, a) providing: i) a degassed solid substrate comprising at least one binding partner, wherein the solid substrate is gas permeable and is attached to a plurality of longitudinally fused fibers thereby creating a micro-pore testbed array; ii) a plurality of biological cells (the cells being in solution or suspension); iii) optionally a polymeric film comprising at least one hole, such that the film is configured to bond to the fused capillary fibers; and b) contacting the micro-pore testbed array with the solution such that at least one of the plurality of biological cells settles into at least one of the fused capillary fibers; c) optionally bonding the polymeric film to the fused capillary fibers such that the hole is positioned over at least one of the capillary fibers; d) removing the fused capillary fiber-polymeric film array from the solid substrate; and e) collecting the at least one biological cell from the at least one fused capillary fiber wherein, optionally, the nozzle of the pressure source is placed over the at least one capillary fiber. In one embodiment, the solid substrate is reversibly attached to the plurality of longitudinally fused fibers. In one embodiment, the method further comprises providing a pressure source configured proximal to said at least one hole. In one embodiment, the pressure source comprises a nozzle. In one embodiment, the method further comprises collecting a sub-population, such as the plurality of biological cells from said at least one fused fiber. In one embodiment, the fibers comprise glass capillary fibers. In one embodiment, the fused capillary fibers do not comprise at least one binding partner. In one embodiment, the plurality of biological cells release and/or secrete at least one biological compound having affinity for the at least one binding partner. In one embodiment, the at least one binding partner may be selected from the group comprising antigens, antibodies, proteins, peptides, nucleic acids, deoxyribonucleic acids, ribonucleic acids, lipids, and/or carbohydrates. In one embodiment, the method further comprising binding the at least one binding partner to the at least one biological compound, wherein a binding partner/biological compound complex is formed on the solid substrate. In one embodiment, the method further comprises detecting the binding partner/biological compound complex. In one embodiment, the detecting comprises a labeled reagent having affinity for the binding/partner/biological compound complex. In one embodiment, the collecting comprises cultivating the at least one biological cell.

In one embodiment, the present invention contemplates a method comprising: a) providing: i) a plurality of longitudinally fused fibers reversibly attached to a solid support, each fiber defining a well, the solid surface comprising at least one type of binding partner and serving as the bottom of the well, the wells collectively comprising an array; ii) a heterologous population of biological cells (in solution or suspension); b) contacting said array with said solution such that at least one of said cells settles into at least one of said wells of said array; c) incubating said array under conditions to promote the secretion of molecules from said cells; d) removing said plurality of fused fibers from said solid support; and e) detecting whether secreted molecules bound said binding partner on said solid support. In one embodiment, the fibers comprise glass capillaries.

In one embodiment, the method of the present invention contemplates the concentration of the suspension of heterologous population of cells and the dimensions of the array are arranged such that 1-1000 cells, optionally, 1-500 cells, further optionally, 1-100 cells, still further optionally 1-10 cells, still further optionally, 1-5 cells, are distributed into at least one of said micro-pores of the array.

In one embodiment, the present invention contemplates a kit comprising: a first container comprising an array of micro-pores, wherein the internal diameter of micro-pores range between approximately 1.0 micrometers and 500 micrometers; and a second container comprising at least one binding partner. In one embodiment the second container comprises a solid substrate comprising said at least one binding partner, the solid substrate being capable of reversible attachment to the array of micro-pores.

In one embodiment, the present invention contemplates a kit comprising a first container comprising a micro-pore array comprising a plurality of fused capillary fibers that are not coated with at least one binding partner. In one embodiment, the kit further comprises a second container comprising a degassed solid substrate comprising at least one binding partner. In one embodiment, the kit further comprises a third container comprising a plurality of labeled reagents capable of detecting a variety of binding partner-biological compound complexes. In one embodiment, the kit further comprises a fourth container comprising a solution comprising a biological cell comprising a recombinant protein. In one embodiment, the kit further comprises instructional materials containing directions (i.e., protocols) providing for the use of the micro-pore array in the detection of various biological compounds that are secreted from a biological cell.

In one embodiment, the present invention contemplates use of an array of micro-pores for identifying a selected sub-population of cells from a heterologous population of biological cells, the use comprising: a) providing: i) an array of micro-pores, the diameter of micro-pores ranging between approximately 2.0 micrometers and 500 micrometers in diameter; ii) a heterologous population of cells; b) contacting said array with said solution such that the sub-population settles into at least one of said micro-pores of said array; c) incubating said array under conditions to promote the secretion of molecules from said cells; and d) detecting desired secreted molecules in at least one of said micro-pores of said array. In one embodiment, the array is not coated with at least one binding partner. In one embodiment, the concentration of the suspension of heterologous population of cells and the dimensions of the array are arranged such that 1-1000 cells, optionally, 1-500 cells, further optionally, 1-100 cells, still further optionally 1-10 cells, still further optionally, 1-5 cells, are distributed into at least one of said micro-pores of the array.

DEFINITIONS

The terms "binding partner", "ligand" or "receptor" as used herein, may be any of a large number of different molecules, or aggregates, and the terms are used interchangeably. Each binding partner may be immobilized on a solid substrate and binds to an analyte being detected. Alternatively, each binding partner may not be immobilized on either the solid substrate or on the micro-pores of the array. Proteins, polypeptides, peptides, nucleic acids (nucleotides, oligonucleotides and polynucleotides), antibodies, ligands, saccharides, polysaccharides, receptors, antibiotics, test compounds (particularly those produced by combinatorial chemistry), may each be a binding partner. One non-limiting example of binding partners are antibodies and antigens.

The term "biological cell" as used herein, refers to any cell from an organism, including, but not limited to, microbial, fungal (for example, yeast) or animal, such as mammalian or insect, cells.

The terms "biological compound" or "analyte" as used herein, refers to any compound released (i.e., for example, secreted) by a biological cell. Such a compound or analyte may be an amino acid sequence, a nucleic acid sequence, a hormone or any other biologically synthesized molecule. The biological compounds or analyte may attach to a binding partner, wherein they are detected as a binding partner/compound or binding partner/analyte complex.

The term "longitudinally fused fiber" as used herein, refers to at least two fibers that are attached along their respective longitudinal axis such that they become a single unit. Such attachment may be facilitated by exposure to heat, chemicals, or adhesives. Such fibers are generally hollow and may be comprised of glass capillary fibers.

The term "reversibly bonded" or 'reversibly attached" as used herein, refers to any attachment between to device components that provides a watertight seal while bonded, but may be separated without the use of chemicals or heat. For example, the device components may be sepearated by hand.

The term "degassed solid substrate" as used herein, refers to any material capable of supporting the reversible bonding of a micro-pore array, wherein the material has a decreased content of dissolved gases. For example, a degassed solid substrate may comprise PDMS. However, it will be appreciated that solid substrates that are not degassed are also capable of supporting the reversible bonding of a micro-pore array.

The term "micro-pore testbed array" as used herein, refers to any assembly comprising a micro-pore array reversibly bonded to a solid substrate.

The term "cultivating" or "culturing" as used herein, refers to any method wherein a cell or plurality of cells in incubated in a medium that supports cell proliferation such that the number of living cells increase.

The term "polymeric film" as used herein, refers to any sheet of material capable of forming a seal with the open ends of a micro-pore microarray and susceptible to penetration by a low energy laser, thereby creating a hole (i.e., for example, between 5-500 μm in diameter).

The term "rare biochemical compound" as used herein, refers to any biochemical compound that is produced in less than between approximately 20%-0.001% of native biological cells.

The term "pressure source" as used herein, refers to any device capable of generating a mechanical, liquid or gaseous stream at a variety of pressures, both positive and negative. Preferably, the diameter of the liquid or gaseous stream may be varied by using an adjustable nozzle. For example, one pressure source may comprise an air pressure source. The pressure source may be configured proximal to at least one of the fused fibers, wherein the pressure source contents may be expelled thereby removing the contents of the fused fibers or micro-pores. Optionally, a fused fiber or micro-pore may be covered with a polymeric film comprising a hole in-line with the fused fibers or micro-pores, wherein the hole may have a diameter greater than, equal to or smaller than the fused fiber diameter or the inner diameter of the micro-pore.

The term "secrete" as used herein, refers to any release of a biological compound or analyte from a biological cell in to the surrounding medium. Such secretion may be the result of active transport, passive diffusion or cell lysis.

The term "bind" or "attach" as used herein, includes any physical attachment or close association, which may be permanent or temporary. Generally, an interaction of hydrogen bonding, hydrophobic forces, van der Waals forces, covalent and ionic bonding etc., facilitates physical attachment between the molecule of interest and the analyte being measured. The "binding" interaction may be brief as in the situation where binding causes a chemical reaction to occur. That is typical when the binding component is an enzyme and the analyte is a substrate for the enzyme. Reactions resulting from contact between the binding agent and the analyte are also within the definition of binding for the purposes of the present invention.

The term "fiber" as used herein, includes both filaments and hollow capillary structures. Pluralities, typically a large number, of fibers are bound (i.e., for example, fused) adjacent to each other in ribbons or bundles to form a "block." A fiber block may constitute a portion of the actual bundle being used. A cross-section of the fibers may be of any shape, such as round, triangular, square, rectangular or polygonal. The fibers may be of material such as glass, metal, ceramic or plastic.

The term "sintering" as used herein, refers to the fusion of the surfaces of the fibers without actually melting the whole fiber. Sintering may be chemical or thermal and may even involve a self-adhesive component that may be activatable.

The terms "arrays" and "microarrays" are used somewhat interchangeably differing only in general size. The instant invention involves the same methods for making and using either. Each array typically contains many cells (typically 100-1,000,000+) wherein each cell is at a known location and contains a specific component of interest. Each array therefore contains numerous different components of interest.

In a related aspect, "device" is used to describe both arrays and microarrays, where the array or microarray may comprise other defined components including surfaces and points of contact between reagents.

Further, "substrate" is also a term used to describe surfaces as well as solid phases which may comprise the array, microarray or device. In some cases, the substrate is solid and may comprise PDMS.

The term "protein" as used herein, refers to any of numerous naturally occurring extremely complex substances (as an enzyme or antibody) that consist of amino acid residues joined by peptide bonds, contain the elements carbon, hydrogen, nitrogen, oxygen, usually sulfur. In general, a protein comprises amino acids having an order of magnitude within the hundreds.

The term "peptide" as used herein, refers to any of various amides that are derived from two or more amino acids by combination of the amino group of one acid with the carboxyl group of another and are usually obtained by partial hydrolysis of proteins. In general, a peptide comprises amino acids having an order of magnitude with the tens.

The term, "purified" or "isolated", as used herein, may refer to a peptide composition that has been subjected to treatment (i.e., for example, fractionation) to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the composition (i.e., for example, weight/weight and/or weight/volume). The term "purified to homogeneity" is used to include compositions that have been purified to 'apparent homogeneity" such that there is single protein species (i.e., for example, based upon SDS-PAGE or HPLC analysis). A purified composition is not intended to mean that some trace impurities may remain.

As used herein, the term "substantially purified" refers to molecules, either nucleic or amino acid sequences, that are removed from their natural environment, isolated or separated, and are at least 60% free, preferably 75% free, and more preferably 90% free from other components with which they are naturally associated. An "isolated polynucleotide" is therefore a substantially purified polynucleotide.

"Nucleic acid sequence" and "nucleotide sequence" as used herein refer to an oligonucleotide or polynucleotide, and fragments or portions thereof, and to DNA or RNA of genomic or synthetic origin which may be single- or double-stranded, and represent the sense or antisense strand.

The term "an isolated nucleic acid", as used herein, refers to any nucleic acid molecule that has been removed from its natural state (e.g., removed from a cell and is, in a preferred embodiment, free of other genomic nucleic acid).

The terms "amino acid sequence" and "polypeptide sequence" as used herein, are interchangeable and refer to a sequence of amino acids.

As used herein the term "portion" when in reference to a protein (as in "a portion of a given protein") refers to fragments of that protein. The fragments may range in size from four amino acid residues to the entire amino acid sequence minus one amino acid.

The term "portion" when used in reference to a nucleotide sequence refers to fragments of that nucleotide sequence. The fragments may range in size from 5 nucleotide residues to the entire nucleotide sequence minus one nucleic acid residue.

The term "antibody" refers to immunoglobulin evoked in a host by an immunogen (antigen) or the expression product of cloned human or animal immunoglobulin genes by semi-synthetic (modified post cloning by PCR) or fully synthetic techniques (made in vitro and diversified by PCR). It is desired that the antibody demonstrates specificity to epitopes contained in the immunogen. An antibody may also comprise antibody fragments such as single chain fragment variable (scFv), Fragment binding (Fab) and any other format of recombinant antibody fragment. The term "polyclonal antibody" refers to immunoglobulin produced from more than a single clone of plasma cells; in contrast "monoclonal antibody" refers to immunoglobulin produced from a single clone of plasma cells.

The terms "specific binding" or "specifically binding" when used in reference to the interaction of an antibody and a protein or peptide means that the interaction is dependent upon the presence of a particular structure (i.e., for example, an antigenic determinant or epitope) on a protein; in other words an antibody is recognizing and binding to a specific protein structure rather than to proteins in general. For example, if an antibody is specific for epitope "A", the presence of a protein containing epitope A (or free, unlabelled A) in a reaction containing labeled "A" and the antibody will reduce the amount of labeled A bound to the antibody.

The term "small organic molecule" as used herein, refers to any molecule of a size comparable to those organic molecules generally used in pharmaceuticals. The term excludes biological macromolecules (e.g., proteins, nucleic acids, etc.). Preferred small organic molecules range in size from approximately 10 Da up to about 5000 Da, more preferably up to 2000 Da, and most preferably up to about 1000 Da.

The term "sample" as used herein is used in its broadest sense and includes environmental and biological samples. Environmental samples include material from the environment such as soil and water. Biological samples may be animal, including, human, fluid (e.g., blood, plasma and serum), solid (e.g., stool), tissue, liquid foods (e.g., milk), and solid foods (e.g., vegetables). For example, a pulmonary sample may be collected by bronchoalveolar lavage (BAL), which comprises fluid and cells derived from lung tissues. A biological sample may comprise a cell, tissue extract, body fluid, chromosomes or extrachromosomal elements isolated from a cell, genomic DNA (in solution or bound to a solid support such as for Southern blot analysis), RNA (in solution or bound to a solid support such as for Northern blot analysis), cDNA (in solution or bound to a solid support) and the like.

The term "biologically active" refers to any molecule having structural, regulatory or biochemical functions. For example, biological activity may be determined, for example, by restoration of wild-type growth in cells lacking protein activity. Cells lacking protein activity may be produced by many methods (i.e., for example, point mutation and frameshift mutation). Complementation is achieved by transfecting cells that lack protein activity with an expression vector which expresses the protein, a derivative thereof, or a portion thereof.

The term "immunologically active" defines the capability of a natural, recombinant or synthetic peptide, or any oligopeptide thereof, to induce a specific immune response in appropriate animals or cells and/or to bind with specific antibodies.

The term "antigenic determinant" as used herein refers to that portion of a molecule that is recognized by a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "immunogen," "antigen," "immunogenic" and "antigenic" refer to any substance capable of generating antibodies when introduced into an animal. By definition, an immunogen must contain at least one epitope (the specific biochemical unit capable of causing an immune response), and generally contains many more. Proteins are most frequently used as immunogens, but lipid and nucleic acid moieties complexed with proteins may also act as immunogens. The latter complexes are often useful when smaller molecules with few epitopes do not stimulate a satisfactory immune response by themselves.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "C-A-G-T," is complementary to the sequence "G-T-C-A." Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands. This is of particular importance in amplification reactions, as well as detection methods that depend upon binding between nucleic acids.

The term "transfection" or "transfected" refers to the introduction of foreign DNA into a cell.

As used herein, the terms "nucleic acid molecule encoding", "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "label" or "detectable label" are used herein, to refer to any composition detectable by spectroscopic, photochemical, biochemical, immunochemical, electrical, optical or chemical means. Such labels include biotin for staining with labeled streptavidin conjugate, magnetic beads (e.g., Dynabeads®), fluorescent dyes (e.g., fluorescein, Texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include, but are not limited to, U.S. Pat. Nos. 3,817,837; 3,850,752; 3,939,350; 3,996,345; 4,277,437; 4,275,149; and 4,366,241 (all herein incorporated by reference). The labels contemplated in the present invention may be detected by many methods. For example, radiolabels may be detected using photographic film or scintillation counters, fluorescent markers may be detected using a photodetector to detect emitted light. Enzymatic labels are typically detected by providing the enzyme with a substrate and detecting, the reaction product produced by the action of the enzyme on the substrate, and calorimetric labels are detected by simply visualizing the colored label.

BRIEF DESCRIPTION OF THE FIGURES

FIG. 7 presents a representative glass micro-pore array. Scale bars are 20 μm. FIG. 7A presents a glass micro-pore array placed onto a degassed PDMS solid substrate (red box enlarged in FIG. 7B). FIG. 7B presents a microscopic image of the surface of the micro-pore array. FIG. 7C presents heterogeneous dye staining from different pores onto the PDMS surface.

FIG. 9 (FIGS. 9A and 9B) presents exemplary data of E. coli expressing GFP protein loaded at different densities (FIG. 9A—neat; FIG. 9B—1/100 of neat) inside the micropore test bed array after incubation for 1.5 hrs. All pores are ~10 μm diameter.

FIG. 12 presents exemplary data of cell growth and GFP expression in microtitre plates with varying cell loading densities.

FIG. 13A shows a 1/10 cell dilution: No single colonies were observed as the concentration of the cells removed from the array was very high. The cells grew well on the agar plates. FIG. 13B shows a 1/100 cell dilution: Single colonies were observed but were still hard to differentiate as the concentration of the cells removed from the array was very high. The cells grew well on the agar plates. FIG. 13C shows a 1/1000 cell dilution: A single colony was observed indicating a low concentration of viable cells in the area. Note: the procedure used to the remove the cells is crude and is not fully yet optimised. Experimental conclusions: The experiment successfully showed that the cells can grow and live in the array and can be recovered on agar plates for further characterisation. Due to the pore structure of the array of the present invention, the cells could be simply removed by air pressure (like blowing liquid from a straw) has been shown on a microscale for single pore analysis.

FIG. 28A illustrates one embodiment of a pore retrieval setup consisting of an array holder mounted on to a high precision XY stage, a stationary laser nozzle and nitrogen supply and a 384 well plate placed onto a second high precision XY stage.

DETAILED DESCRIPTION

Figure 1:
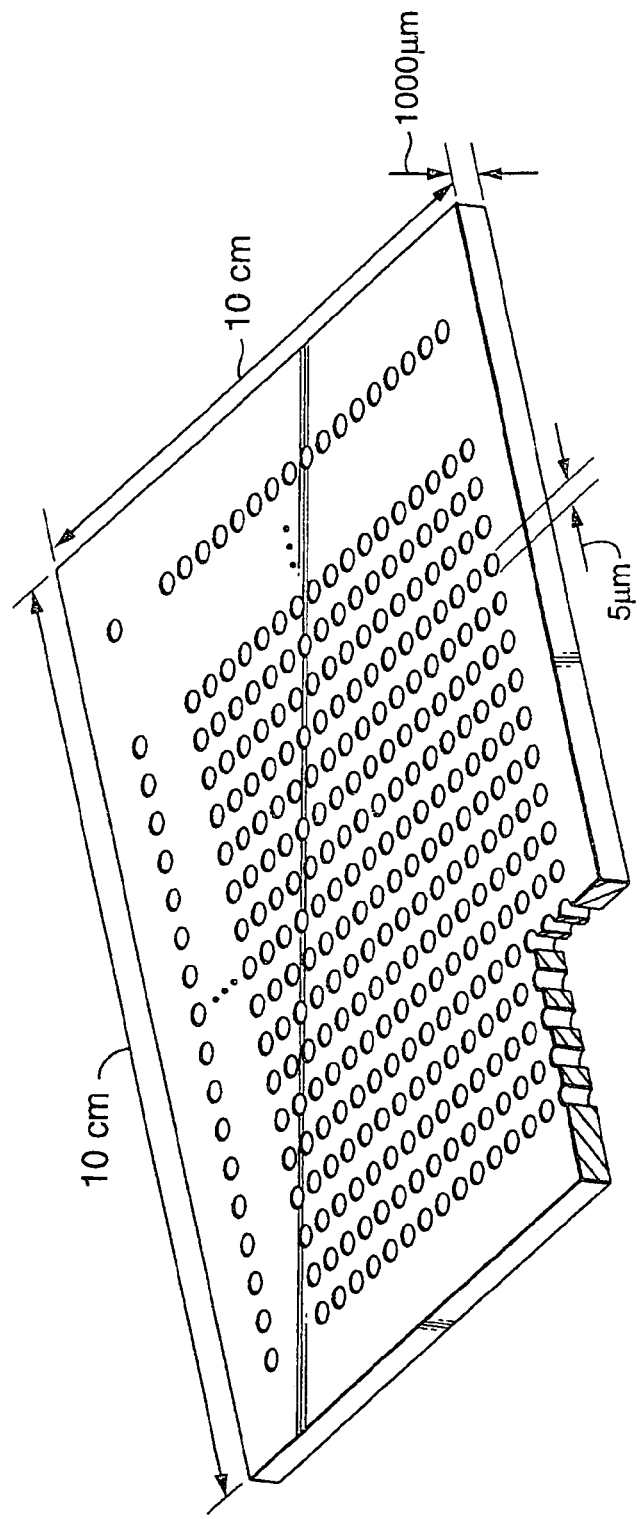
FIG. 1 illustrates one embodiment of a very high-density micro-pore array, having 5 nm pores.

The invention is related to high throughput assay screening technology platforms. The platforms described herein can be used to discover, characterize and select specific interaction pairs from a heterogeneous population of millions or even billions of cells (i.e., for example, bacterial clones). For example, a very high-density micro-pore array is screened and, after screening, cells are collected from selected micropores. Optionally, the micro-pore array is reversibly attached to a solid substrate, wherein after screening, the array is removed from the substrate for cell collection from selected micro-pores.

Using conventional technologies, biological libraries may be screened for components including but not limited to, antibodies, proteins, peptides, nucleic acids, deoxyribonucleic acids, and/or ribonucleic acids. These systems have a number of disadvantages, including the need to enrich for desired clones via repeat selection steps (including, for example "panning") that inherently result in the loss of potential binding candidates. It is also difficult to establish the precise origin of a positive signal using conventional technologies since they obtain mixed signals from heterogeneous populations that cannot be convoluted. Generally these techniques involve selection processes utilizing bacteriophages, ribosomes and specific cells, most of which are performed in vitro. Improvements in library screening have introduced the concept of spatial addressing in order to maintain identity of the screened components during the selection process. Such addressing can be based upon techniques including robotics, enzyme-linked immunosorbent assays, or cell-based assays. While spatial addressing can, for example, identify specific cellular clones to generate master stocks, these limitations do not facilitate high throughput screening techniques to selectively isolate and purify the identified clones for rapid application to disease diagnostics and therapeutics. Another disadvantage of the present screening assays are that they are usually limited to a cell number between approximately 50K-100K. In one embodiment, the invention provides a simple and direct technique for analyzing billions of antibody (or desired protein) secreting cells without the need for their display on viruses (phage display), ribosomes (ribosomal display) or cells (mammalian, bacterial or yeast display). In one embodiment, the invention provides a simple and direct technique for directly analyzing billions of antibody (or desired protein) secreting cells.

In one embodiment, the present invention contemplates methods that improve upon the above-mentioned selection processes by a technique comprising direct clone analysis and selection. In one embodiment, the direct clone analysis method utilizes native cells (i.e., not limited to cell culture stocks) that are cultivated in a micro-pore array, wherein the micro-pore array is, optionally, not coated with any biological ligands (i.e., for example, binding partners). In one embodiment, the native cells comprise fresh tissue cells. In one embodiment, the native cells comprise microbial cells. In one embodiment, the microbial cells are transformed with at least one recombinant protein. Further, the direct clone selection method analyzes all samples (i.e., for example, millions and/or billions) in parallel.

In one embodiment, the present invention contemplates a method for selecting billions of antibody producing biological cell clones using a micro-pore array (for example, aaporous glass array) (optionally, uncoated) that is, optionally, reversibly bonded to a solid substrate (i.e., for example, PDMS). In one embodiment, the micro-pores are filled with a solution (i.e., for example, a culture media) comprising the biological cell clones harboring antibody (or any protein of interest) genes. In another embodiment, the micro-pores are filled with a solution (i.e., for example, a culture media) comprising the biological cell clones harboring antibody (or any protein of interest) genes by degass driven forces. In one embodiment, the cells grow and express antibodies into the media, which can react and bind with a binding partner that may not be immobilized on the solid substrate or the array or, alternatively, with antigen immobilized onto a lower PDMS surface. When the device comprises a micro-pore array and a solid substrate, although it is not necessary to understand the mechanism of an invention, it is believed that, upon removal of the porous micro-pore array from the solid substrate, an antigen-antibody complex can be detected by adding fluorescent reagents to the solid substrate. It is further believed that fluorescent spots on the solid substrate giving a high signal may correspond to micro-pores containing cells secreting a specific antibody and/or protein. When the device comprises a micro-pore array and no solid substrate, although it is not necessary to understand the mechanism of an invention, it is believed that an antigen-antibody complex can be detected. In one embodiment, the method further comprises recovering the biological cells from the micro-pore array. In one embodiment, the biological cells comprise antibody secreting cells. In one embodiment, the biological cells comprise cells secreting a fluorescent protein. In one embodiment, the biological cells comprise cells secreting a fluorescent protein fused to a non-fluorescent protein. In one embodiment, the biological cells secreting a fluorescent protein fused to a non-fluorescent protein is detected directly on a solid substrate that does not have an antigen or antibody immobilized thereon.

The present invention is not in any way limited and may be used to isolate any types of biological cells, including, but not limited to, cell lines that express or produce proteins, carbohydrates, enzymes, peptides, hormones, receptors; other cell lines that produce antibodies; genetically engineered cells; and activated cells. Moreover, the present invention may be used to screen for a variety of biological activities including, but not limited to, the expression of surface receptor proteins, enzyme production, and peptide production. Furthermore, the present invention may be used to screen a variety of test agents to determine the effect of the test agents on the desired biological activity. Other types of cells desired to be isolated and screened, other types of biological activity desired to be detected, and specific test agents to be screened will be readily appreciated by one of skill in the art.

Some embodiments of the present invention provide an ability to generate and compare the activity of billions of biological cell variants. Although it is not necessary to understand the mechanism of an invention, it is believed that these embodiments not only allows the engineering of proteins and cells with new properties, but also provides a powerful new tool for understanding protein structure and function.

I. Conventional Screening Techniques

The need to isolate small numbers of specific cells from background populations is ubiquitous, with applications in pathology, clinical diagnosis, cloning, and cell biology research. In the context of cell biology experiments, sorting can be a way to select a desired starting population of cells of known characteristics, or can be a tool to analyze the results of an experiment and isolate particularly interesting cells for further investigation. Eisenstein M., *Nature* 441:1179 (2006).

Selection of hybridomas has involved screening antibodies produced by large numbers of cells and retrieving those cells that produce antibodies of desired specificity. Cloning by a limiting serial-dilution requires deposition of cells into wells of a microtiter plate (usually 96 or 384 wells) such that individual cells are deposited in roughly one out of three wells. After 5-10 d in culture, the supernatants from each well are tested, and the process of dilution is repeated until monoclonality is achieved. Two factors determine the time required to isolate a single monoclonal hybridoma by the method of Fuller et al., In: Current Protocols in Molecular Biology (eds. Ausubel, F. M. et al.) 11.8.1-11.8.2, (John Wiley & Sons, Inc., New York, 2003); and Yokoyama, W. M., In: Current Protocols in Immunology (eds. Coligan, J. E., Kruisbeek, A. M., Margulies, D. H., Shevach, E. M. & Strober, W.) 2.5.1-2.5.17, (John Wiley & Sons, Inc., New York, 1995). First, the sensitivity of the assay used to detect antibodies sets the frequency for testing; for example, sufficient concentrations of antibodies for detection by enzyme-linked immunosorbent assays (ELISA) are achieved 7-10 d after seeding individual cells into wells. Second, the total number of manipulations limits the number of clones that can be screened efficiently in any single round of selection (10-100 plates/screen).

One alternative for sorting cells into microtiter plates at limiting dilutions includes picking clones from semi-solid medium. Davis et al., "A simple, single-step technique for selecting and cloning hybridomas for the production of monoclonal antibodies" *J. Immunol. Methods* 50:161-171 (1982); and Rueda et al., "Cloning of myelomas and hybridomas in fibrin clots" *J. Immunol. Methods* 114:213-217 (1988). Another alternative for sorting cells includes fluorescence-activated cell sorting (FACS). Herzenberg et al., "The history and future of the fluorescence activated cell sorter and flow cytometry: a view from Stanford" *Clin. Chem.* 48: 1819-1827 (2002); and Carroll et al., "The selection of high-producing cell lines using flow cytometry and cell sorting" *Expert Opin. Biol. Ther.* 4:1821-1829 (2004). Cells plated in hydrogels are challenged to survive and grow slowly, whereas for FACS, the correlation is not straightforward between cells that stain positive and those that actually secrete. Both methods have improved the efficiency of screening by serial dilution.

A soft lithographic technique has been reported that supports a microengraving technique that uses microwell arrays. These microwells may contain individual cells to identify a corresponding array of molecules (including antigen-specific antibody) secreted by each cell. Love et al. (2006) "A Microengraving Method For Rapid Selection Of Single Cells Producing Antigen-Specific Antibodies" *Nature Biotechnology* 24(6): 703-707. Microengraving arrays are limited to processing approximately 100,000 individual cells in a system that identifies, recovers, and clonally expands antigen-specific antibody producing cells. Microengraving arrays are fabricated by a combination of photolithography and replica molding of monolithic slabs of PDMS forming wells that are either 50 μm or 100 μm in diameter and depth. These wells are then separated by a distance equal to the well diameter (i.e., 50 μm or 100 μm, respectively). Each PDMS slab coated with bovine serum albumin to reduce non-specific binding of the cells to the substrate surface. After depositing 0.5 ml of a cell suspension ($1 \times 10^5$-$5 \times 10^5$ cells/ml) onto the PDMS surface approximately 1-3 cells may settle into 50-75% of the wells and are cultivated for approximately 1 week. A glass slide coated with a specific antigen and/or anti-immunoglobulin antibody permits the detection of antibody secreted by individual cells. The PDMS microengraved array is then sealed against the coated glass slide, inverted, and the cells are incubated for approximately 2-4 hours, such that the secreted antibodies bind to the coated glass slide. Following the incubation, the glass slide is removed from the PDMS array, and the binding pairs on the glass slide are detected, whereas the cells within the PDMS array are further cultivated. The pattern of detected binding pairs identify the microwells containing the cells of interest. These cells of interest are collected from the microwells by a micromanipulator system (IM-9A, Narishige) fitted with hand-drawn capillaries (GC-1). To withdraw the contents of a well, the array of microwells was positioned on a microscope under a layer of medium (~1 ml), and a capillary with an outer diameter of 100 μm (inner diameter ~50 μm) was positioned directly over the top of an appropriate well. A small volume (~1-5 μl) was withdrawn with the affixed syringe until the cells were removed from the well successfully. The tip was then transferred into a well of a 96-well plate containing 200 μl medium (10% hybridoma cloning factor) and the cell(s) expelled into the volume. Both extraction from the microwell and deposition of the cells into another container (96-well plate) were monitored visually to ensure the transfer of the cells into and out of the tip.

One of the major challenges for performing cell based screening is the isolation of small populations of cells in a manner that allows for subsequent screening procedures. Traditional devices and methods of isolating cells do not adequately provide for the isolation of small populations of cells without performing steps that potentially modify cellular function or activity. Isolation of cells is not only important in screening, but also in processes that involve the monitoring, measuring, and/or use of the output of cellular activity or function (e.g. antibody production) for small populations of cells. For example, once a hybridoma fusion is performed and the cells are plated, there are several issues that have to be addressed. First, the cells will grow at different rates, thus the point at which one must perform the assay for antibody production to assess positive pools of cells can vary and may require more than one assay point on the same pool of cells. During this process, the rapidly growing cells need to be passaged in order to promote viability and to prevent loss of potentially positive clones. The next step is to perform limiting dilution with the goal of achieving clonal populations. Successive rounds of this process may be required to achieve clonal or near clonal populations. A microfluidic delivery device has been reported for isolating and screening a small population of cells (or individual cells) for biological activity—including specific antibody producing hybridomas—with minimal cell manipulation. Wang et al. "Cell Isolation And Screening Device And Method Of Using Same," U.S. Pat. No. 7,169,577. The microfluidic delivery device includes microfluidic channels that deliver cells to isolation regions both of which are manufactured by photolithography. As few as one to five cells may be delivered to each isolation region. These isolation regions contain bioaffinity regions containing ligands that bind specific types of cells to the substrate surface. Once bound to the device, the cells may undergo proliferation and then be transferred to a microarray well. A detecting device may then be inserted into the microarray well to bind to an antibody that is secreted by the cell, or the bottom of the microwell is coated with a binding ligand. This method does not contemplate recovering the specific cells for future use once the secreted compound has been detected and identified.

Various procedures for obtaining fully human antibodies have been developed, including phage display libraries of artificial antibody fragments of human origin. Boder et al., "Yeast surface display for screening combinatorial polypeptide libraries" *Nat. Biotechnol.* 15:553-557 (1997); McCafferty et al., "Phage antibodies: filamentous phage displaying antibody variable domains" *Nature* 348:552-554 (1990); Winter et al., "Making antibodies by phage display technology" *Annu. Rev. Immunol.* 12:433-455 (1994). Other methods select antibodies that are naturally produced in humans. Attempts have been made to establish hybridomas producing human mAbs or Epstein-Barr virus-immortalized human ASCs. Kozbor et al., "Requirements for the establishment of high-titered human monoclonal antibodies against tetanus toxoid using the Epstein-Barr virus technique" *J. Immunol.* 127:1275-1280 (1981); Traggiai et al., "An efficient method to make human monoclonal antibodies from memory B cells: potent neutralization of SARS coronavirus" *Nat. Med.* 10:871-875 (2004); and Winter et al., "Man-made antibodies" *Nature* 349:293-299 (1991). Furthermore, protocols for isolating antibody heavy and light chain variable region (VH and VL) complementary DNA pairs by RT-PCR directly from single B lineage cells have also been designed. Lagerkvist et al., "Single, antigen-specific B cells used to generate Fab fragments using CD40-mediated amplification or direct PCR cloning" *Biotechniques* 18:862-869 (1995); Babcook et al., "A novel strategy for generating monoclonal antibodies from single, isolated lymphocytes producing antibodies of defined specificities" *Proc. Natl. Acad. Sci. USA* 93:7843-7848 (1996); and Meijer et al., "Isolation of human antibody repertoires with preservation of the natural heavy and light chain pairing" *J. Mol. Biol.* 358:764-772 (2006). Although feasible, these systems are limited by the throughput for the selection of antigen-specific B cells. A cell-based high-throughput method has been reported for detecting and recovering individual antigen-specific antibody secreting cells using a microwell array chip that can analyze up to 234,000 individual cells (i.e. a polyclonal mixture of primary human lymphocytes) at once. Jin et al., "A Rapid And Efficient Single-Cell Manipulation Method For Screening Antigen-Specific Antibody-Secreting Cells From Human Peripheral Blood" *Nature Method* 1-6 (2009). This method has been term "immunospot array assay on a chip" wherein a conventional microarray chip (230K microwell array) comprises wells coated with generalized anti-immunoglobulin antibodies. If an antibody secreting cell is placed in these wells a distinct circular spot formed by the binding of target antigen to the specific antibodies. The antibody-secreting cells were then recovered using a micromanipulator (TransferMan NK2, Eppendorf) fitted with capillaries (Primetech) under the fluorescence microscope and then were expelled into microtubes for reverse transcription. The cDNA was then used to produce recombinant antibody.

The high functionality of an integrated microfluidic chip can lead to the realization of small instruments and disposable devices due to high sensitivity and low cost. In particular, by combining mechanical, physical, and sometimes electrical principles, microfluidic chips have evolved to carry out the manipulation of small numbers of microparticles, or sometimes a single particle, such as a cell, on a small chip. The dynamic monitoring of a single cell in an independently controlled environment is important in eliminating the influences by other cells such as a mixture of hormones, ions, and neurotransmitters released from the neighboring cells. To date, several technologies have been reported for the manipulation of single micro particle on a microfluidic chip including: i) physical capturing (Huang et al., "Transport, location, and quantal release monitoring of single cells on a microfluidic device" *Anal. Chem.* 76:483-488 (2004); Thielecke et al., "Fast and precise positioning of single cells on planar electrode substrates" *IEEE Eng. Med. Biol. Mag.* 1848-52 (1999); Wheeler et al., "Microfluidic device for single-cell analysis" *Anal. Chem.* 75:3581-3586 (2003); and Yun et al., "Micro/nanofluidic device for single-cell-based assay" *Biomed. Microdevices* 7:35-40 (2005)); ii) cell sorting (Fu et al., "A microfabricated fluorescence-activated cell sorter" *Nat. Biotechnol.* 17:1109-1111 (1999); and Shirasaki et al., "On-chip cell sorting system using laser-induced heating of a thermoreversible gelation polymer to control flow" *Anal. Chem.* 78:695-701 (2006)); iii) optical tweezers (Ashkin et al., "Optical trapping and manipulation of single cells using infrared laser beams" *Nature* 330:769-771 (1987); Arai et al., "High-speed separation system of randomly suspended single living cells by laser trap and dielectrophoresis" *Electrophoresis* 22:283-288 (2001); and Grier D., "A revolution in optical manipulation" *Nature* 424:810-816 (2003)); iv) dielectrophoresis (Müller et al., "A 3-D microelectrode system for handling and caging single cells and particles" *Biosens. Bioelectron.* 14:247-256 (1999); Hughes, "Strategies for dielectrophoretic separation in laboratory-on-a-chip systems" *Electrophoresis* 232569-2582 (2002); Manaresi et al., "A CMOS chip for individual cell manipulation and detection" *IEEE J. Solid State Circuits* 38:2297-2305 (2003); and Taff et al., "A scalable addressable positive-dielectrophoretic cell sorting array" *Anal. Chem.* 77:7976-7983 (2005)); v) electric field-driven capturing (Toriello et al., "Microfluidic device for electric field driven single-cell capture and activation" *Anal. Chem.* 77:6935-6941 (2005)); and vi) optoelectric tweezers (Chiou et al., "Massively parallel manipulation of single cells and microparticles using optical images" *Nature* 436:370-372 (2005)). But in most cases, these techniques fail to provide all of the functions required for a general bioassay, which include but are not limited to, the isolation of each chamber, chemical stimulation, and/or the monitoring of reactions in a fast and highly parallel manner. A multifunctional microwell plate in the form of a microfluidic chip with multiple microwells in a two-dimensional array for high-throughput cell analysis and drug screening has been reported using three PDMS layers and a silicon substrate to create micro-wells that physically isolate captured cells so that specific reagent(s) can be introduced into each micro-well without continuously maintaining a cell suspension media flow. Yun et al. "Multifunctional Microwell Plate For On-Chip Cell and Microbead-Based Bioassays" *Sensors and Actuators* B 143: 387-394 (2009). Specifically, the bottom PDMS layer is etched with a pattern of micro-wells and microchannels for inlet, outlet and drug injection channels. The middle PDMS layer forms a cover that seals the micro-wells. The top PDMS layer forms a connection port to a vacuum chamber that actuates the middle PDMS cover flap. The cover flap provided a tight seal such that cross-contamination between microwells is prevented. Each microwell has its own dedicated chemical injection and drain channel on the bottom side, which can induce a chemical reaction in the captured biomaterials or provide chemical excitation of the cells located in the designated target microwells by the selective injection of specific reagents. In this manner, each set of cells within each microwell can be individually exposed to different environmental conditions (i.e., for example, stimulatory and/or inhibitory hormones) without affecting the cells in a neighboring microwell. The device is not configured to recover the cells after entry and is therefore limited to bio-assays, including the capturing of bio-materials into multiple microwells, well isolation, and/or the introduction of specific chemicals.

Most conventional biochemical assays are performed using a considerable number of cells to determine their quantitative biomolecular profiles, such bulk assays only provide their averaged values in the analyzed ensemble and thus often overlook important information regarding their fluctuations among individual cells. Ferrells et al., *Science* 280:895-898 (1998); and Levsky et al., *Trends Cell Biol.* 13:4-6 (2003). Some believe that to perform quantitative analysis of intracellular biological contents at the single-cell level must integrate cell lysis followed by a quantitative analysis of biochemical contents in the lysate. For example, a multiplexed single-cell analyses method reported thus far take advantage of highly sophisticated and automated instruments for integration of these multiple steps on a single platform, e.g., single-cell capture followed by chemical lysis in a closed volume of 50 pL recently reported in a microfabricated device. Irimia et al., *Anal. Chem.* 76:6137-6143 (2004). However, the complicated flow path and process of the microfabricated device in that report could be a serious drawback for extending the application to single-cell biochemistry. A single-cell lysis method has been reported for analyzing intracellular content and enzymatic activity at the cellular level using a dense array of microwells (10-30 picoliter) fabricated in PDMS. Experimental assays on single cells isolated within these microwells demonstrate the ability to detect proteins by antibody conjugated microbeads as well as protease activity by fluorescent substrates. Sasuga et al. "Single-Cell Chemical Lysis Method For Analyses Of Intracellular Molecules Using An Array Of Picoliter-Scale Microwells" *Analytical Chemistry* 80(23): 9141-9149 (2008). As this method inherently results in the lysis of the evaluated cells, they cannot be recovered for future use after identification of their biochemical content.

Optical cell manipulation methods centered around optical tweezers have been adapted to cell sorting and are intuitive wherein a user directly focuses a laser onto a target cell and uses the beam to tweeze or push the cell to a desired location. Ashkin et al., *Optics Letters* 11:288-290 (1986): and Buican et al., *Applied Optics* 26:5311-5316 (1987). Optical tweezer arrays and optical lattices can optically manipulate and sort multiple cells and particles simultaneously. Grier D G., *Nature* 424:810-816 (2003); and MacDonald et al., *Nature* 426:421-424 (2003). However, the high-numerical aperture (NA) requirements of optical tweezers greatly restrict imaging field size and constrain device architecture due to the short working distances of the objective lenses typically used. While a small field size is sufficient to work with large numbers of small particles or small cells such as bacteria, only small numbers of mammalian cells can fit in such a small field ($\sim$2500 $\mu m^2$) for optical tweezer array-based manipulation. Further, power requirements are high, as each trap site might require upwards of $\sim$100 mW of optical power Optoelectronic tweezers (OETs) employ lower-NA optics, and thus enable larger area ($\sim$1 mm2) manipulation fields via optically mediated dielectrophoretic (DEP) trap arrays, extending "virtual" optical manipulation to field areas better suited for mammalian cell manipulation. Chiou et al., *Nature* 436:370-372 (2005). Unfortunately, owing to buffer incompatibilities, OET forces exerted on cells suspended in standard cell culture medium are weak, and a $\sim$1 $mm^2$ manipulation area, while an improvement over traditional optical tweezers, is still insufficient to simultaneously manage large populations of cells. Use of a large-area display to directly actuate OETs without lenses circumvents the issue of lens field size, but decreases manipulation resolution and suffers from the same buffer incompatibilities of traditional OETs. Choi et al., *Microfluidics and Nanofluidics* 3:217-225 (2007). Array-based systems employing non-optical confinement methods can form arrays of cells extending beyond a single imaged field. DEP trap arrays have successfully demonstrated trap and release sorting capability and can, in principle, be scaled to large array sizes. Taff et al., *Analytical Chemistry* 77:7976-7983 (2005). Unfortunately, such site-addressable electrical approaches require complex on-chip interconnects and significant off-chip support circuitry when scaled to large array sizes. Hydrodynamic trap arrays, utilizing either microwells or obstacles for cell confinement, offer simple, passive, mostly single-cell loading over large areas with minimal complexity, allowing microscopy-based imaging of large arrays over time to investigate single-cell behavior. Rettig et al., *Analytical Chemistry* 77:5628-5634 (2005); and Di Carlo et al., *Lab on a Chip* 6:1445-1449 (2006). Viable retrieval of small numbers of single cells from microwell arrays using micropipettes/micromanipulators based on temporal fluorescence behavior has also been demonstrated, but the retrieval method is time-consuming and cumbersome. Love et al., *Nature Biotechnology* 24:703-707 (2006); and Yamamura et al., Analytical Chemistry 77:8050-8056 (2005). A microscope-compatible microfluidic cell-sorting device has been reported that contains a microwell array that is passively loaded with mammalian cells via sedimentation prior to visual inspection by microscopy. Kovac et al. "Intuitive, Image-Based Cell Sorting Using Opto-Fluidic Cell Sorting" *Analytical Chemistry* 79(24):9321-9330 (2007). A PDMS microwell array is molded from a silicon wafer master that produces 105 μm flow channels and 25-30 μm diameter posts to pattern a microwell array. This array supports over 10,000 individually addressable trap sites. A glass slide was then bonded to the microwell array to complete the formation of a sealed chamber. An infrared laser is then focused upon a single cell (i.e. within a single microwell) resulting in actuation and levitation from the microwells into a flowing media for collection. This method is limited to image-based cell sorting and the devices are not configured to detect any secreted biochemical compounds into the media solution.

Other microarray methods that isolate biological cells including but not limited to: i) a multi-analyte biosensor chip comprising electrodes for electrical measurement of analytes (Saleh et al., "Direct Detection of Antibody-Antigen Binding Using An On-Chip Artificial Pore" *PNAS* 100(3): 820-824 (2003)); ii) measuring cellular responses (i.e. drug testing, toxicology and basic cell biology) using phase-contrast and fluorescence micrographs (Rettig et al. "Large-Scale Single-Cell Trapping And Imaging Using Microwell Arrays" *Analytical Chemistry* 77(17): 5628-5634 (2005)); iii) microwell cell culture substrates capable of cultivating hundreds to thousands of individual cell cultures (Charnley et al., "Integration Column: Microwell Arrays For Mammalian Cell Culture" *Integrative Biology* 1: 625-634 (2009)); iv) single cell analysis platform for microscopic analysis, on-chip fluorescent assays and enzyme kinetics (Di Carlo et al., "Single-Cell Enzyme Concentration, Kinetics, and Inhibition Analysis Using High-Density Hydrodynamic Cell Isolation Arrays" *Analytical Chemistry* 78(14): 4925-4930 (2006)); v) detecting single antigen specific B cells based on fluctuations in antigen-induced intracellular $Ca^{2+}$ immobilization and/or fluorescence-labeled antigen binding (Kinoshita et al., "Identification Of Antigen-Specific B Cells By Concurrent Monitoring Of Intracellular Ca2+ Mobilization And Antigen Binding With Microwell Array Chip System Equipped With A CCD Imager" *Cytometry Part A* 75A(8): 682-687 (2009)); vi) a hydrogel microwell for dynamically studying the fate of single cells by time-lapse microscopy. "Regulation Of Stem Cell Fate In Bioengineered Arrays Of Hydrogel Microwells" *California Institute for Regenerative Medicine*, cirm.ca.gov/node/46.

II. Screening Problems Solved by the Direct Cloning and Selection Technology

Conventionally used screening display methods (i.e., for example, phage display) have numerous technical challenges, including, but not limited to, size of protein displayed has to be small, multiplicity of infection (MOI) needs to be high to avoid loss of diversity, is dependent on the activity of the phage, technically challenging and needs highly trained people, multiple panning rounds needed (taking up to 1 week or more), high non-specific binding due to phage, antibodies may not function well in soluble form (truncated clones are often expressed), and/or avidity effects can hinder selection of high affinity clones.

Figure 14:
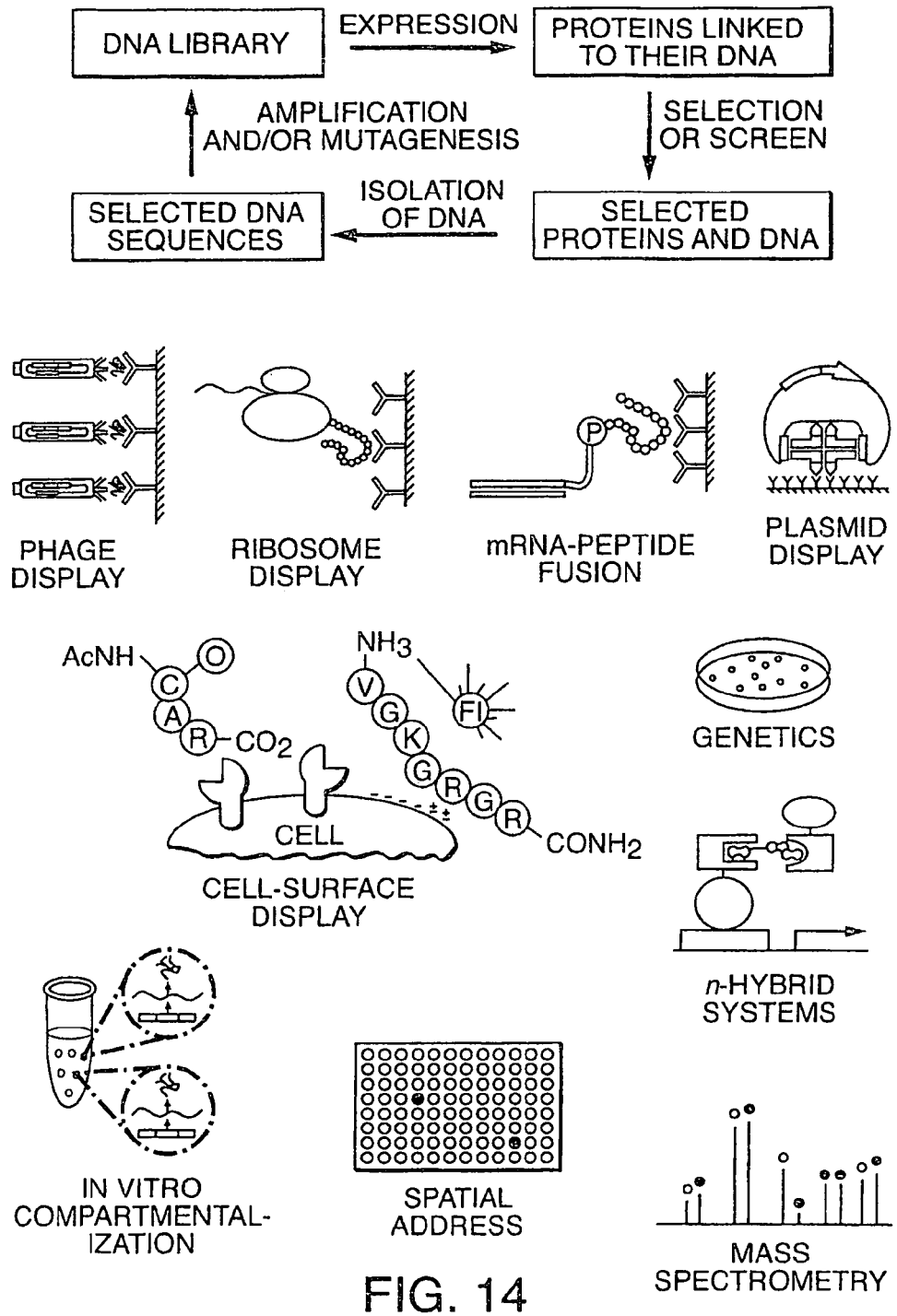
FIG. 14 presents a generalized overview of conventional high throughput processes of identifying interaction pairs (pairs of binding partners) in parallel.

A generalized overview of conventional high throughput processes for identifying interaction pairs in parallel is described below. See, FIG. 14 Starting with a source of DNA (usually millions of different copies), proteins are translated (either in vitro or in vivo) from the DNA and linked to a screening substrate. Through multiple rounds of screening, specific binders are separated from background non-specific binders. Target clones are subsequently recovered and re-amplified via their genotype-phenotype linkage. The most commonly used methods are the 'display' methods, especially phage display. Traditionally, spatial addressing methods can be simple and efficient, but are limited by the numbers of clones that be analyzed. For the first time, the present invention provides a spatial addressing technique that match phage and cell display technologies in cell number but with greater efficiency in a shorter time.

In particular, conventional bacteriophage display screening techniques have specific disadvantages including but not limited to requiring the display of the protein, high non-specific binding levels (i.e., providing a low signal-to-noise ratio), or a prolonged period of time in which to run the assay (i.e., for example, fourteen days). On the other hand, direct clone analysis and selection has specific advantages over these conventional screening methods, including, but not limited to: recovery of the cells is not limited by a display of a particular protein, low non-specific binding level (i.e., providing a high signal-to-noise ratio), short period of time in which to run the assay (i.e., for example, two days), highly parallel and scalable thereby allowing the testing of millions or billions of recombinant antibodies in a single cycle; a pore-based array which has distinct advantages over well-based arrays, a very high density micro-pore array for screening biological interactions, selection of biological material and cells using a commercially available micro-pore array (manufactured by the bonding of millions or billions of silica capillaries and the fusing them together through a thermal process); screening millions (or billions) of biological interactions in parallel; independent recovery of millions of target cells; provides qualitative concentration versus affinity information for millions of clones in parallel. (e.g. feedback on production efficiency is provided for each expressed gene); eliminates the non-specific binding due to phage display; true monovalent binding, simultaneous testing of at least two (or more) different antigens per pore (e.g. simultaneous positive and negative screening); significant reductions in assay time (i.e., for example, for 14 days, to 1-2 days), significant reduction in costs of new antibody discovery; and/or does not require complex biological procedures, thus is be more reproducible and robust.

Figure 19A:
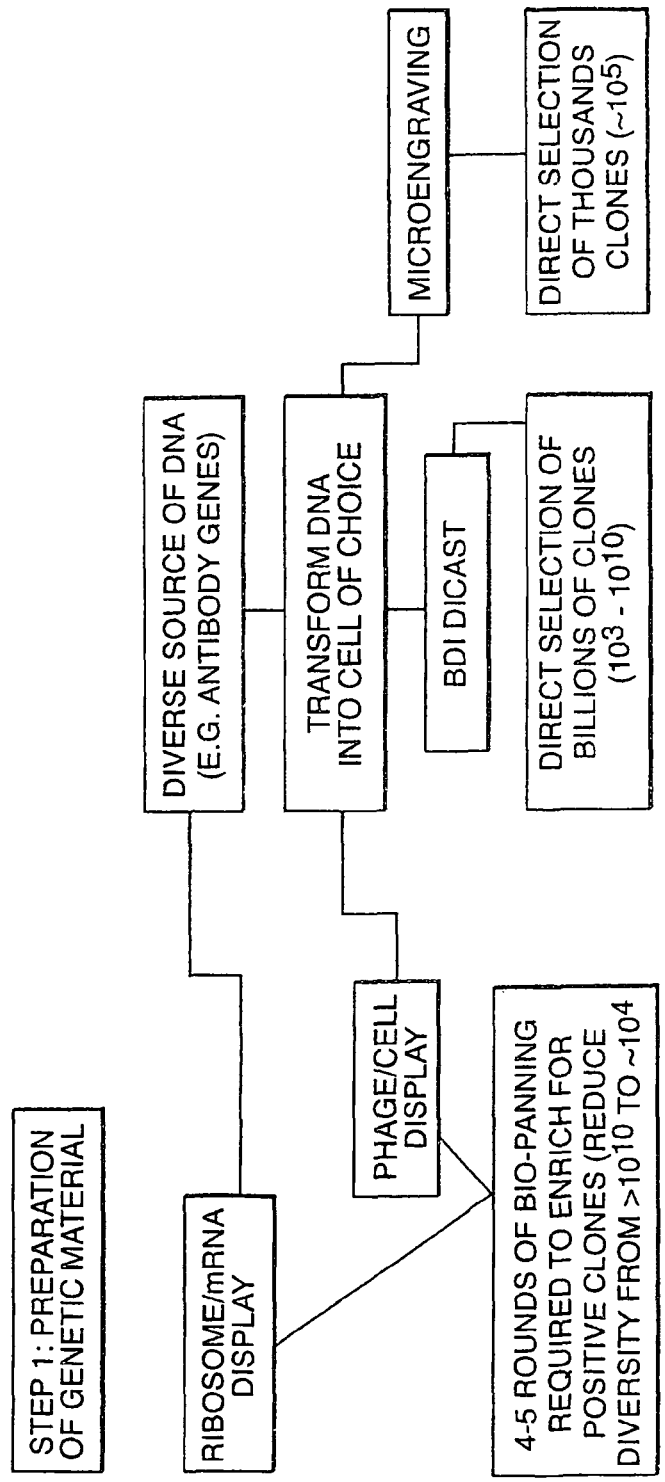
FIG. 19 (FIGS. 19A, 19B and 19C) illustrates some of the primary advantages of the direct clone analysis and selection technique described herein, as compared to conventional ribosomal, phage display, and microengraving screening techniques.
Figure 19B:
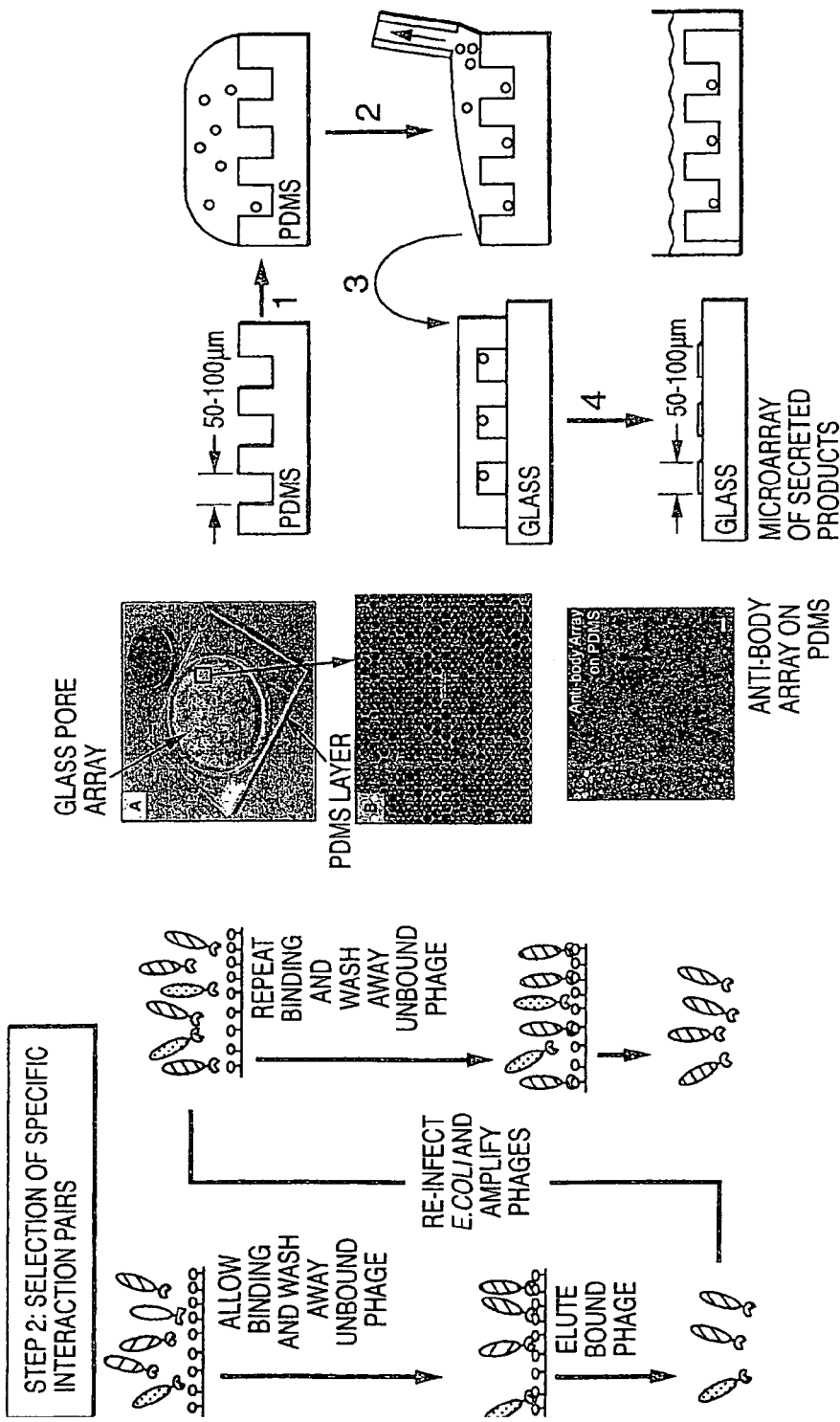
Figure 19C:
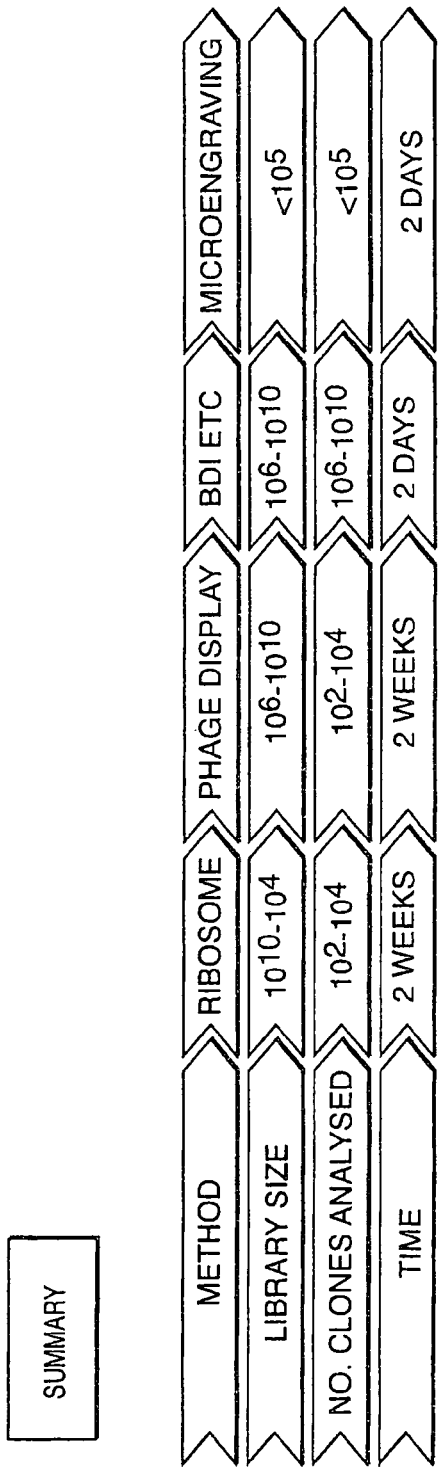

The present invention is capable of processing a number of cells that is orders of magnitude greater that any known screening technique. The present invention is similar to ribosome, phage display, and microengraving only to the point of collecting DNA, and transforming the cells with the collected DNA. Both ribosomal and phage selection processes require multiple rounds (i.e., bio-panning) to enrich for the cells of interest, while microengraving is limited by both the depth of the wells and the number ($\sim 10^5$). See, FIG. 19A, Step 1. The present invention is capable of selecting for interactions between binding pairs having an improved specificity over known screening techniques that cannot handle the rapid and error-free extraction of thousands (or more) of cells. For example, the repeated nature of ribosomal and phage display panning inherently results in the arbitrary loss of specific types of binding pairs, while microengraving is limited to micromanipulator capture techniques thereby inducing error and recovery losses to recover specific cells. For example, such microengraving techniques cannot handle the fast and error free extraction of 1000 s or more cells. See, FIG. 19B, Step 2. In summary, the direct clone analysis and selection technique described herein provides advantages in the largest total screened cell number in the shortest possible time. See, FIG. 19C, Summary.

III. Methods of Making Direct Cloning and Selection Arrays

Microarrays have been created by sectioning bundles of small plastic rods, fibers, tubes or tubules wherein biological components (i.e. nucleic acid fragments, nucleotides, antigens, antibodies, proteins, peptides, carbohydrates, ligands, receptors, drug targets or biological cells) are bound to (i.e., immobilized) the sides of the rods or fibers during their manufacture. Anderson et al. "Microarrays And Their Manufacture By Slicing," U.S. Pat. No. 7,179,638 (herein incorporated by reference). These microarrays that are coated with biological components are used to perform a variety of different quantitative biochemical analyses such as enzymatic activities, immunochemical activities, nucleic acid hybridization and small molecule binding. These immobilized binding components may be coated on the inside or outside of microtubes, contained in a gel that is placed within the microtubes, or attached/embedded in small particles or beads that fill the tubes. When the individual fibers are solid rods or filaments, the binding components may be incorporated on the rod of filament surface, or impregnated within the filament during casting of a filament block. Consequently, each coated microarray section that is cut from the same block constitutes a coated microarray for use in the same binding assays. For example, a block that is a meter long can be cut into 10-micron thick sections thereby yielding 100,000 identical coated microarrays.

Unlike the micro-pore array of the present invention, the coated microarray may also have specific fibers incorporated with a solidifying medium (i.e., for example, a hydrogel or bead) attached to the binding components prior to filling the hollow fibers thereby creating a mini-matrix to support biochemical reactions. Further, the coated microarrays filled with a supporting medium by using hydrostatic force or centrifugal force, rather than a superior, but optional, method of using a degassed solid substrate utilized by embodiments of the present invention as described herein.

Generally, the biological cells and/or biochemical reactants are immobilized within individual fibers prior to slicing off the coated microarrays, such that the cells/reactants are retained inside the hollow fibers after the microarray is formed. Generally, the cell density introduced into each fiber exceeds 1 million cells per square centimeter, but when using smaller fibers microarrays may comprise up to at least 10 billions cells per square centimeter of the array. These prefilled coated microarrays are intended for long-term storage for use in analysis and detection assays. The coated microarrays are not compatible with the detection of in vivo secretion of biological agents from freshly cultivated biological cells.

Unlike the micro-pore array of the present invention, the coated microarrays are then attached directly between at least two adhesive surfaces, flexible films or solid surfaces to produce microarray chips, such that the coated microarray is sandwiched in between the two solid substrates. These coated microarrays might be used for cloning of biological cells, viruses or other particles by adding dilute suspensions to the microarray but they are incompatible with the direct cloning and selection technology described herein.

Figure 15:
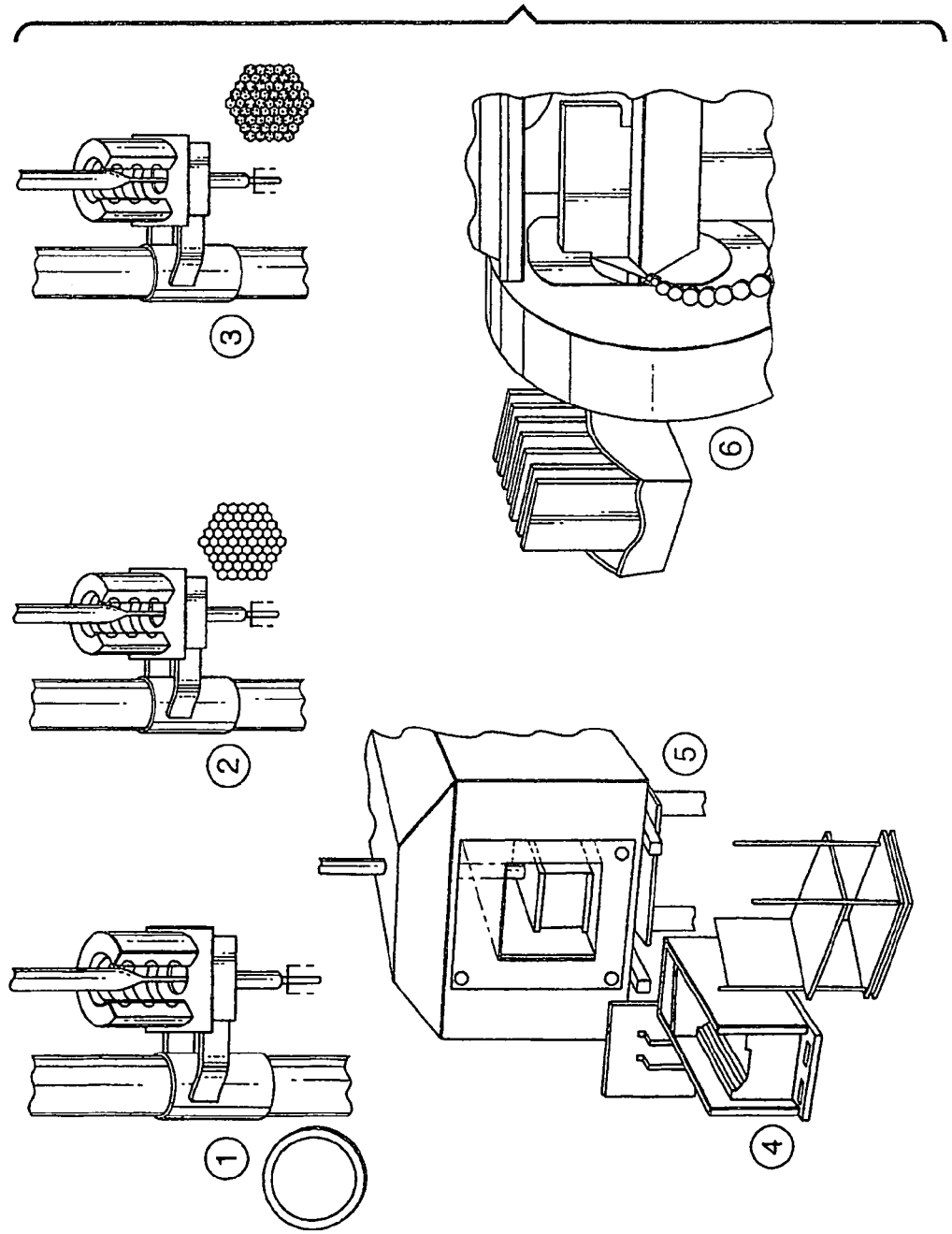
FIG. 15 presents one embodiment for constructing a fused block of capillary fibers or a micro-pore array.
Figure 16:
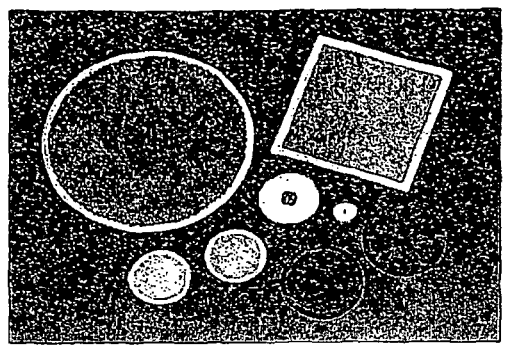
FIG. 16 present several commercially available glass capillary fiber compositions or micro-pore arrays, useful in the present invention (Cat #'s: J5022-01, J5022-09, J5022-11, J5022-16, J5022-19 J5022-21; Hamamatsu, Japan).

The micro-pore arrays contemplated herein can be manufactured by bundling millions or billions of silica capillaries and fusing them together through a thermal process. Such a fusing process may comprise the steps including but not limited to; i) heating a fiber single draw glass that is drawn under tension into a single clad fiber; ii) creating a fiber multi draw single fiber from the single draw glass by bundling, heating, and drawing; iii) creating a fiber multi-multi draw multi fiber from the multi draw single fiber by additional bundling, heating, and drawing; iv) creating a block assembly of drawn glass from the multi-multi draw multi fiber by stacking in a pressing block; v) creating a block pressing block from the block assembly by treating with heat and pressure; and vi) creating a block forming block by cutting the block pressing block at a precise length (i.e., for example, 1 µm). See, FIG. 15. In one embodiment, the method further comprises slicing the silica capillaries, thereby forming a very high-density glass micro-pore array plate. It will be appreciated that the array of micro-pores for use in the present invention can be formed by any suitable method, as long as the internal diameter of the micro-pores ranges between approximately 1.0 micrometers and 500 micrometers. In one embodiment, the capillaries are cut to approximately 1 millimeter in height, thereby forming a plurality of micro-pores having an internal diameter between approximately 1.0 micrometers and 500 micrometers. In one embodiment, the micro-pores range between approximately 10 micrometers and 1 millimeter long. In one embodiment, the micro-pores range between approximately 10 micrometers and 1 centimeter long. In one embodiment, the micro-pores range between approximately 10 micrometers and 10 millimeter long. In one embodiment, the micro-pores range between approximately 10 micrometers and 100 millimeter long. In one embodiment, the micro-pores range between approximately 0.5 millimeter and 1 meter long.

Such processes form a very high-density micro-pore array that is used in the present invention. In some arrays, each micro-pore comprises a 5 µm diameter and an approximate 66% open space. In some arrays, the array is 10×10 cm and comprises over 300 million micro-pores. See, FIG. 1. In some arrays, the proportion of the array that is open (i.e., comprises the lumen of each micropore) ranges between about 50% and about 90%, for example about 60 to 75%, such as a micropore array provided by Hamamatsu and having an open area of about 67%.

The internal diameter of micro-pores ranges between approximately 1.0 micrometers and 500 micrometers. In some arrays, each of said micro-pores can have an internal diameter in the range between approximately 1.0 micrometers and 300 micrometers; optionally between approximately 1.0 micrometers and 100 micrometers; further optionally between approximately 1.0 micrometers and 75 micrometers; still further optionally between approximately 1.0 micrometers and 50 micrometers, still further optionally, between approximately 5.0 micrometers and 50 micrometers.

In some arrays, the open area of the array comprises up to 90% of the open area (OA), so that, when the pore size varies between 10 μm and 500 μm, the number of micro-pores per $cm^2$ of the array varies between 458 and 1,146,500, as is represented in the table below. In some arrays, the open area of the array comprises about 67% of the open area, so that, when the pore size varies between 10 μm and 500 μm, the number of micro-pores per $cm^2$ of the array varies between 341 and 853,503, as is represented in the table below. It will be appreciated that, with a pore size of 1 μm and up to 90% open area, each $cm^2$ of the array will accommodate up to approximately 11,466,000 micro-pores.

| Pore diameter (um) | No of pore (90% OA) | No of pores (67% OA) |
| --- | --- | --- |
| 500 | 458 | 341 |
| 300 | 1275 | 948 |
| 100 | 1150 | 8,535 |
| 75 | 20,380 | 15,172 |
| 50 | 45,860 | 34,140 |
| 10 | 1,146,500 | 853,503 |
| 1 | 11,465,967 | 85,350,318 |

Figure 2:
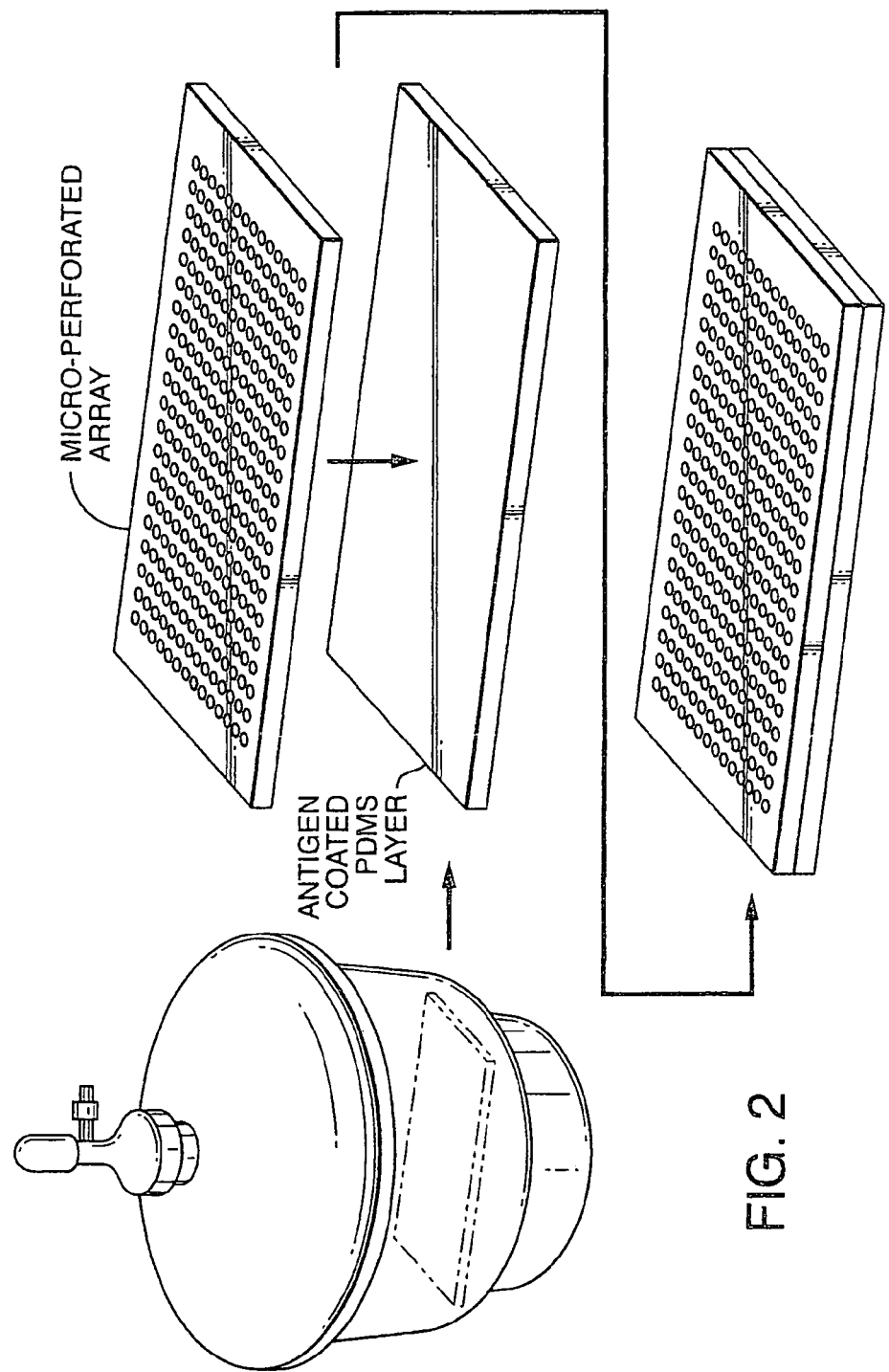
FIG. 2 illustrates one embodiment of making a degassed glass micro-pore testbed array, the testbed array comprising a micro-pore array reversibly attached to a solid substrate.
Figure 3:
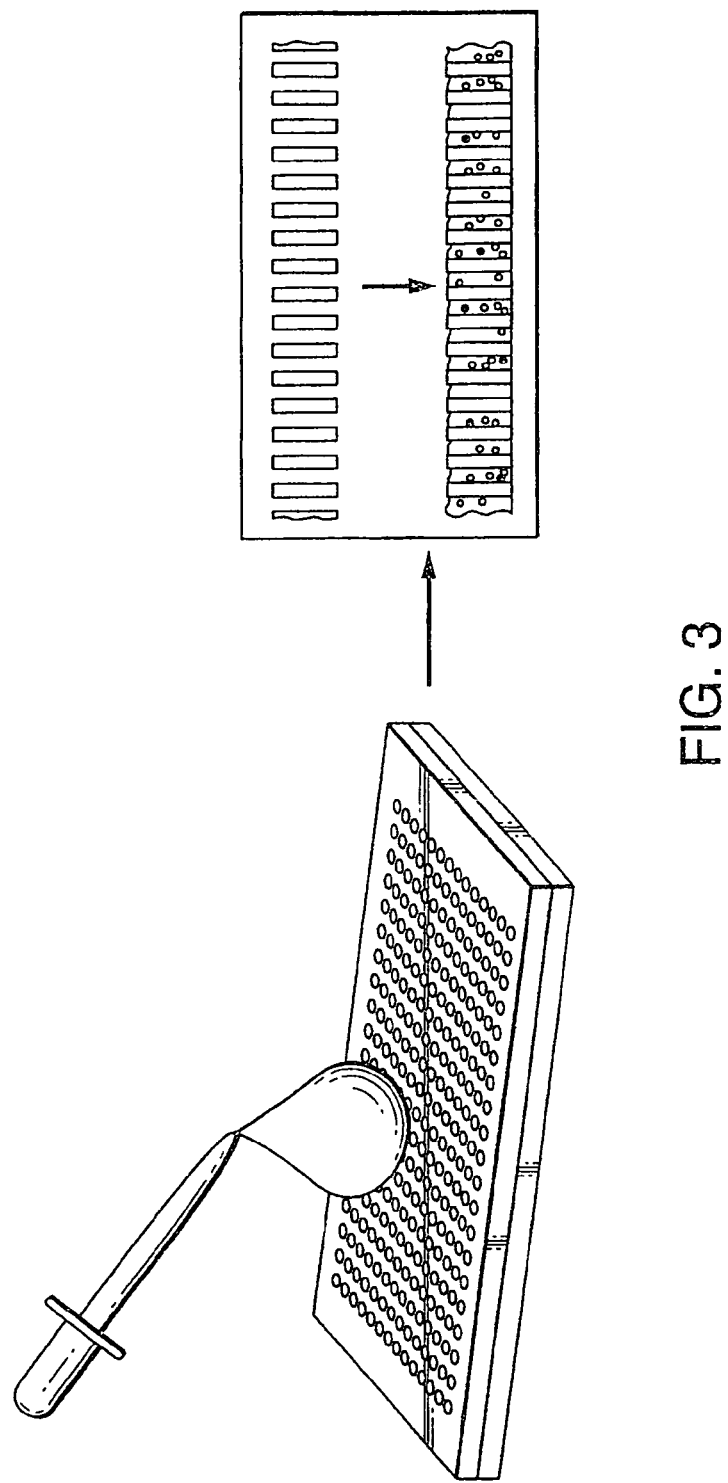
FIG. 3 illustrates one embodiment for loading the micropores of a glass micro-pore testbed array.
Figure 27:
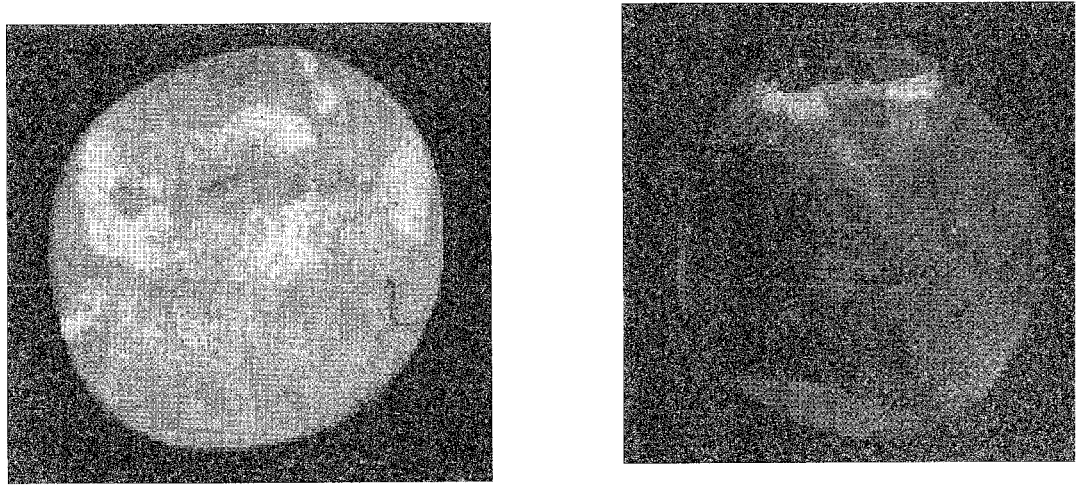
FIG. 27 demonstrates enhanced surface coating with APTES coated PDMS.

In one embodiment, the method further comprises coating a solid substrate with a binding partner. In one embodiment, the binding partner comprises an antigen. In one embodiment, the solid substrate comprises PDMS. In one embodiment, the method further comprises degassing the solid substrate to activate a degassed driven flow (i.e., for example, for approximately fifteen minutes). In one embodiment, the method further comprises placing the glass micro-pore array plate on the degassed solid substrate to create a degassed testbed array. See, FIG. 2. Although it is not necessary to understand the mechanism of an invention, it is believed that degassing the solid substrate results in self-powered pumping to load the glass micro-pore array plate with a media solution. Degassing of the solid substrate is, however, not needed to load the glass micro-pore array plate with a media solution. See, FIG. 27.

In one embodiment, the present invention contemplates a method for loading a degassed testbed array comprising contacting a solution comprising a plurality of cells with the degassed testbed array to form a loaded testbed array. Generally, degassing of a solid substrate, such as PDMS, is performed by placing the substrate in a vacuum chamber for one to three hours.

A degassed substrate (i.e. PDMS) permits the removal of gas, such as air bubbles for example, from the substrate as well as the overlying capillaries that may hinder or prevent direct interactions between antigen immobilized on the substrate surface and antibody present in the media. The capillaries attached to a sufficiently degassed substrate may be loaded with sample for a period of time following the degassing step. In some instances the sample may be loaded into the capillaries an hour (or more) after the degassing step has been performed. The substrate may be degassed multiple times if necessary. For example, the degassing step may be repeated if the sample is not loaded quickly enough following the initial degassing step.

In another embodiment, the present invention contemplates a method for loading a testbed array comprising contacting a solution comprising a plurality of cells with the testbed (non-degassed) array to form a loaded testbed array.

Figure 20:
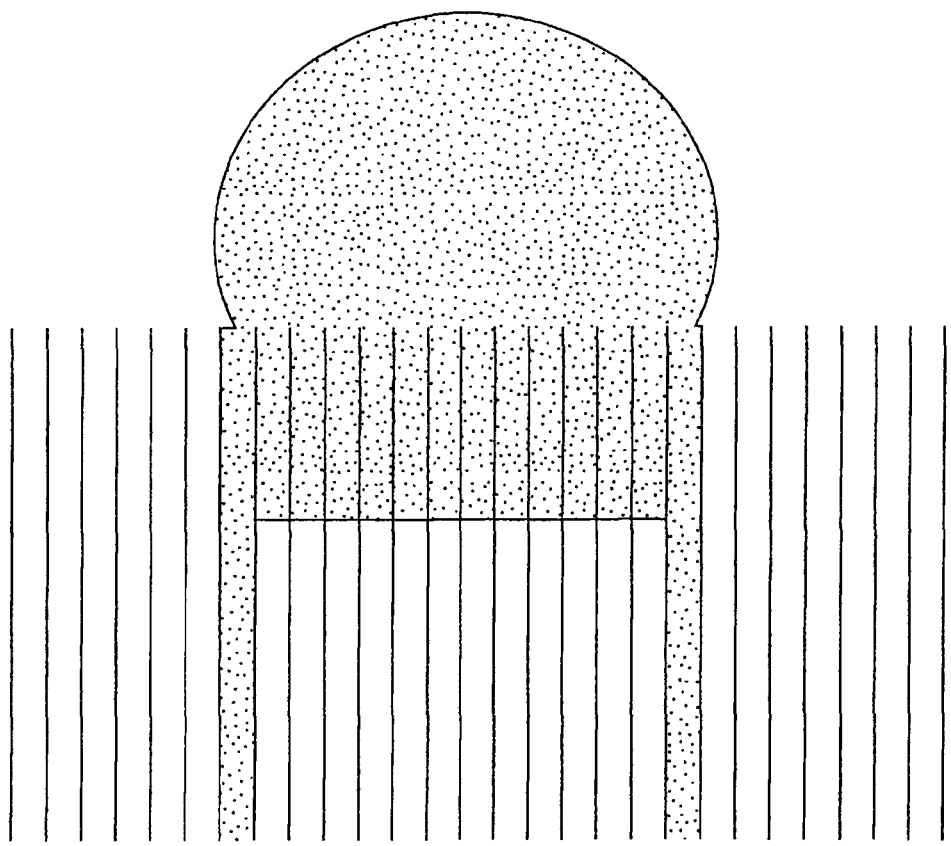
FIG. 20 demonstrates that surface tension actually prevents a liquid drop (suspension of heterologous cells, for example) from entering the central micro-pores.
Figure 21:
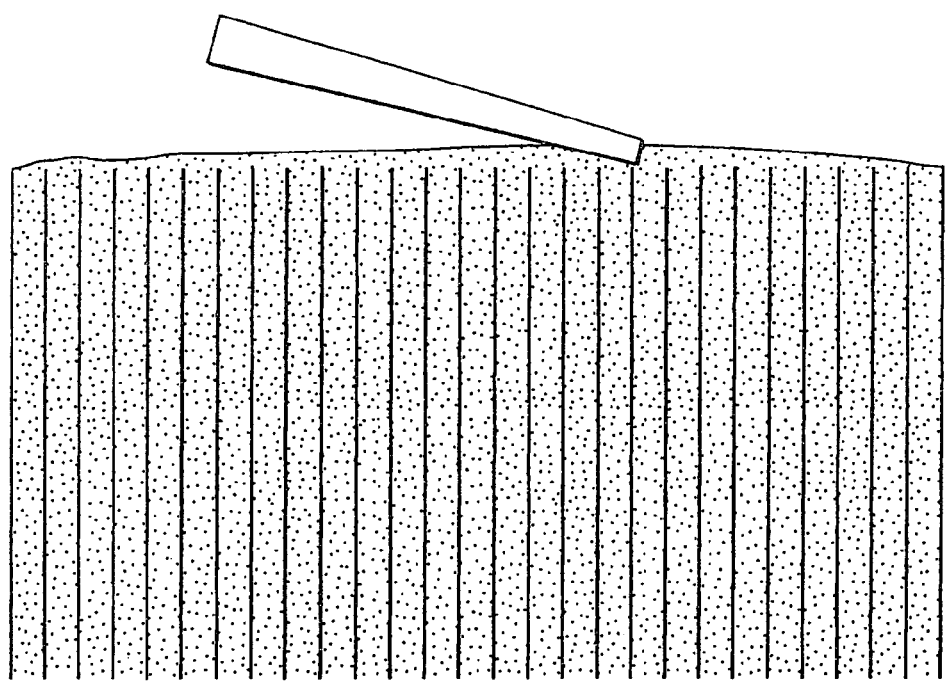
FIG. 21 demonstrates that, when the drop is spread evenly over the micro-pore array surface, the surface tension is removed and all micro-pores are filled evenly.
Figure 22C:
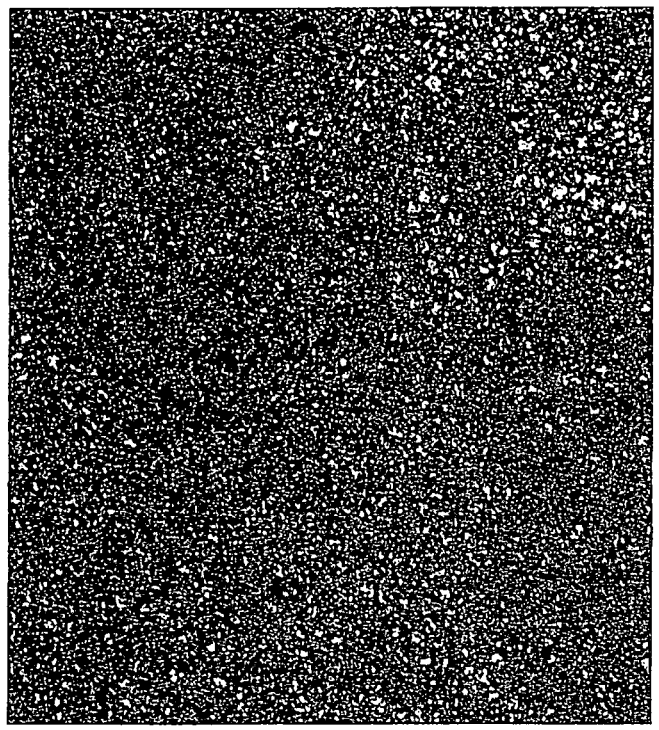
FIG. 22 (FIGS. 22A, 22B and 22C) presents exemplary data showing the elimination of a halo ring effect following detection of the appropriate analyte when the solution drop is spread evenly across the top of the micro-pore array.
Figure 22A:
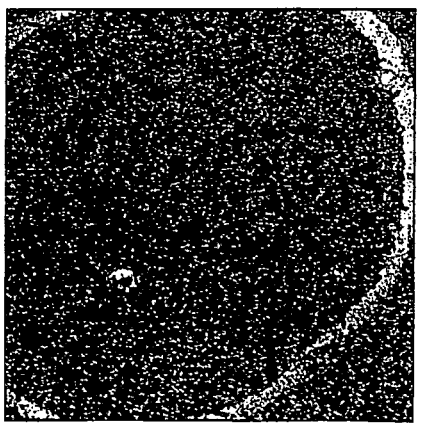
Figure 22B:
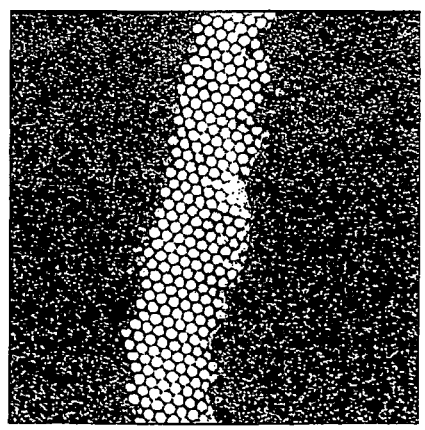

In one embodiment, loading a mixture of antibody secreting *E. coli* evenly into all the micro-pores comprises placing a 500 μL droplet on the upper side of the array and spreading it over all the micro-pores. The heterologous population of cells can be loaded onto the micro-pore array. If a solid substrate is present, the heterologous population of cells can be loaded onto the micro-pore array prior to reversible attachment of the micro-pore array with the solid substrate. Aternatively, if a solid substrate is present, the heterologous population of cells can be loaded onto the micro-pore array after reversible attachment of the micro-pore array with the solid substrate. In one embodiment, an initial concentration of approximately $10^9$ cells in the 500 μL droplet results in approximately 3 cells (or sub-population) per micro-pore. In one embodiment, each micro-pore has an approximate volume of between 20-80 pL (depending on the thickness of the glass capillary plate of between 250 μm to 1 mm). Once the micro-pores are loaded and incubated overnight, each micro-pore should then contain approximately 2,000-3,000 cells per micro-pore. In one embodiment, the cells may be cultivated for up to forty-eight hours without loss of viability in order to maximize the proliferation yield. Although it is not necessary to understand the mechanism of an invention, it is believed that "spreading" the droplet over all the micro-pores provides for optimal distribution of cells in the various micro-pores. Theoretically, adding a drop to the micro-pore array should fill all pores evenly. However, an empirical evaluation demonstrated that surface tension actually prevents the drop from entering the central micro-pores. See, FIG. 20. If the drop is spread evenly over the micro-pore array surface the surface tension is removed. See, FIG. 21. Consequently, if the drop is placed straight down on the micro-pore array, only the pores at the edge of the drop fill due to reduced surface tension (also evaporation recedes the drop so that the liquid is no longer held in suspension). This causes a halo ring effect following detection of the appropriate analyte. See, FIGS. 22 (A, B and C). In one embodiment, the solution comprises approximately three (3) microliters. In one embodiment, the plurality of cells may be selected from the group comprising animal cells, plant cells, and/or microbial cells. In one embodiment, the plurality of cells comprise *E. coli* cells. In one embodiment, the *E. coli* cells secrete at least one recombinant compound of interest. In one embodiment, the recombinant compound of interest has an affinity for the binding partner. Although it is not necessary to understand the mechanism of an invention, it is believed that, if there are approximately $10^9$ cells in an approximate 500 μL solution then, on average, there should be approximately three (3) cells per micro-pore for an array having approximately 3–4×$10^6$ micro-pores. It should be noted that the exact number will depend on the number of pores in the array. For example, if an array has approximately 3–4×$10^6$ micro-pores, it therefore, would have approximately 500-100 cells/pore. In one embodiment, each micro-pore comprises a volume of ranging between approximately 20-80 picoliters.

IV. Methods of Using Direct Cloning and Selection Arrays

The data described herein demonstrate that superior antigen-specific positive signal is obtained when soluble antibody is produced by on-plate culturing rather than in test tubes. Results further demonstrate that the high degree of non-specific binding that occurs during phage display is totally eliminated when the antibody is selectively expressed in soluble form from specific cells that are compartmentalized within a micro-pore. In addition, the use of whole phage particles leads to poor resolution due to their large size relative to the displayed antibody. Thus, in addition to being faster and easier to use, the ability to detect secreted antibody allows this micro-pore array to provide higher resolution than current methods that rely upon the target molecule being expressed on the surface of a display vector (i.e. phage display, ribosome display, mammalian cell display, bacterial cell display or yeast display). Additional benefits of this array as compared to phage display methods include the ability to simultaneously test two (or more) target molecules per pore (i.e. positive and negative screening) and not being limited by the size of the protein being examined since phage-displayed proteins have to be small.

A. Biological Recognition Assays

Although it is not necessary to understand the mechanism of an invention, it is believed that the testbed arrays described above comprise micro-pores having sufficient volume to incubate the cells for between 0-48 hours, such that compounds of interest are secreted from the cells and bind to the binding partner. Consequently, a plurality of biological recognition assays may be performed either within, or between, each of the micro-pores. For example, one such recognition assay may comprise antigen-antibody binding.

Figure 4:
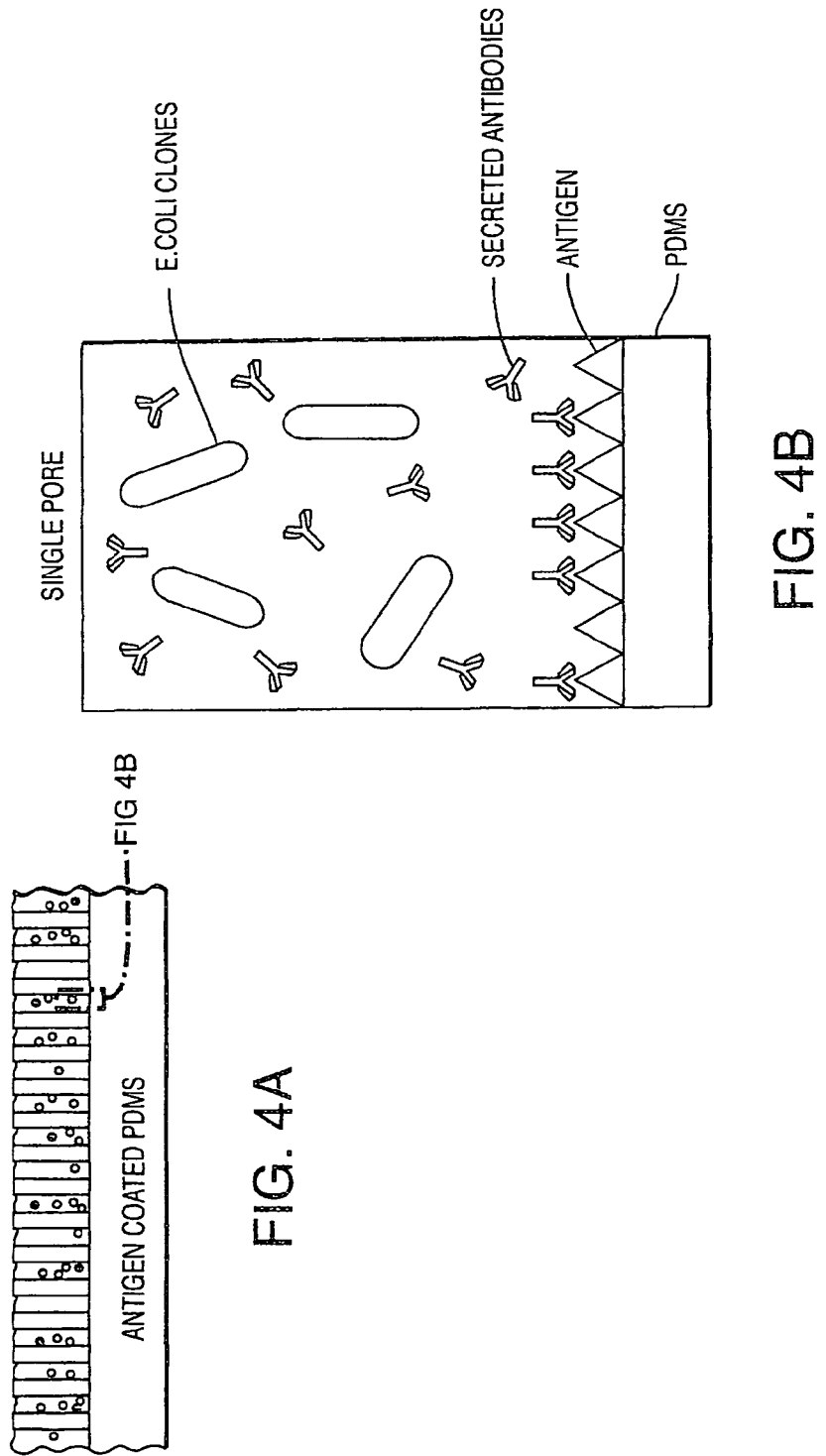
FIG. 4 (FIGS. 4A and 4B) illustrates one embodiment of a biological recognition assay performed within each micropore. For example, the recognition assay may comprise an antigen-antibody recognition assay.

In one embodiment, the present invention contemplates a method for antigen-antibody binding comprising incubating a plurality of cells at 37° C. for 1-24 hrs such that each cell produces antibodies and secretes the antibodies into the micro-pore. In one embodiment, the antibody is a recombinant antibody. In one embodiment, the antibody is a monoclonal antibody. In one embodiment, at least one of the cells produces more than one antibody. Although it is not necessary to understand the mechanism of an invention, it is believed that because of the micro-pore architecture, this incubation is relatively free of evaporation losses due to the very narrow inlets (thus small exposed surface area) and the extreme length of the pores. In one embodiment, the antibody secretion is stimulated by an induction agent. In one embodiment, the induction agent comprises IPTG. See, FIG. 4.

In one embodiment, the present invention contemplates an in-solution binding assay, wherein each binding partner is in solution or suspension. Such binding partners include, but are not limited to: Bimolecular fluorescence complementation (BiFC); Protein-Fragment; Complementation Assays (PCA) such as with Split ubiquitin, β-Galactosidase, β-Lactamase, Luciferase, DihydrofolateReductase and Green Fluorescent Protein); Yeast two hybrid (Y2H); Bacterial two hybrid; Tandem affinity purification (TAP); Fluorescence resonance energy transfer (FRET); Bioluminescence resonance energy transfer (BRET); Homogeneous fluorescence polarization assay; Amplified Luminescent Proximity Homogeneous Assay; Homogeneous Caspases Assay; Back-Scattering Interferometry (BSI) and Particle-based systems fluorescent or plasmonic systems.

B. Cell Isolation and Selection

Figure 5:
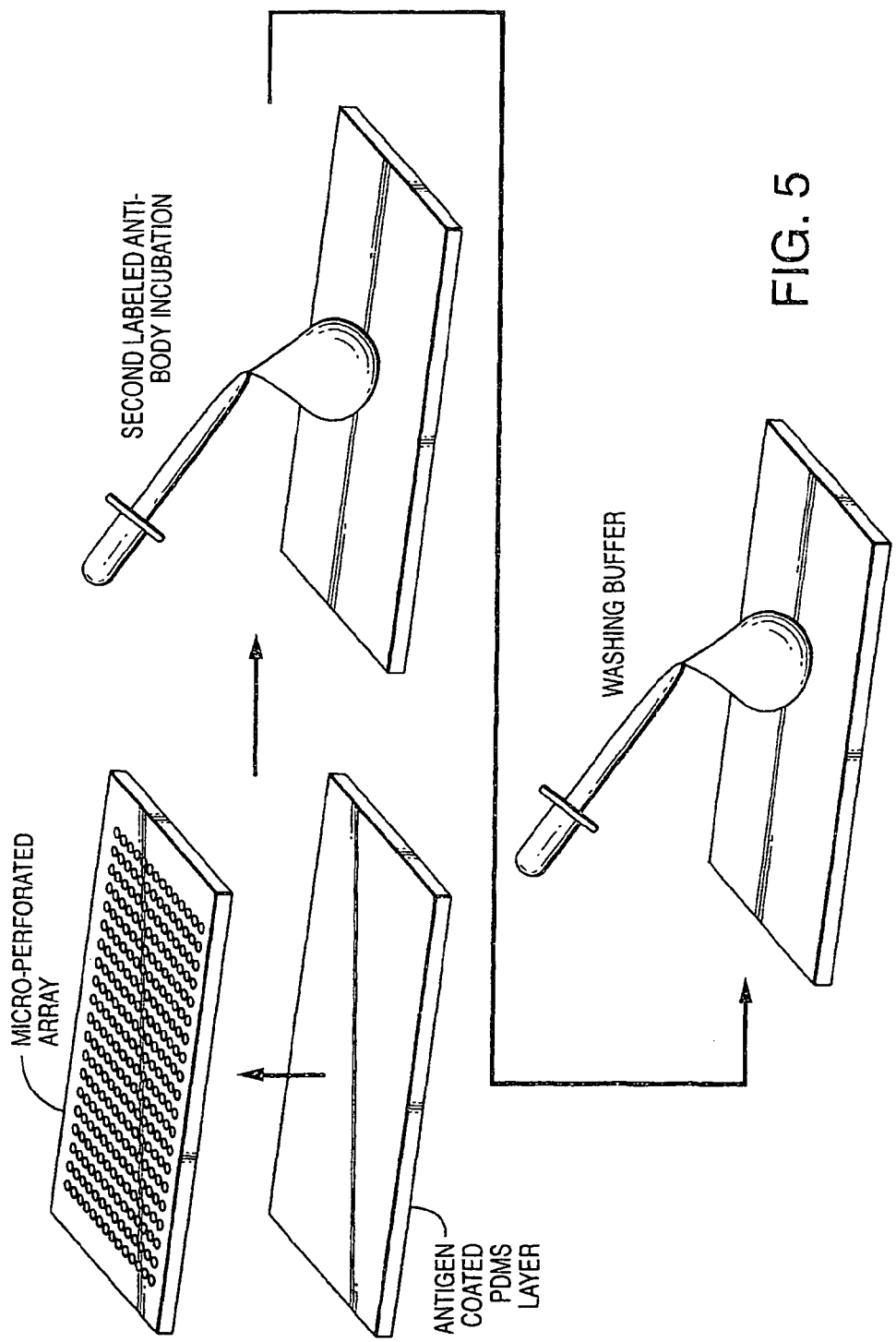
FIG. 5 illustrates one embodiment of a method to select and isolate a sub-population (for example, a cell) from a very high-density micro-pore array.

In one embodiment, the present invention contemplates a method for isolating and selecting a cell within a micro-pore. In one embodiment, the method comprises separating the binding partner-coated solid substrate from the micro-pore array. In one embodiment, the binding partner-coated solid substrate comprises an antigen-primary antibody complex. In one embodiment, the method further comprises incubating the separated binding-partner-coated solid substrate with a secondary labeled anti-tag antibody to detect the antigen-primary antibody complex. In one embodiment, the detected antigen-primary antibody complex forms a detectable spot. See, FIG. 5. In one embodiment, the detectable spot is fluorescent. In one embodiment, the detectable spot is radioactive. In one embodiment, the detectable spot is spin-labeled.

Figure 6:
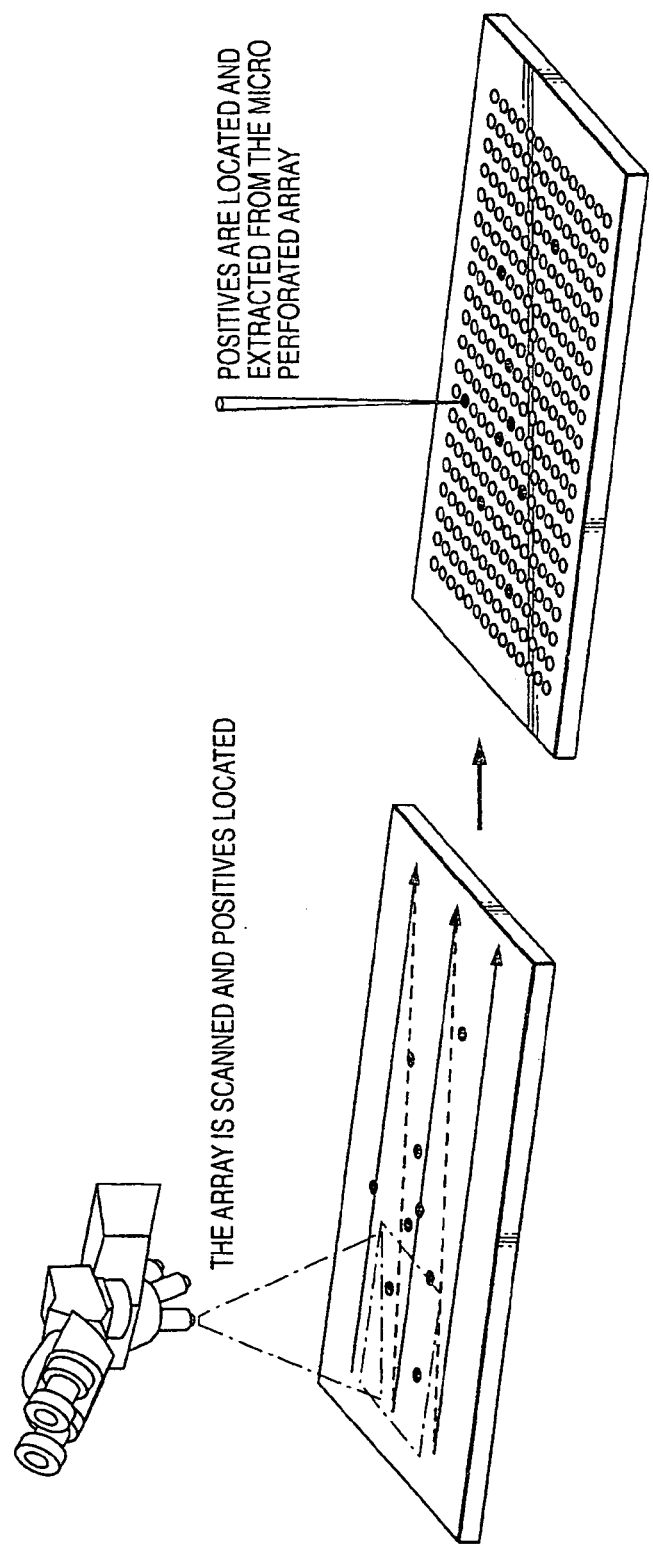
FIG. 6 illustrates one embodiment of a method for scanning and addressing (locating) the positive binding sites (i.e., high intensity spots), thereby allowing subsequent isolating and extraction of cell-specific DNA.

In one embodiment, the solid substrate comprising the labeled antigen-primary antibody complex is scanned to locate high intensity binding spots by spatial addressing. See, FIG. 6. Although it is not necessary to understand the mechanism of an invention, it is believed that the scanning locates the specific micro-pore address comprising cells secreting the compound of interest (i.e., for example, the specific antibody).

In one embodiment, the method further comprises isolating the spatially addressed cells located in the micro-pores corresponding to the high intensity binding spots. In one embodiment, the isolating may be selected from the group comprising pressure ejection, degas driven flow, and/or electrolytic expulsion. In one embodiment, the isolated cell is extracted, cultured and identified for recovery of the cell DNA.

Figure 17:
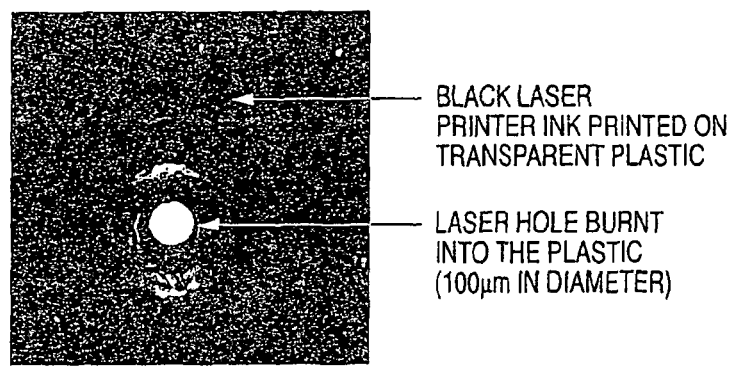
FIG. 17 presents one embodiment of a pressure-based cell selection method. A plastic sheet printed with black laser printer ink was lasered to create a 100 μm diameter laser hole and was placed over the glass array which had been filled with food colorant.
Figure 18:
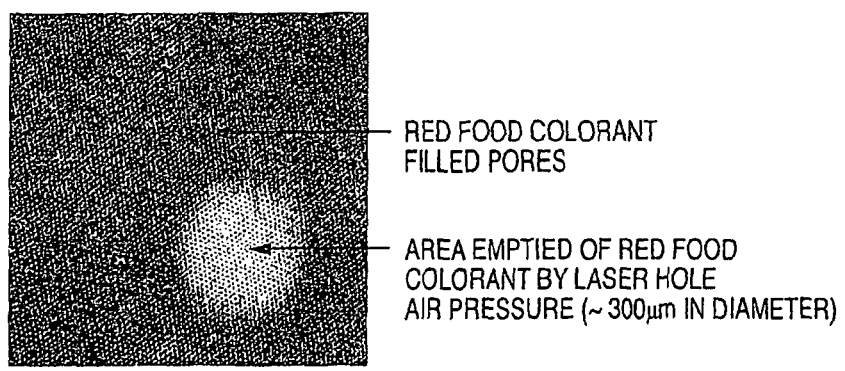
FIG. 18 presents exemplary data showing the removal of food colorant after exposure to air pressure through an ~100 μm hole in a plastic film (plastic transparent sheet with laser printed black area (to absorb the energy from the laser and ablate)). The air pressure removed the colorant almost completely from the pores in a 300 μm area around the laser hole (white area).
Figure 17A:
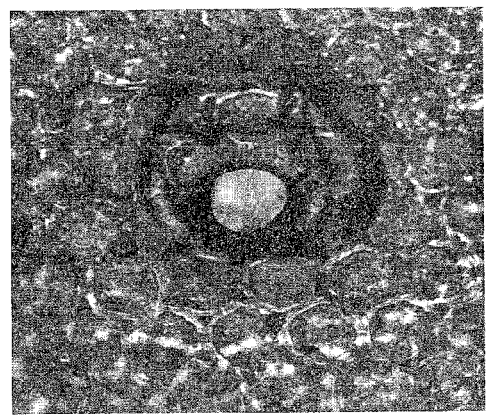
FIG. 17A presents another embodiment of a pressure-based cell selection method. A plastic sheet printed with black laser printer ink was lasered to create a 40 μm diameter laser hole and was placed over the glass array which had been filled with food colorant.

In one embodiment, the method further comprises isolating cells located in the micro-pores by pressure ejection. For example, a separated micro-pore array is covered with a plastic film. In one embodiment, the method further provides a laser capable of making a hole through the plastic film, thereby exposing the spatially addressed micro-pore. See, FIGS. 17 and 17a. In FIGS. 17 and 17A, the bright circular feature in the centre is the 40 μm hole and the other circular features are an imprinted image of the array left on the scotch tape. Subsequently, exposure to a pressure source (i.e., for example, air pressure) expels the contents (i.e., for example, cells) from the spatially addressed micro-pore. See, FIG. 18. In one embodiment, the hole is between approximately 500 μm-1 μm. In one embodiment, the hole is between approximately 100 μm-5 μm. In one embodiment, the hole is between approximately 50 μm-10 μm. In one embodiment, the hole is between 25 μm-15 μm. In one embodiment, the laser is a non-melting laser.

Figure 18A:
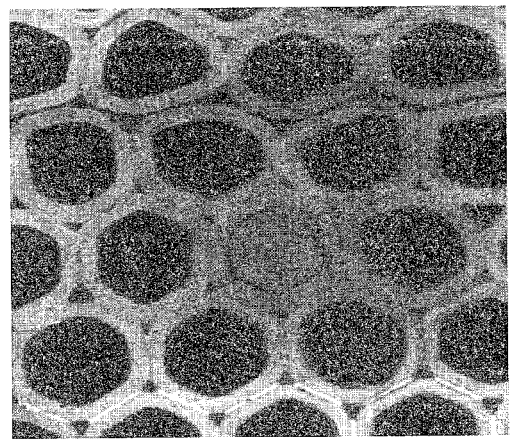
FIG. 18A presents exemplary data showing the removal of food colorant after exposure to air pressure through an ~40 μm hole in Scotch tape. The air pressure removed the colorant almost completely from the pores in a 40 μm area around the laser hole (white area).

FIG. 18A demonstrates single pore removal from a 40 μm pore diameter micropore filter array. A 40 μm diameter micropore filter array was filled with food colourant (dark pores) and the contents of one single pore removed by focussed air pressure through a 40 μm hole in scotch tape that sealed the whole array.

C. Therapeutic Drug Discovery

In one embodiment, the present invention contemplates a method comprising identifying new therapeutic drugs. For example, a solid substrate may be coated with a drug binding partner known to be involved in a disease condition (i.e., for example, a biological receptor and/or enzyme) or a non-immobilized drug binding partner known to be involved in a disease condition is provided. A plurality of cells secreting various compounds suspected of having affinity for the binding partner is then screened using the very high-density micro-pore array. The micro-pores containing the binding partner-compound complexes having the highest affinity are selected for future development.

D. Diagnostic Antibody Discovery

In one embodiment, the present invention contemplates a method comprising identifying diagnostic antibodies. For example, a solid substrate may be coated with a binding partner known to be involved in a disease condition (i.e., for example, an antigen and/or epitope) or a non-immobilized drug binding partner known to be involved in a disease condition is provided. A plurality of cells secreting various antibodies suspected of having affinity for the binding partner is then screened using the very high-density micro-pore array. The micro-pores containing the binding partner-antibody complexes having the highest affinity are selected for future development.

E. Protein-Protein Interaction Studies

In one embodiment, the present invention contemplates a method comprising identifying protein-protein interactions. For example, a solid substrate may be coated with a binding partner known to be involved in a disease condition (i.e., for example, a protein and/or peptide) or a non-immobilized drug binding partner known to be involved in a disease condition is provided. A plurality of cells secreting various proteins and/or peptides suspected of having affinity for the binding partner is then screened using the very high-density micro-pore array. The micro-pores containing the binding partner-protein or peptide complexes having the highest affinity are selected for future development.

F. Protein-Nucleic Acid Interaction Studies

In one embodiment, the present invention contemplates a method comprising identifying protein-nucleic acid interactions. For example, a solid substrate may be coated with a binding partner known to be involved in a disease condition (i.e., for example, a deoxyribonucleic acid and/or a ribonucleic acid and/or a SOMAmer and/or a Apatamer) or a non-immobilized drug binding partner known to be involved in a disease condition is provided. A plurality of cells secreting various proteins and/or peptides suspected of having affinity for the binding partner is then screened using the very high-density micro-pore array. The micro-pores containing the binding partner-nucleic acid complexes having the highest affinity are selected for future development.

G. Protein-Carbohydrate Interaction Studies

In one embodiment, the present invention contemplates a method comprising identifying protein-carbohydrate interactions. For example, a solid substrate may be coated with a binding partner known to be involved in a disease condition (i.e., for example, an oligosaccharide, and liposaccharide, or a proteosaccharide) or a non-immobilized drug binding partner known to be involved in a disease condition is provided. A plurality of cells secreting various lectins, proteins and/or peptides suspected of having affinity for the binding partner is then screened using the very high-density micro-pore array. The micro-pores containing the binding partner-carbohydrate complexes having the highest affinity are selected for future development.

V. Kits

In another embodiment, the present invention contemplates a kit comprising: a first container comprising an array of micro-pores, wherein the internal diameter of micro-pores range between approximately 1.0 micrometers and 500 micrometers; and a second container comprising at least one binding partner. In one embodiment the second container comprises a solid substrate comprising said at least one binding partner, the solid substrate being capable of reversible attachment to the array of micro-pores.

In another embodiment, the present invention contemplates kits for the practice of the methods of this invention. The kits preferably include one or more containers containing a micro-pore array comprising a plurality of fused capillary fibers that are not coated with a plurality of binding partners. The kit can optionally include a solid substrate comprising a plurality of binding partners. The kit can optionally include a plurality of labeled reagents capable of detecting a variety of binding partner-biological compound complexes. The kit can optionally include a solution comprising a biological cell comprising a recombinant protein. The kits may also optionally include appropriate systems (e.g. opaque containers) or stabilizers (e.g. antioxidants) to prevent degradation of the reagents by light or other adverse conditions.

The kits may optionally include instructional materials containing directions (i.e., protocols) providing for the use of the micro-pore array in the detection of various biological compounds that are secreted from a biological cell. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

VI. Antibodies

The present invention provides recombinant antibodies (i.e., for example, polyclonal or monoclonal). In one embodiment, the present invention provides monoclonal antibodies that specifically bind to a variety of antigens and/or epitopes. These antibodies find use in the detection methods described above.

An antibody against a protein of the present invention may be any monoclonal or polyclonal antibody, as long as it can recognize the protein. Antibodies can be produced by using a protein of the present invention as the antigen according to a conventional antibody or antiserum preparation process.

The present invention contemplates the use of both monoclonal and polyclonal antibodies. Any suitable method may be used to generate the antibodies used in the methods and compositions of the present invention, including but not limited to, those disclosed herein. For example, for preparation of a monoclonal antibody, protein, as such, or together with a suitable carrier or diluent is administered to an animal (e.g., a mammal) under conditions that permit the production of antibodies. For enhancing the antibody production capability, complete or incomplete Freund's adjuvant may be administered. Normally, the protein is administered once every 2 weeks to 6 weeks, in total, about 2 times to about 10 times. Animals suitable for use in such methods include, but are not limited to, primates, rabbits, dogs, guinea pigs, mice, rats, sheep, goats, etc.

For preparing monoclonal antibody-producing cells, an individual animal whose antibody titer has been confirmed (e.g., a mouse) is selected, and 2 days to 5 days after the final immunization, its spleen or lymph node is harvested and antibody-producing cells contained therein are fused with myeloma cells to prepare the desired monoclonal antibody producer hybridoma. Measurement of the antibody titer in antiserum can be carried out, for example, by reacting the labeled protein, as described hereinafter and antiserum and then measuring the activity of the labeling agent bound to the antibody. The cell fusion can be carried out according to known methods, for example, the method described by Koehler and Milstein (Nature 256:495 [1975]). As a fusion promoter, for example, polyethylene glycol (PEG) or Sendai virus (HVJ), preferably PEG is used.

Examples of myeloma cells include NS-1, P3U1, SP2/0, AP-1 and the like. The proportion of the number of antibody producer cells (spleen cells) and the number of myeloma cells to be used is preferably about 1:1 to about 20:1. PEG (preferably PEG 1000-PEG 6000) is preferably added in concentration of about 10% to about 80%. Cell fusion can be carried out efficiently by incubating a mixture of both cells at about 20° C. to about 40° C., preferably about 30° C. to about 37° C. for about 1 minute to 10 minutes.

Various methods may be used for screening for a hybridoma producing the antibody (e.g., against a tumor antigen or autoantibody of the present invention). For example, where a supernatant of the hybridoma is added to a solid phase (e.g., microplate) to which antibody is adsorbed directly or together with a carrier and then an anti-immunoglobulin antibody (if mouse cells are used in cell fusion, anti-mouse immunoglobulin antibody is used) or Protein A labeled with a radioactive substance or an enzyme is added to detect the monoclonal antibody against the protein bound to the solid phase. Alternately, a supernatant of the hybridoma is added to a solid phase to which an anti-immunoglobulin antibody or Protein A is adsorbed and then the protein labeled with a radioactive substance or an enzyme is added to detect the monoclonal antibody against the protein bound to the solid phase.

Selection of the monoclonal antibody can be carried out according to any known method or its modification. Normally, a medium for animal cells to which HAT (hypoxanthine, aminopterin, thymidine) are added is employed. Any selection and growth medium can be employed as long as the hybridoma can grow. For example, RPMI 1640 medium containing 1% to 20%, preferably 10% to 20% fetal bovine serum, GIT medium containing 1% to 10% fetal bovine serum, a serum free medium for cultivation of a hybridoma (SFM-101, Nissui Seiyaku) and the like can be used. Normally, the cultivation is carried out at 20° C. to 40° C., preferably 37° C. for about 5 days to 3 weeks, preferably 1 week to 2 weeks under about 5% $CO_2$ gas. The antibody titer of the supernatant of a hybridoma culture can be measured according to the same manner as described above with respect to the antibody titer of the anti-protein in the antiserum.

Separation and purification of a monoclonal antibody can be carried out according to the same manner as those of conventional polyclonal antibodies such as separation and purification of immunoglobulins, for example, salting-out, alcoholic precipitation, isoelectric point precipitation, electrophoresis, adsorption and desorption with ion exchangers (e.g., DEAE), ultracentrifugation, gel filtration, or a specific purification method wherein only an antibody is collected with an active adsorbent such as an antigen-binding solid phase, Protein A or Protein G and dissociating the binding to obtain the antibody.

Polyclonal antibodies may be prepared by any known method or modifications of these methods including obtaining antibodies from patients. For example, a complex of an immunogen (an antigen against the protein) and a carrier protein is prepared and an animal is immunized by the complex according to the same manner as that described with respect to the above monoclonal antibody preparation. Material containing the antibody is recovered from the immunized animal and the antibody is separated and purified.

As to the complex of the immunogen and the carrier protein to be used for immunization of an animal, any carrier protein and any mixing proportion of the carrier and a hapten can be employed as long as an antibody against the hapten, which is crosslinked on the carrier and used for immunization, is produced efficiently. For example, bovine serum albumin, bovine cycloglobulin, keyhole limpet hemocyanin, etc. may be coupled to an hapten in a weight ratio of about 0.1 part to about 20 parts, preferably, about 1 part to about 5 parts per 1 part of the hapten.

In addition, various condensing agents can be used for coupling of a hapten and a carrier. For example, glutaraldehyde, carbodiimide, maleimide activated ester, activated ester reagents containing thiol group or dithiopyridyl group, and the like find use with the present invention. The condensation product as such or together with a suitable carrier or diluent is administered to a site of an animal that permits the antibody production. For enhancing the antibody production capability, complete or incomplete Freund's adjuvant may be administered. Normally, the protein is administered once every 2 weeks to 6 weeks, in total, about 3 times to about 10 times.

The polyclonal antibody is recovered from blood, ascites and the like, of an animal immunized by the above method. The antibody titer in the antiserum can be measured according to the same manner as that described above with respect to the supernatant of the hybridoma culture. Separation and purification of the antibody can be carried out according to the same separation and purification method of immunoglobulin as that described with respect to the above monoclonal antibody.

The protein used herein as the immunogen is not limited to any particular type of immunogen. For example, a protein expressed resulting from a virus infection (further including a gene having a nucleotide sequence partly altered) can be used as the immunogen. Further, fragments of the protein may be used. Fragments may be obtained by any methods including, but not limited to expressing a fragment of the gene, enzymatic processing of the protein, chemical synthesis, and the like.

VII. Detection Methodologies

A. Detection of Nucleic Acids mRNA expression may be measured by any suitable method, including but not limited to, those disclosed below.

In some embodiments, RNA is detection by Northern blot analysis. Northern blot analysis involves the separation of RNA and hybridization of a complementary labeled probe.

In other embodiments, RNA expression is detected by enzymatic cleavage of specific structures (INVADER assay, Third Wave Technologies; See e.g., U.S. Pat. Nos. 5,846,717, 6,090,543; 6,001,567; 5,985,557; and 5,994,069; each of which is herein incorporated by reference). The INVADER assay detects specific nucleic acid (e.g., RNA) sequences by using structure-specific enzymes to cleave a complex formed by the hybridization of overlapping oligonucleotide probes.

In still further embodiments, RNA (or corresponding cDNA) is detected by hybridization to an oligonucleotide probe. A variety of hybridization assays using a variety of technologies for hybridization and detection are available. For example, in some embodiments, TaqMan assay (PE Biosystems, Foster City, Calif.; See e.g., U.S. Pat. Nos. 5,962,233 and 5,538,848, each of which is herein incorporated by reference) is utilized. The assay is performed during a PCR reaction. The TaqMan assay exploits the 5'-3' exonuclease activity of the AMPLITAQ GOLD DNA polymerase. A probe consisting of an oligonucleotide with a 5'-reporter dye (e.g., a fluorescent dye) and a 3'-quencher dye is included in the PCR reaction. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In yet other embodiments, reverse-transcriptase PCR(RT-PCR) is used to detect the expression of RNA. In RT-PCR, RNA is enzymatically converted to complementary DNA or "cDNA" using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 (each of which is herein incorporated by reference) is utilized.

B. Sequencing Of Nucleic Acids

The method most commonly used as the basis for nucleic acid sequencing, or for identifying a target base, is the enzymatic chain-termination method of Sanger. Traditionally, such methods relied on gel electrophoresis to resolve, according to their size, wherein nucleic acid fragments are produced from a larger nucleic acid segment. However, in recent years various sequencing technologies have evolved which rely on a range of different detection strategies, such as mass spectrometry and array technologies.

One class of sequencing methods assuming importance in the art are those which rely upon the detection of PPi release as the detection strategy. It has been found that such methods lend themselves admirably to large-scale genomic projects or clinical sequencing or screening, where relatively cost-effective units with high throughput are needed.

Methods of sequencing based on the concept of detecting inorganic pyrophosphate (PPi) which is released during a polymerase reaction have been described in the literature for example (WO 93/23564, WO 89/09283, WO98/13523 and WO 98/28440). As each nucleotide is added to a growing nucleic acid strand during a polymerase reaction, a pyrophosphate molecule is released. It has been found that pyrophosphate released under these conditions can readily be detected, for example enzymatically e.g. by the generation of light in the luciferase-luciferin reaction. Such methods enable a base to be identified in a target position and DNA to be sequenced simply and rapidly whilst avoiding the need for electrophoresis and the use of labels.

At its most basic, a PPi-based sequencing reaction involves simply carrying out a primer-directed polymerase extension reaction, and detecting whether or not that nucleotide has been incorporated by detecting whether or not PPi has been released. Conveniently, this detection of PPi-release may be achieved enzymatically, and most conveniently by means of a luciferase-based light detection reaction termed ELIDA (see further below).

It has been found that dATP added as a nucleotide for incorporation, interferes with the luciferase reaction used for PPi detection. Accordingly, a major improvement to the basic PPi-based sequencing method has been to use, in place of dATP, a dATP analogue (specifically dATP.alpha.s) which is incapable of acting as a substrate for luciferase, but which is nonetheless capable of being incorporated into a nucleotide chain by a polymerase enzyme (WO98/13523).

Further improvements to the basic PPi-based sequencing technique include the use of a nucleotide degrading enzyme such as apyrase during the polymerase step, so that unincorporated nucleotides are degraded, as described in WO 98/28440, and the use of a single-stranded nucleic acid binding protein in the reaction mixture after annealing of the primers to the template, which has been found to have a beneficial effect in reducing the number of false signals, as described in WO00/43 540.

C. Detection of Protein

In other embodiments, gene expression may be detected by measuring the expression of a protein or polypeptide. Protein expression may be detected by any suitable method. In some embodiments, proteins are detected by immunohistochemistry. In other embodiments, proteins are detected by their binding to an antibody raised against the protein. The generation of antibodies is described below.

Antibody binding may be detected by many different techniques including, but not limited to, (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled.

In some embodiments, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a prognosis based on the presence or absence of a series of proteins corresponding to cancer markers is utilized.

In other embodiments, the immunoassay is as described in U.S. Pat. Nos. 5,599,677 and 5,672,480; each of which is herein incorporated by reference.

D. Remote Detection Systems

In some embodiments, a computer-based analysis program is used to translate the raw data generated by the detection assay (e.g., the presence, absence, or amount of a given marker or markers) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, wherein the information is provided to medical personal and/or subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw expression data, the prepared format may represent a diagnosis or risk assessment for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease.

E. Detection Kits

In other embodiments, the present invention provides kits for the detection and characterization of proteins and/or nucleic acids. In some embodiments, the kits contain antibodies specific for a protein expressed from a gene of interest, in addition to detection reagents and buffers. In other embodiments, the kits contain reagents specific for the detection of mRNA or cDNA (e.g., oligonucleotide probes or primers). In preferred embodiments, the kits contain all of the components necessary to perform a detection assay, including all controls, directions for performing assays, and any necessary software for analysis and presentation of results.

EXPERIMENTAL

Example I

Glass Pore Array Feasibility Study

A fused silica micro-pore array was obtained having regularly spaced micro-pores with a 10 μm diameter, and a 66% total open area, thus there is a very high density distribution of micro-pores (i.e., for example, between approximately 3 and 5 million). See, FIGS. 7A and 7B.

Example 1a: Bacteriophage assay: A PDMS layer (solid substrate) was first coated with bacteriophage particles, followed by placement of the above-mentioned micro-pore array (array having regularly spaced micro-pores with a 10 μm diameter and a 66% total open area) on the PDMS layer. Different regions of the assembled micro-pore testbed array were loaded with solutions comprising different concentrations of biotin labeled anti-phage antibodies. Alternatively, the micro-pore array can be loaded with the biotin labeled anti-phage antibody solution and then placed on the PDMS layer. It is preferred that the micro-pore testbed array is assembled by pacing the micro-pore array on the PDMS layer, after which the biotin labeled anti-phage antibody solution is applied onto the micro-pore testbed array.

Figure 8:
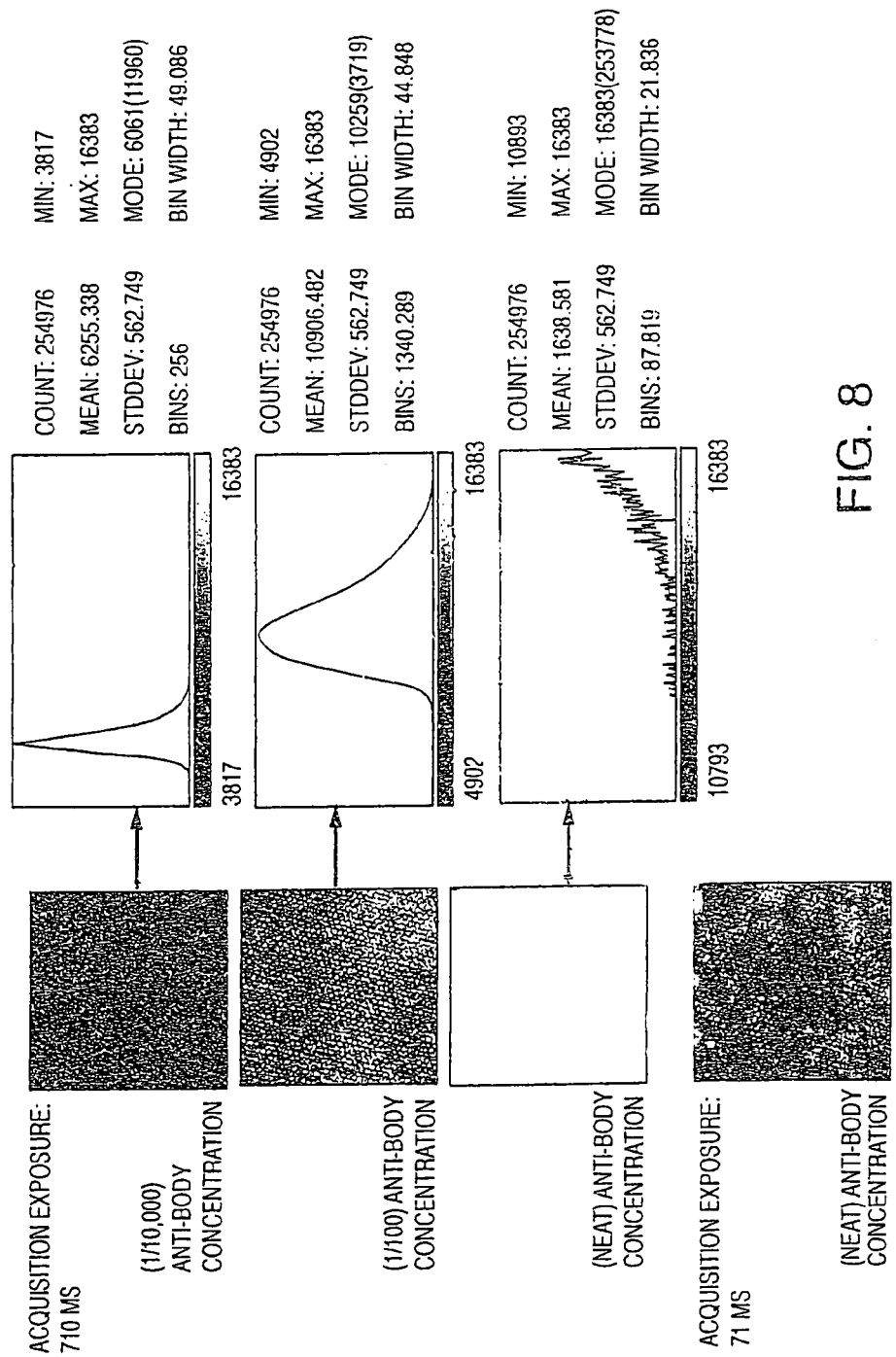
FIG. 8 presents exemplary data showing a phage—biotin labeled anti-phage—FITC streptavidin assay that reveals a signal that is dependent on the antibody concentration.
Figure 8A:
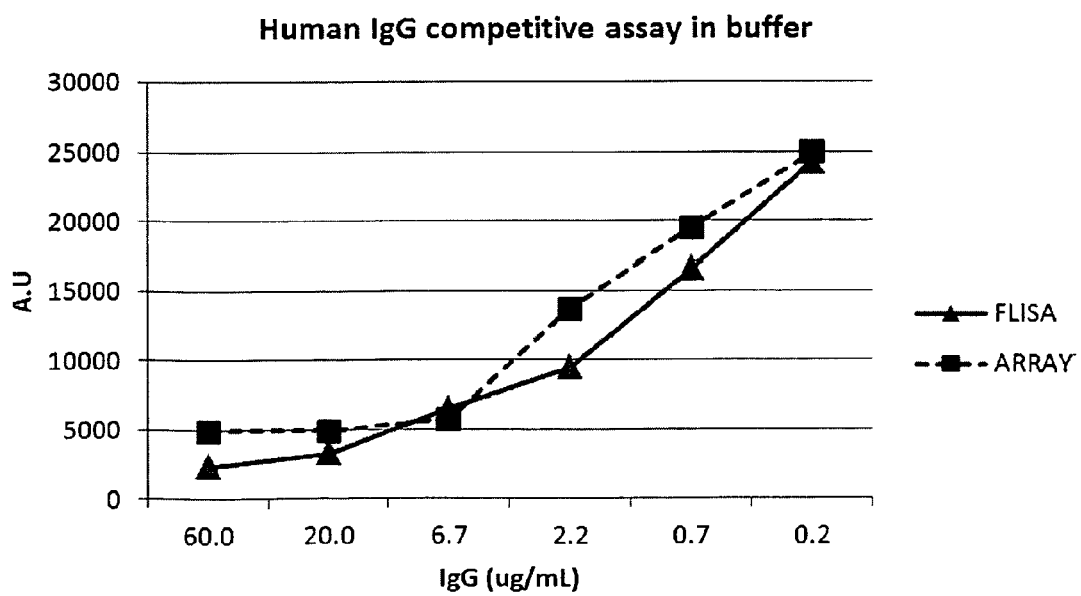
FIG. 8A presents exemplary data showing immunoassay performance on the micropore filter array.

The micro-pore array was separated from the PDMS layer and the PDMS layer was stained with FITC labeled Extravidin, thereby selectively staining the biotin-labeled anti-phage antibodies. FITC signals were seen to vary in proportion with the phage-bound antibody concentration. See, FIG. 8. Micropore filter array and microtitre plate immunoassay comparison with human IgG (antigen) and goat anti-human IgG Cy5-labelled polyclonal antibody. See FIG. 8a.

Example 1b: Human IgG competitive immunoassay: A competitive assay was performed under identical conditions on both a Nunc microtitre plate and on the assembled micro-pore testbed array comprising PDMS sealed micropore filter array. Human IgG was coated on the surface and decreasing concentrations of human IgG in solution mixed 1:1 (v:v) with a set concentration of goat anti-human IgG Cy5-labelled antibody.

The aim of this example is to show that antibody-antigen binding interactions can be performed in the micropore array and that the immunoassay sensitivity the array assay is comparable with that of a standard microtiter plate assay.

Materials:
Hamamatsu capillary plate filter (Hamamatsu J5022-16)
PDMS (Sylgard 184 Silicone Elastomer Kit, Dow Corning order No: (400)000104984061)
Bovine Serum Albumin, BSA (Sigma A9418)
Bacteriophage particles (New England Biolabs M13KO7 helper phage, N0315)
Biotin labeled anti-fd bacteriophage antibody (Sigma B2661)
Extravidin-FITC (Sigma E2761)
Human IgG (Biomeda Corp Cat No: MS 143)
Goat anti-human IgG polyclonal antibody, Cy5 labeled (Biomeda Corp Cat No: SJ15147-C)

Methods:
Example 1a: Bacteriophage Assay:
  The PDMS solid substrate was prepared by mixing 10 parts of elastomer with 1 part curing agent followed by curing at 60° C. for 2 hours. PDMS slabs were prepared to between 3 and 5 mm in thickness and cut to size as needed so that the micro-pore array could be placed on top.
  The PDMS slab was coated with M13KO7 helper phage at $1 \times 10^9$ phage/mL in PBS for 1 hour at 37° C. after which it was submerged in 10 mL PBS containing 3% (w/v) BSA for 1 hour at 37° C.
  The coated and blocked PDMS slab was washed with 5 mL of PBS and 5 mL of ultrapure water and subsequently air dried and degassed by placing the slab in a vacuum chamber consisting of a plastic desiccator linked up to vacuum tap at approximately 1 to $1 \times 10^{-3}$ Torr for 45 minutes.
  The micro-pore array (glass capillary array) was placed on top of the degassed PDMS slab and pressed tightly against the slab to form a reversible liquid-tight seal, preventing any possible leakage.
  Immediately, three microliters of neat biotinylated anti-fd bacteriophage antibody, 1/100 antibody diluted in PBS and 1/10,000 dilution of antibody diluted in PBS were added to 3 different sections of the glass micropore array using a micropipette and spread evenly over the micropores. Spreading the liquid after placing on to the array prevents the 'halo effect (see FIGS. 20, 21 and 22A-C) that can occur due to surface tension forces that are present when the sample is left as a droplet on the array.
  The PDMS slab/micropore array was incubated at 37° C. for 1 hour.
  To visualize binding on the PDMS slab, the glass array was manually peeled off and the PDMS slab washed with 10 mL of PBST (PBS with 0.05% Tween 20). Eight hundred microliters of a 1/50 dilution of Extravidin FITC was placed on top of the PDMS slab covering the analysis area. After incubation for 1 hour at 37° C., the slab was washed with 20 mL of PBST, air dried and visualized using a fluorescent microscope with FITC filter.

Example 1b: Human IgG Competitive Immunoassay:

Eight hundred microliters of a five micrograms per mL of human IgG diluted in PBS was used to coat the surface of a PDMS slab. 100 µL/well of the five micrograms per mL of human IgG diluted in PBS was used to coat the wells of a black Nunc Maxisorb 96 well microtiter plate, Each were incubated for 1 hour at 37° C.

Both the PDMS slab and the microtiter plate were blocked with 3% (w/v) BSA in PBS (200 µL/well for the microtiter plate while the slab was submerged in 5 mL) for 1 hour at 37° C.

Goat anti-human IgG Cy5-labelled polyclonal antibody diluted 1/1000 in PBS was mixed 1:1 (v/v) with decreasing concentrations of human IgG (final concentrations ranged from 60 to 0.2 micrograms per mL) and subsequently added to wells of the microtiter plate (100 µL/well) and to specific regions of the micro-pore array (3 µL of each dilution added to the array).

The array was then immediately placed on top of the degassed antigen coated and blocked PDMS slab and reversibly sealed by applying manual pressure.

Both the array and the microtiter plate were incubated at 37° C. for 1 hour before being washed with PBST (20 mL PBST was passed over the slab while each well of the microtiter plate was washed four times).

The fluorescent intensity from bound Cy5 labeled antibody in the microtiter plate was measured using a Tecan Safire2 plate reader (Ex. 650, Em. 670) while the fluorescent intensity on the PDMS slab was measured using a PerkinElmer microarray scanner with Cy5 filter Conclusion: The experiments described here show that, not only can an immunoassay be performed in the glass micropore array reversibly attached to PDMS but, despite the extremely low volume per pore (78 µL), excellent immunoassay sensitivity correlation with the standard 96 well plate format is achieved.

Example II

Micro-Pore Cell Viability

This example demonstrates the viability and expression capability of green fluorescent protein-expressing *E. coli* incubated in a micro-pore array.

Figure 9A:
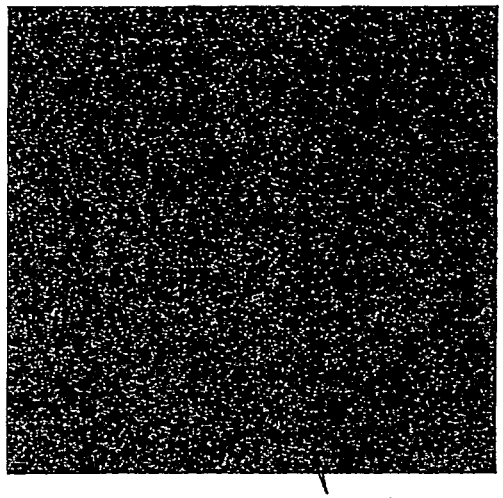
Figure 9B:
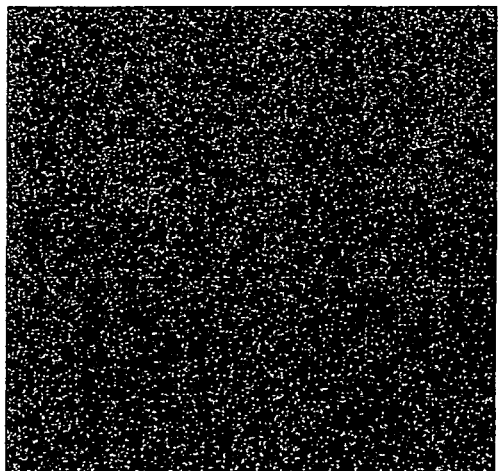

Example IIa: Verification that *E. coli* cells can enter the micro-pores of the array: *E. coli* cells were loaded onto a micro-pore testbed array comprising the micro-pore array as described in Example I placed on an uncoated and unblocked PDMS layer, the micro-pore testbed array then being incubated for 1.5 hrs. The PDMS layer was then separated whereby the data show that *E. coli* cells remained on the PDMS post culture and could be visualized on the PDMS surface using a fluorescent microscope. See, FIGS. 9A and B.

Example IIa: Verification that *E. coli* cells can express recombinant protein in the micro-pores: *E coli* cell viability in the micro-pore testbed array was demonstrated with a GFP induction assay, where non-GFP *E. coli* cells were induced to produce GFP when loaded into the micro-pores by mixing the cells with an induction medium. GFP fluorescence within each well was recorded in real time. Heat inactivated cells (10 minutes at 70° C.) were used as a negative control. See, FIG. 10.

Aim: To show that *E. coli* cells can enter the 10 µm diameter pores and express recombinant protein in the micro-pores Materials:

*E. coli* Rosetta cells (Novagen) transformed with a pET28b plasmid (Novagen) containing the gene encoding for enhanced green fluorescent protein (sequence identical to eGFP from pEGFP accession number U76561)

Fluorescent microscope with automated stage and camera (OLYMPUS IX81)

Hamamatsu capillary plate filter (Hamamatsu J5022-16)

PDMS (Sylgard 184 Silicone Elastomer Kit, Dow Corning order No: (400)000104984061)

Methods:

Example IIa: Verification that *E. coli* Cells can Enter the Micro-Pores:

*E. coli* Rosetta cells transformed with a pET28b plasmid containing the gene encoding for enhanced green fluorescent protein were grown in 2×TY media until an O.D.600 of 0.5 was reached at which time IPTG (Fisher BPE-1755-10) was added to a final concentration of 1 mM. The culture was further incubated for 4 hours at 30° C. with agitation at 200 rpm.

The culture was then diluted 1/100 in 2×TY media and 5 µL of neat and 1/100 culture added to the micropore array of Example I reversibly bound to an uncoated and unblocked degassed PDMS slab. The array was incubated for 1.5 hours at 37° C. before the array was gently removed and the PDMS visualized using a fluorescent microscope.

Example IIa: Verification that *E. coli* Cells can Express Recombinant Protein in the Micro-Pores:

*E. coli* Rosetta cells transformed with a pET28b plasmid containing the gene encoding for enhanced green fluorescent protein were grown in 2×TY media until an O.D.600 of 0.5 was reached at which time the cultures were pelleted by centrifugation (3300 g for 10 minutes) and the pellet resuspended in fresh 2×TY media to the initial culture volume.

Five milliliters of culture was transferred to two sterile universal tubes and one (positive culture) was kept at 37° C. for 10 minutes and the other (negative culture) was placed in a 70° C. water bath for 10 minutes.

After 10 minutes, IPTG (Fisher BPE-1755-10) was added to a final concentration of 1 mM to each tube, mixed by inverting and 5 µL of each culture added to separate regions of a 10 µm diameter micro-pore array.

The micro-pore array was reversibly attached to an unmodified PDMS slab and cultured in an incubation chamber attached to an automated fluorescent microscope for 4 hours at 37° C.

Figure 10:
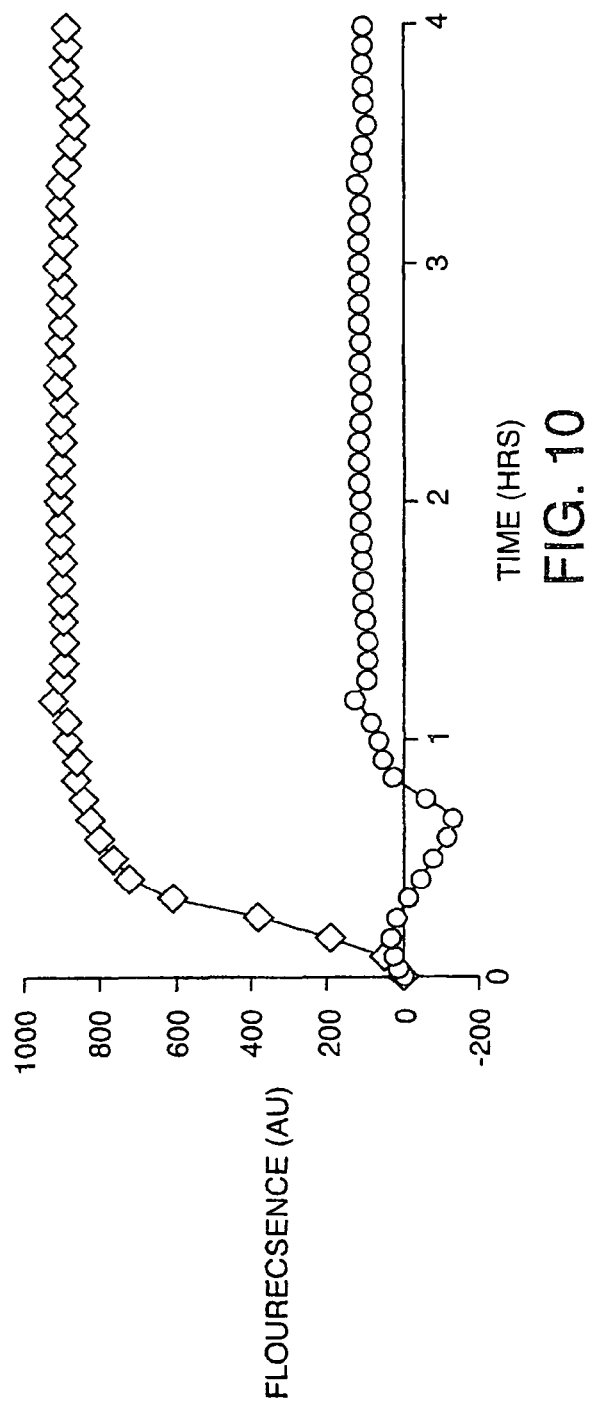
FIG. 10 presents exemplary real time fluorescence data from cells induced to produce GFP in a micro-pore testbed array (open diamonds). Negative control, heat inactivated cells demonstrated no production of GFP (open squares).
Figure 10B:
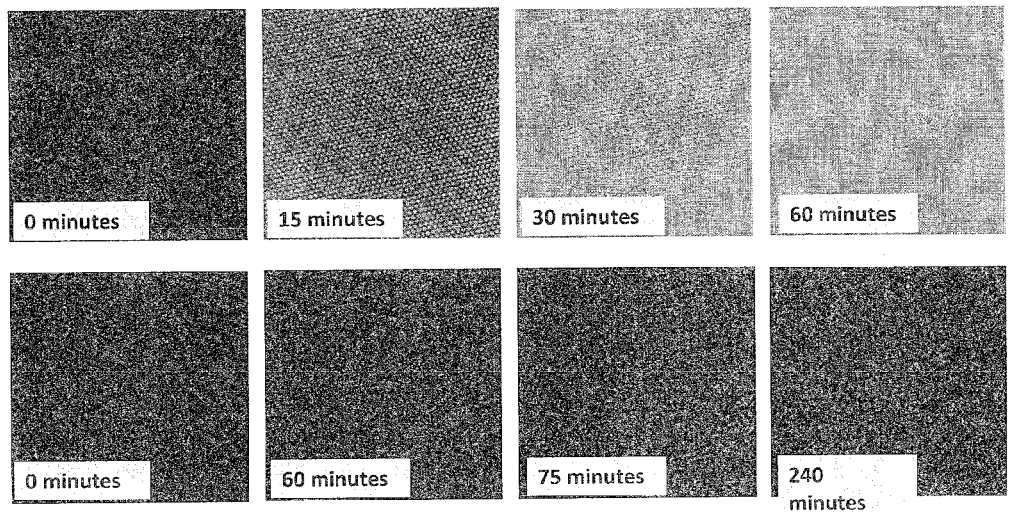
FIG. 10B presents exemplary data showing visualisation of fluorescent images from the positive induced E. coli (top four images) and negative heat inactivated E. coli (bottom four images) cells in the array. The fluorescent intensity of each area taken every 5 minutes is represented in FIG. 10.

The microscope with automated stage was programmed to take images of each culture region every 5 minutes. The intensity of the fluorescence emitted from the expressed GFP from both cultures is shown in FIG. 10 and exemplary frames are visualized in FIG. 10B.

Conclusion: *E. coli* cells were easily loaded into the 10 µm diameter micropore array and expressed an abundance of recombinant GFP. Expression of GFP from one single micropore from the heat-killed culture indicates that one cell (high probability that only one cell survived as no other pore contained cells that survived) survived and this could be easily and clearly detected.

Example III

Antibody Secretion from *E coli* Cells

This example demonstrates that cells can secrete (i.e., leak) antibodies into a culture media such that binding can occur at an antigen coated solid surface.

Example IIIa

Two antibody clones (anti-Halofuginone (HFG) scFv and anti-prostate specific antigen (PSA) scFv) were grown in micro-pores coated with HFG-Transferin, PSA and BSA. Both clones were expected to only bind their cognate antigens and not to the other two surfaces. In addition, the anti-HFG clones were expressed as both soluble antibody and on the surface of phage to evaluate the effects of phage particles.

All 3 clones (soluble and phage anti-HFG and soluble anti-PSA) were also grown in 20 mL tubes overnight and added to a microtiter plate the following day and incubated for 1 hour. Similar results would have been expected following incubation on a micro-pore test bed array.

Figure 11:
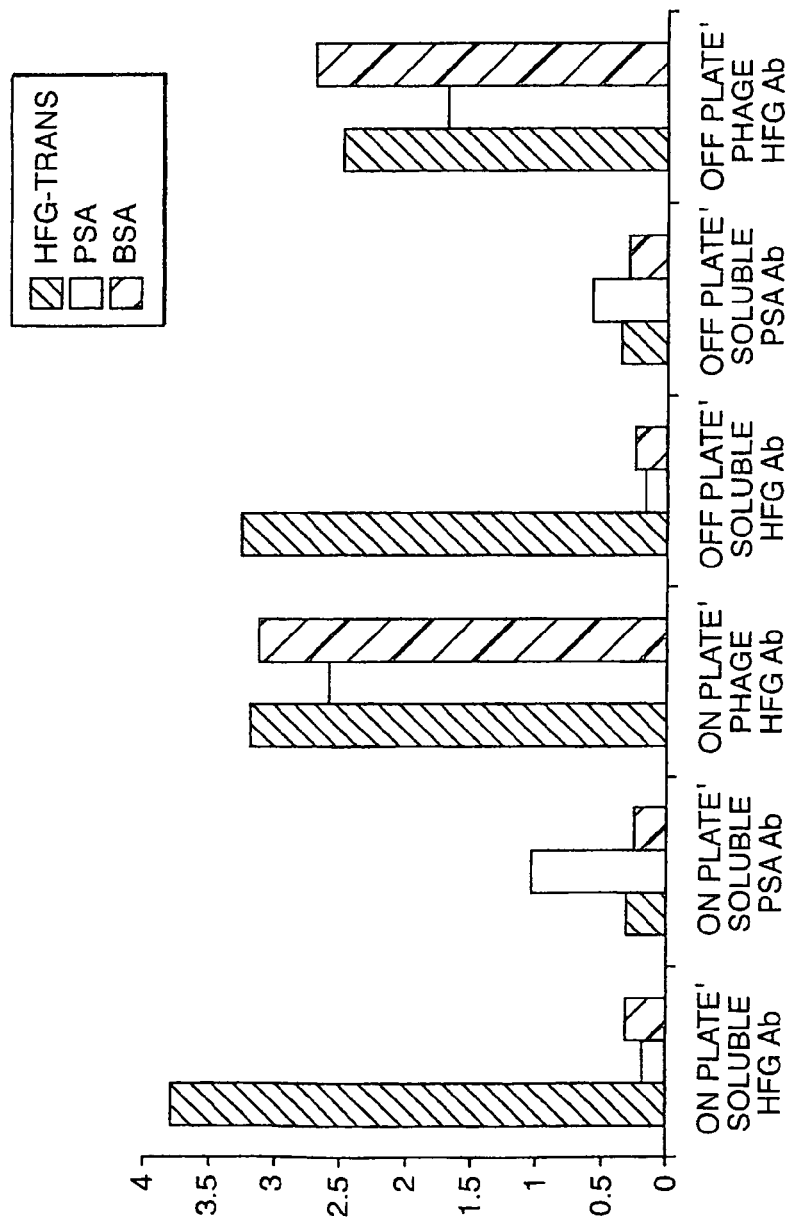
FIG. 11 presents exemplary data of antibody secretion by IPTG induction in E. coli clones grown on an ELISA plate demonstrating improved specificity and reduced background in comparison to phage display technology.

The results showed that a larger antigen specific signal was observed when soluble antibody was produced from culturing on the microtiter plate as compared to that of the same clones grown in conventional test tubes. See, FIG. 11.

Further, the scFv phage display was observed to have a high degree of non-specific binding. In fact, during a normal screening run, an scFv antibody clone would probably not be selected due to the high non-specific binding which is totally eliminated when the antibody is expressed in soluble form.

Example IIIb: Analysis of *E. coli* cells harbouring scFv antibody genes to C-reactive protein (CRP) and cardiac Troponin I (cTnI): *E. coli* cultures containing scFv genes were added to different sections of a micro-pore array (10 μm pores) and cultured for 24 hours. Cells propagated and expressed scFv antibody fragments into the media that could interact with their cognate antigen that was pre-coated on the PDMS surface (column 1, labelled Coated-Cells). See FIG. 25.

The same cultures were also added to parts of the array which was not coated with antigen (Non-coated Cells, column 3) and media added to both coated and non-antigen coated PDMS section through the array (columns 2 and 4).

Figure 25:
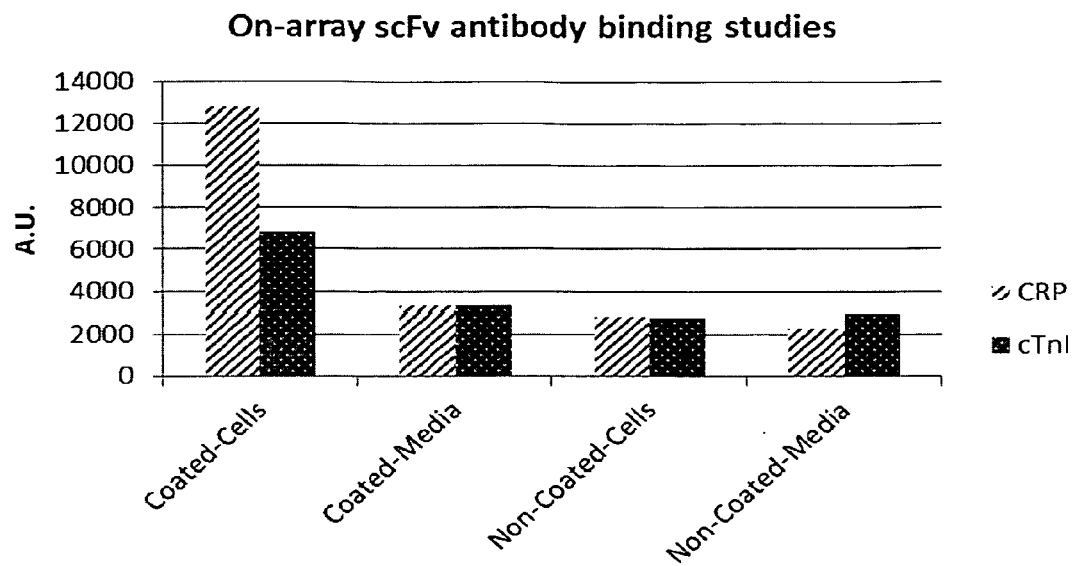

FIG. 25 demonstrates that specific recombinant antibody response can be detected when cultured in the array.

Aim: To show that *E. coli* cells expressing recombinant single chain fragment variable (scFv) antibodies secrete/leak antibody into the media without the need for secretion signals and this antibody can be detected when bound to coated solid support.

Materials: Example IIIa: On Plate Culture of Antibodies and Subsequent Detection of Expressed Antibody
Antigens:
PSA (Lee Biosolutions, Missouri, USA, Cat. No. 497-11)
Halofuginone-BTG (was purchased from Chris Elliot, The Queen's University of Belfast, Northern Ireland)
CRP (Life Diagnostics Inc, PA, USA. Cat. No. 8000)
cTnI (Life Diagnostics Inc, PA, USA. Cat. No. 1210)
Antibodies—Examples IIIa and IIIb:

Recombinant avian scFv antibodies were developed and selected as described herein. RNA was extracted from the spleens and bone marrow of two chickens immunised with target analyte in TRI—Reagent and first-strand cDNA synthesis performed using the Superscript III kit (Invitrogen). Antibody variable heavy and light chain genes were amplified using the primer sets described by Andris-Widhopf and co-workers ("Methods for the generation of chicken monoclonal antibody fragments by phage display", Andris-WidhopfJ, Rader C, Steinberger P, Fuller R, Barbas CF 3rd., J Immunol Methods. 2000 Aug. 28; 242(1-2):159-81) and cloned into the pComb3X vector (kind gift from the Barbas lab, San Diego (The Skaggs Institute for Chemical Biology and the Departments of Molecular Biology and Chemistry, The Scripps Research Institute, 10550 North Torrey Pines Rd., La Jolla, Calif. 92037) in a VL-VH scFv format, with a 18 amino acid flexible linker joining both variable domains and a HA tag for detection and antibody capture. Cloned scFv genes were electroporated into *E. coli* XL-1 blue (Strategene, La Jolla, Calif. 92037) cells generating an antibody library of approximately $3 \times 10^7$ clones. The scFv fragments were packaged on the surface of M13KO7 phage and subjected to four rounds of panning against microtitre plate wells (Maxisorp, Nunc) coated with 10, 5, 1 and 1 □g/ml target antigen, respectively. After panning, eluted phage were re-infected into *E. coli* TOP10F' (Invitrogen) cells and single colonies selected for monoclonal ELISA in sterile 96 well culture plates. ScFv production was induced by the addition of 1 mM IPTG overnight at 30° C. prior to screening for binding to antigen in solution (competitive ELISA).

Example IIIa: Method:

For a direct method comparison between antibodies grown in pre-coated ELISA plate wells and antibodies grown in culture and later added to antigen coated microtiter plate wells, two scFv fragments and one scFv clone rescued on the surface of M13KO7 helper phage were inoculated into a 50 mL sterile tubes containing 10 mL of SB broth supplemented with 50 μg/mL carbenicillin and 10 μg/mL tetracycline. These were grown while shaking at 37° C. until the O.D.600 reached 0.8, at which time IPTG was added to a final concentration of 1 mM. Immediately after induction, 200 μL of culture was added to an antigen-coated ELISA plate (pre-coated with 1 μg/mL PSA, 1 μg/mL HFG-BTG or PBS and blocked with 3% (w/v) BSA) wells and both the ELISA plate and 50 mL culture flask incubated overnight together at 30° C. with constant agitation. The following day, 200 μL of 'off-plate' samples (samples cultured in 50 mL tubes) were also added directly to the ELISA plate. All samples were incubated at 37° C. for a further 1 hour and detected with anti-HA HRP antibody and TMB substrate.

Method: Example IIIb: Analysis of *E. Coli* Cells Harbouring scFv Antibody Genes to C-Reactive Protein (CRP) and Cardiac Troponin I (cTnI) Cultured in a 10 μm Diameter Micropore Array Antibody cultures were prepared by transferring 10 μL from −80° C. glycerol stocks of *E. coli* cells containing pComb3x plasmids encoding anti-CRP or anti-cTnI scFv antibody genes to 990 μL auto induction media. The cultures were mixed by inversion and 5 μL of each culture added to two regions on separate 10 μm diameter micropore arrays. Media was also added as a negative control. The 10 μm diameter micropore array was subsequently reversibly attached to a PDMS slab coated with cognate antigen on one region and blocking buffer only on the other region so that each antibody culture was in contact with antigen and blocking only as an additional negative control. After incubation at 37° C. overnight, bound antibody was detected with anti-HA Cy5-labelled antibody using a PerkinElmer microarray scanner.

Example IV

Cell Removal from the Micro-Array Testbed

This example demonstrates that cells cultured in the 10 μm diameter micro-array testbed for 24 hrs at 37° C. can be extracted by applying air pressure to the testbed and recovered on agar plates. Growth of the cells on agar plates following further incubation at 37° C. demonstrates cell viability.

Figure 13:
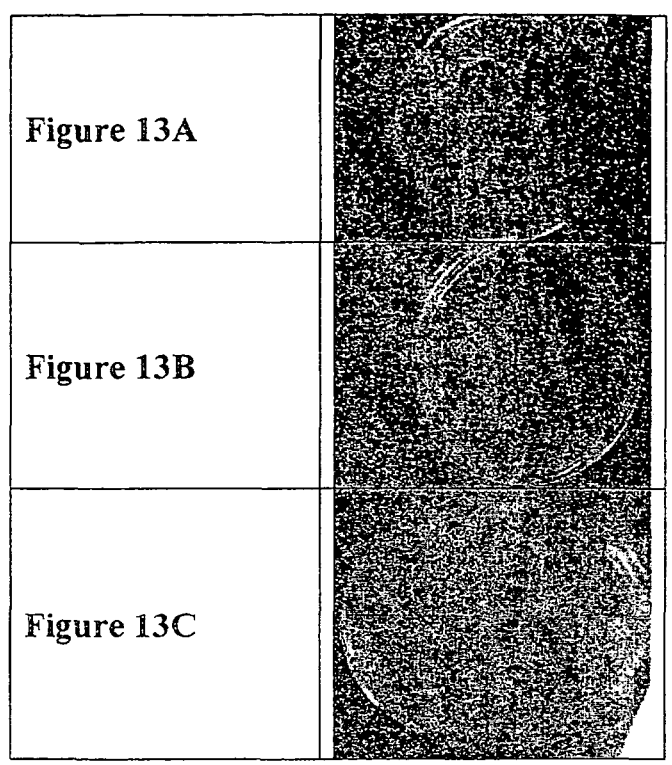
FIG. 13 shows capture and growth of E. coli cells on agar plates after recovery from the micro-array testbed.

The experiment was performed to confirm cell growth and viability in the array after 24 hours incubation at 37° C. *E. coli* cells harbouring the pET28b plasmid encoding the GFP gene fused to a cTnI peptide were grown to an $OD_{600}$~0.4 at which time they were induced for 1 hour to allow GFP expression. The cells were diluted in media to 1/10, 1/100, 1/1000 and 1/10000 and 2 μL of each dilution (including the neat culture and media only as a negative control) added to a section of the array. The array was sandwiched between two pieces of PDMS (not degassed) and left at 37° C. for 24 hours. Meanwhile, 100 µL/well of the each dilution was also added to a black Nunc plate and the fluorescence measured. The plate was left overnight at 37° C. shaking and the fluorescence measured the following day to determine cell growth. See FIG. 12. Cells from the open perforated glass array were recovered onto agar plate by blowing the liquid out using a pipette tip linked to compressed air tube. The plates were incubated overnight to confirm that the cells in the array were still viable after 24 hours. See FIG. 13.

Conclusion: The contents of a micropore can be expelled by application of a gas source. In addition, this demonstrates that, when the cells are expelled onto agar, the cells are still viable.

Example V

Precision Liquid Removal from the Micro-Array Testbed

This example demonstrates that small volumes of liquid can be removed from precise positions in the micro-array testbed (10 µm diameter) by placing a cover over the array which contains a small (100 µm diameter) hole.

A black box (approximately 1 cm by 2 cm) was printed on to a Xerox transparent sheet (Type A, P/N 003896019) using a standard laser printer. The box was cut out and placed into the focus of a high power laser, which melted a circular 100 µm diameter hole in the sheet. See FIG. 17. The pores in the micro-array testbed were filled with 3 µL of red food colorant to aid visualization. The section of printed black transparent sheet with the 100 µm hole was placed over the food colorant filled testbed array and clamped in position. A tube (approximately 2-3 mm in diameter) connected to a compressed air source was placed over the hole and air pressure applied. The air was forced to flow through the hole and r the food colorant was removed (expelled) from the testbed array. Food colorant was removed in a circular pattern to a diameter of 300 µm, 3 times the size of the hole used. See FIG. 18.

Example VI

Antibody Secretion from B cells

B cells (B lymphocyte cell line, ATCC No: TIB-196 (Designation U266, supplier: LGC Standards, Middlesex, UK) (about $1 \times 10^4$ cells/mL) were added to a 40 µm pore diameter array, cultured for 4 days and expressed antibody analysed by sandwich ELISA. The bright dots represent the antibody patterned PDMS from single pores that had B cells expressing antibody. The spots are 40 µm in diameter. See FIG. 23.

Figure 23:
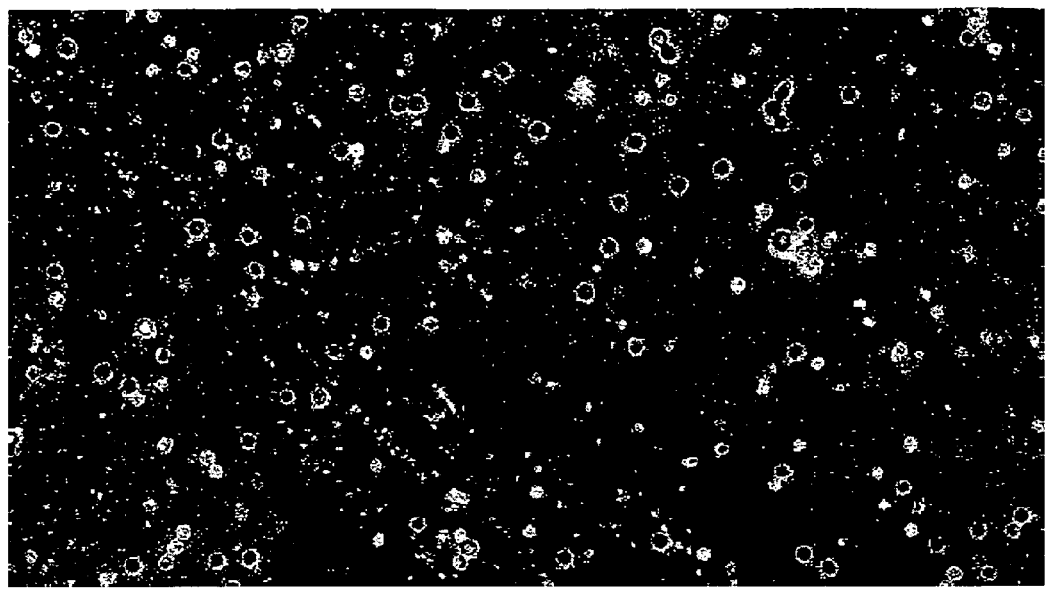
FIG. 23 demonstrates that specific B cell antibody response can be detected when cultured in the array and individual positive pores can be visualized.

FIG. 23 demonstrates that specific B cell antibody response can be detected when cultured in the array and individual positive pores can be visualized. The background represents those pores that had no B cells expressing antibody or did not contain any B cells at all. Without being bound by theory, it is thought that, when a B cell suspension of about $1 \times 10^4$ cells/mL is distributed across micropores having an internal diameter of 40 µm and a volume of 1.2 mL, there may about 1 cell in approximately every 84 micropores.

Analysis of B cell culture grown and screened in the micropore filter array. B cells were added to a 40 µm pore diameter array, cultured for 4 days and expressed antibody analysed by sandwich ELISA. See FIG. 24.

Figure 24:
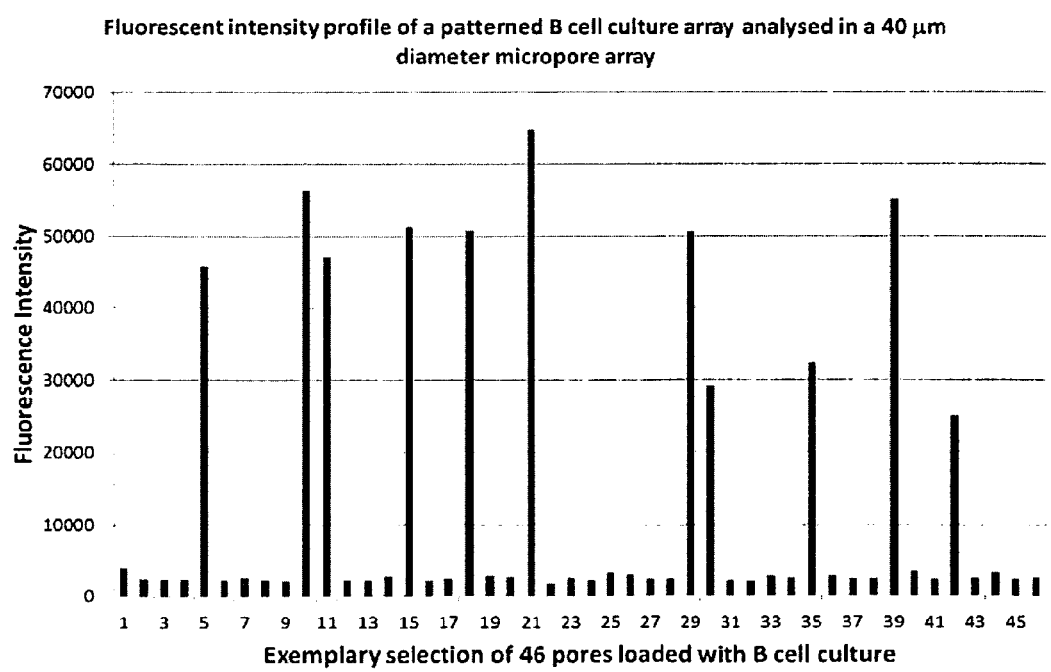
FIG. 24 illustrates that specific B cell antibody response can be detected when cultured in the array FIG. 25 demonstrates that specific recombinant antibody response can be detected when cultured in the array.

The fluorescence of individual B cells pores was compared to that of pores with no cells or pores with B cells not expressing antibody. FIG. 24 illustrates that specific B cell antibody response can be detected when cultured in the array.

Sandwich ELISA for the detection of human IgE secreted from U266 B cell line: Coated 2 µg/mL Mab 107 (Mabtech code 3810-3-250) (capture antibody) Detected with 0.33 µg/mL Mab 182-biotin antibody diluted with PBS with 0.5% (w/v) BSA for 1 hour followed by the addition of streptavidin-dylight 650 (Fisher Cat. No. 84547) diluted in PBS with 0.5% (w/v) BSA to a final concentration of 2 µg/mL.

Example VII

Non-Degassed Driven Loading and Patterning of the Micropore Array

Figure 26:
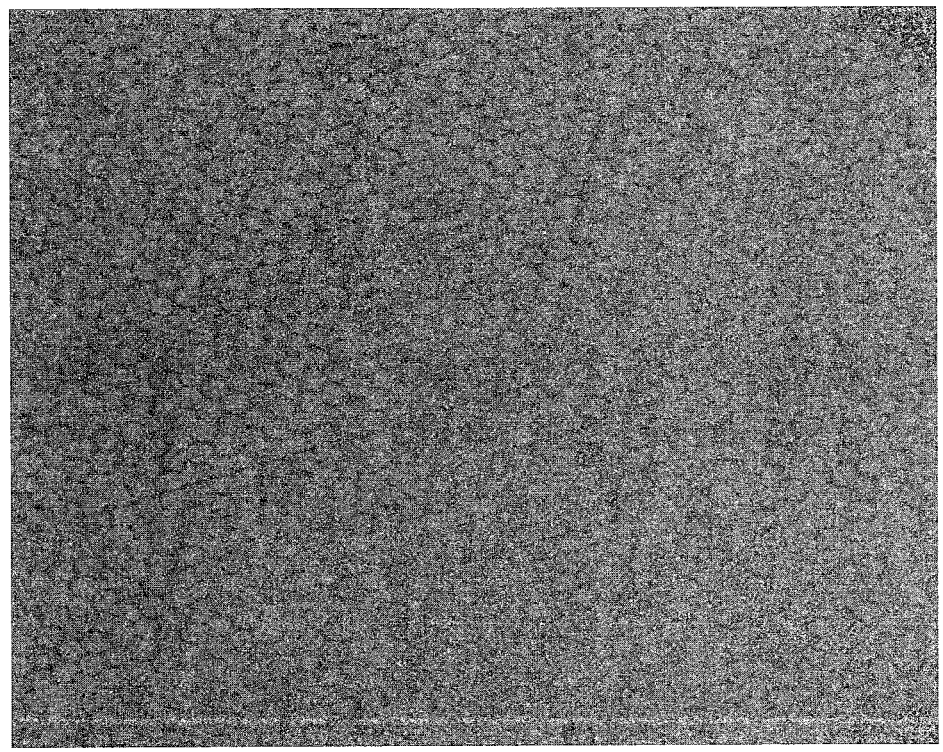
FIG. 26 demonstrates non-degassed driven loading and patterning of the micropore array. This Figure is to show that even patterning can be achieved without leckage to air blockage, without degas driven flow.

Goat anti-human IgG Cy5 antibody was loaded in to the capillary array (10 µm diameter pores) and sealed with unmodified PDMS that was not degassed. A clear array pattern was observed indicating that degas driven loading of the solid substrate (for example, PDMS) is not critical for the device, kit and method of the present invention. See FIG. 26*a*.

Figure 26B:
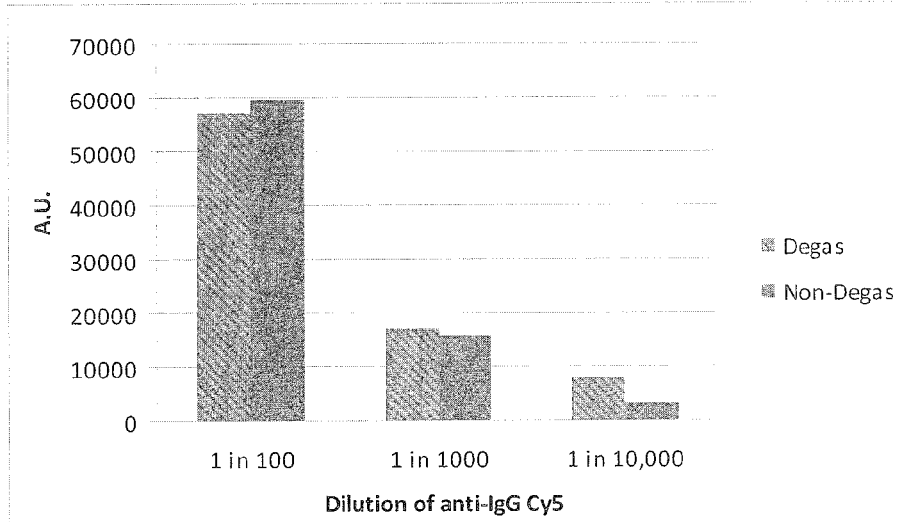
FIG. 26B demonstrates a comparison of immunoassay performance from degassed and non-degassed driven loading of the micropore array. This Figure shows that the immunoassay performance in the array is not affected by whether the solid substrate (such as PDMS), if present, is degassed or non-degassed.

This experiment shows that substantially even patterning using a dye labeled protein can be achieved without degassing. FIG. 26*b* shows a direct comparison in assay between degassed and non-degassed loading. It will be appreciated that the choice of degassing v non-degassing the solid substrate is independent of choice of binding partners, for example, the antibody-antigen pair—in either case, there must be liquid contact with the solid substrate (for example, PDMS) surface.

A direct comparison of a direct binding immunoassay using degassed and non-degassed antigen coated PDMS was also performed. Two PDMS slabs were coated with 5 µg/mL of human IgG and blocked with 3% (w/v) BSA. Goat anti-human IgG Cy5-labelled antibody diluted to 50, 5 and 0.5 µg/mL in PBS was added to different regions on both arrays and incubated for 1 hour at 37° C. Bound antibody was detection using a PerkinElmer microarray scanner. See, FIG. 26*b*.

Example VIII

Determination of Enhanced Surface Coating with APTES Coated PDMS

Direct binding assay. Goat anti-human IgG Cy5 antibody was added to human IgG coated PDMS that had been modified with APTES treatment (left picture) or unmodified (right picture). Both signal and uniformity is enhanced with APTES treatment. See, FIG. 27. APTES (Sigma, A3648-100 mLs)

3% (v/v) APTES was prepared in 98% ethanol

PDMS slab was exposed to $O_2$ plasma (a procedure to clean or modify the surface of materials, such as PDMS, by using an energetic plasma created from gaseous species, such as argon and oxygen, or gaseous mixtures such as air and hydrogen/nitrogen for 6 minutes before being submerged in 3% APTES solution for 1 hour at 25° C.

Slab washed with ethanol

Slab dried by baking at 60° C. for 2 hours before being coated with antigen of interest.

Example X

Single Pore Removal Setup and Procedure

Using an in house built high precision dual XY-stage and laser setup, cells residing in target pores may be harvested into wells of a 384 well plate by laser ablation of array sealant and subsequent liquid removal by application of air pressure. See FIGS. 28a, 28b and 28c.

Aim: To show that *E. coli* cells can be retrieved from single micro-pores and that the cells are viable once recovered in growth media.

Figure 28A:
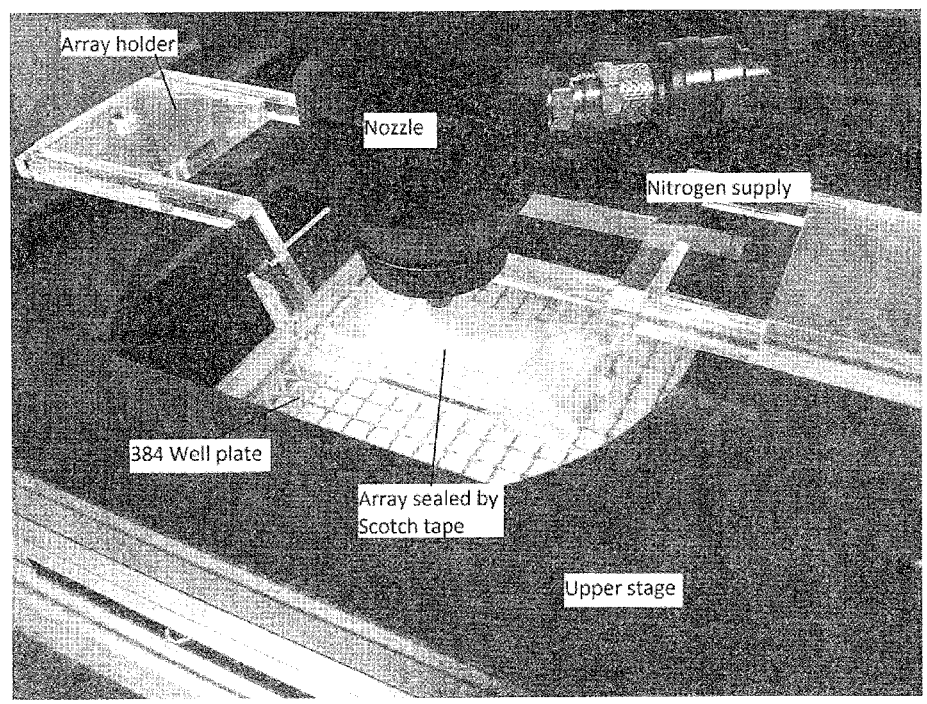
FIGS. 28A and 28B demonstrate that cells residing in target pores may be harvested.
Figure 28B:
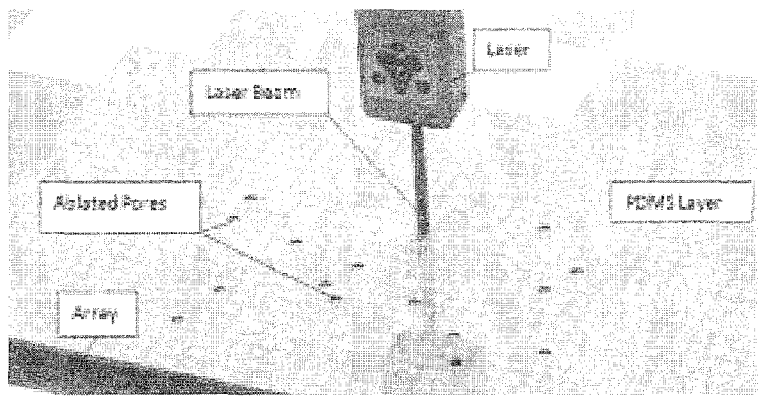

*E. coli* cells containing a pET26b plasmid and enhanced GFP gene were cultured overnight in SB (Super Broth, contents/liter: 35 g tryptone, 20 g yeast extract, 5 g NaCl) growth medium containing 25 ng/mL kanamycin and 1% (w/v) glucose. The next day, 60 µL of SB containing 25 µg/mL kanamycin was added to wells of a 384 well plate and 1 µL of a 1/100 dilution of overnight cells added to one well of the 384 well as a positive control. The plate was added to the lower XY stage as shown in FIG. 28a. Next, 254, of the overnight *E. coli* culture was added to a 40 µm diameter micropore array. The array was sealed with scotch tape (~55 µm in thickness), loaded onto the array holder and the holder subsequently attached to the upper XY stage. The laser/air nozzle assembly was lowered to 2 mm above the array while the bottom surface of the array sat less than 0.5 mm above the well plate. Two single holes over above a cultured filled pore were ablated in situ along with cell extraction using nitrogen (with a power setting of 8% from a 25 W laser for approximately 0.5 seconds). The pore contents were extracted into a media filled well of the 384 plate underneath the area and the XY stage moved to capture cells in different wells of the 384 well plate as needed. One well with media only was used as a negative control whereby no cells were added to that well. The 384 well plate was incubated at 37° C. for 18 hours and then the O.D.600 measured using a Tecan Safire2 microtiter plate reader. The absorbance values of each well are shown in FIG. 18b.

Results

Figure 18B:
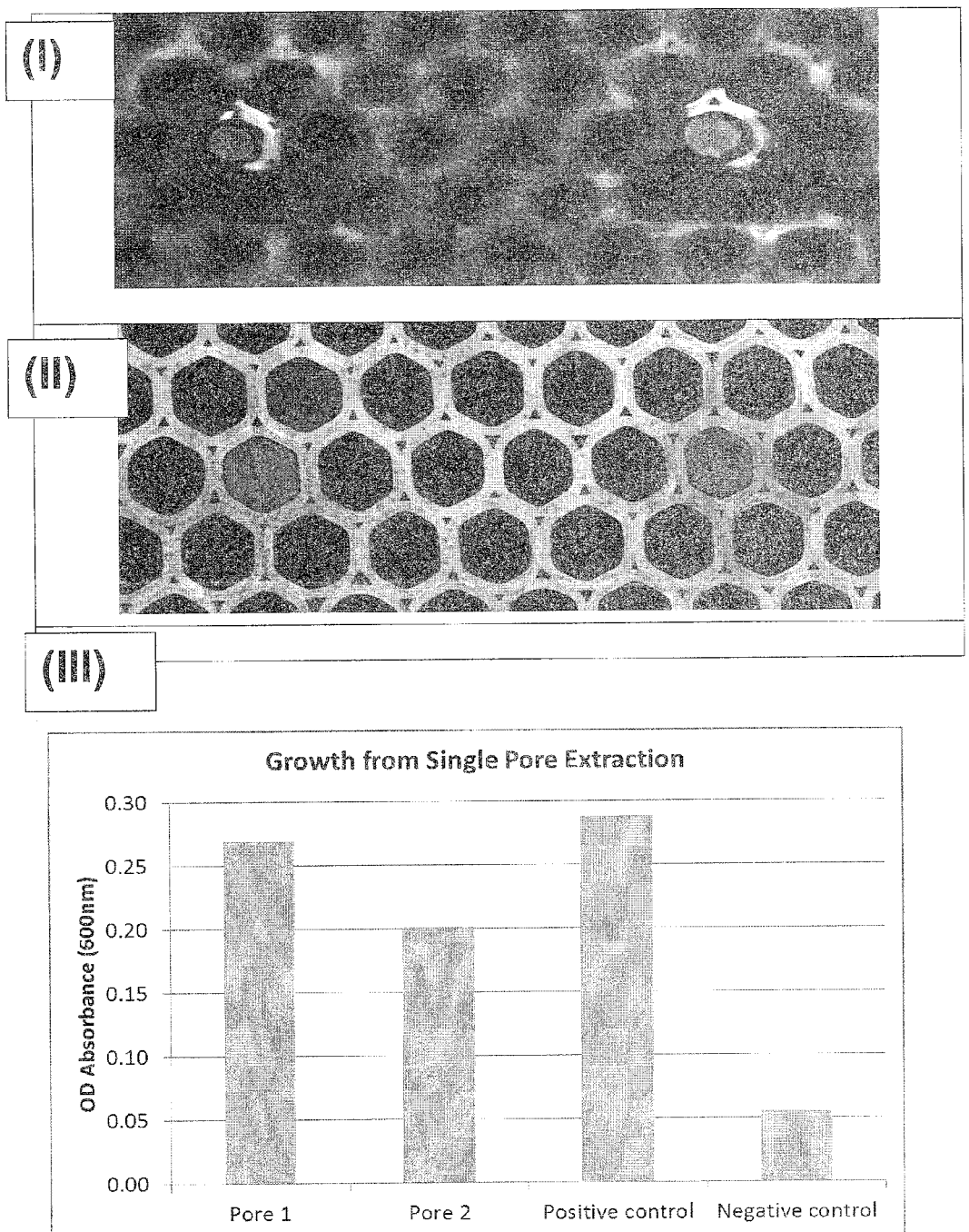
FIG. 18B presents exemplary data showing single pore recovery of viable E. coli cells from a 40 μm diameter micropore array.

FIG. 18b: Single pore recovery of viable *E. coli* cells from a 40 µm diameter micropore array. Panel (I) shows two ~40 µm holes ablated in scotch tape (3M Company, ~55 µm in thickness) which is sealed to a 40 µm diameter micro-pore array (supplied by Incom USA). The contents of each micropore (cells) are instantaneously removed once the hole is ablated due to the nitrogen flow from the laser nozzle. Panel (II) shows the same micro-pore array with the scotch tape removed, revealing two empty pores at the precise location of the ablated holes. Panel (III) shows a graph representing cell viability after being recovered from a single pore in to a single well of a 384 well microtiter plate containing 60 µL of growth media. Pore 1 is the left-hand empty pore of panel (II) and pore 2 is the rigfht-hand empty pore of panel (II). The positive control sample represents a well containing 60 µL of media spiked with 1 µL of overnight *E. coli* culture and the negative control represents 60 µL of media only.

Conclusion: Using the cell recovery setup of the present invention, *E. coli* cells from a single pore of a micropore array can be recovered into a well of a 384 well plate containing growth media and cultured to expand the cell population.

Example XI

In Solution Assays—Demonstration of GFP Reassembly in the Array

Aim: The aim of this experiment was to demonstrate an in-solution binding assay in the array, using the GFP reassembly vectors described by Magliery et al. (J Am Chem. Soc. 2005 Jan. 12; 127(1):146-57. "Detecting protein-protein interactions with a green fluorescent protein fragment reassembly trap: scope and mechanism". Magliery T J, Wilson C G, Pan W, Mishler D, Ghosh I, Hamilton A D, Regan L). This system uses the reassembly of the dissected fragments of GFP to identify specific protein-protein interactions. Vectors were obtained from the authors and the positive control vectors were used for the proof of concept experiments, described herein.

Details of System

Vector 1: pET11a-Z-NGFP(NZ) contains the N-terminal region of GFP fused to a leucine zipper peptide (anti-parallel to that on Vector 2). It is ampicillin resistant and expression is induced by IPTG addition (Lac I operon).

Vector 2: pMRBAD-Z-CGFP(CZ) encodes the C-terminal of GFP fused to a different leucine zipper peptide (anti-parallel to that on Vector 1). It is kanamycin resistant and expression is induced by Arabinose addition (AraC operon).

Method:

Plasmids were transformed into BL21 (DE3) *E. coli* separately. A sequential transformation was then carried out, meaning that the cells transformed with one plasmid were made competent and then transformed with the second plasmid. This meant that both plasmids were contained within the same cell, denoted in this report as "in vivo".

Positive transformants were identified by growth on screening media which contains 1 µM IPTG, 0.2% Arabinose, 35 µg/mL Kanamycin, 100 µg/mL Carbenicillin. This was carried out on solid media and also in solution (in plate and on array). Cultures were grown at 37° C. overnight, followed by 2-3 days at 15-25° C.

In addition to 'in vivo' screening, cells containing single plasmids were mixed and co-expressed, denoted in this report as 'in vitro'. This was done in the absence of antibiotics, as growth would have been inhibited. A 10 µL aliquot of each of the following, in appropriate expression media, was added to the array and incubated for 5 days at 25° C.
(a) CZ only
(b) NZ only
(c) CZ+NZ 'in vivo'(i.e. in the same cell)
(d) CZ+NZ 'in vitro'(i.e. mixed culture)

Results:

'In Vivo' Screening

Following 2.5 days of expression on screening media, the level of fluorescence was observed in a transilluminator box, wavelength ~365 nm.

Figure 29:
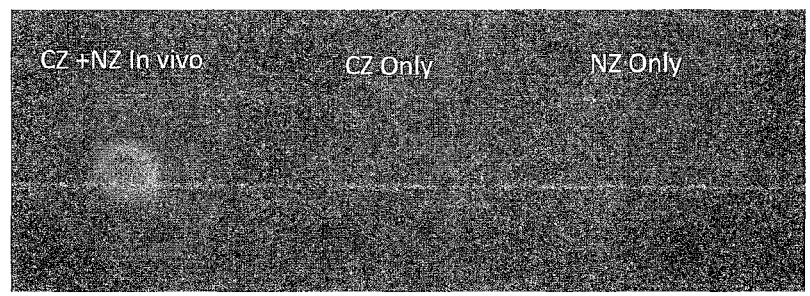
FIG. 29 presents exemplary data demonstrating of reassembly of GFP 'in vivo' in liquid media. Cells have been pelleted by centrifugation at 4000 rpm for 10 mins and the supernatant removed.

FIG. 29: Demonstration of reassembly of GFP 'in vivo' in liquid media. Cells have been pelleted by centrifugation at 4000 rpm for 10 mins and the supernatant removed.

'In Vitro' Screening—on Array

Figure 30:
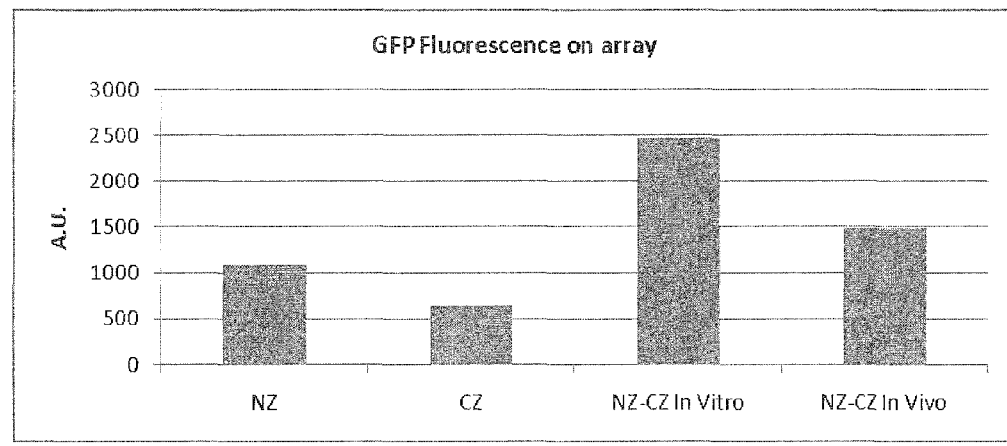
FIG. 30 presents exemplary data showing a graphical representation of the fluorescent intensity values obtained from microarray pore array with E. coli cultures harbouring split GFP fragments using a fluorescent microscope.

The level of fluorescence was compared in three ways:
1. Visualisation using a transilluminator (not illustrated herein).
2. Visualisation using a microscope (not illustrated herein)
3. Measurement of the fluorescence intensity from images using histogram function in Image J, as demonstrated in FIG. 30. FIG. 30: Graphical representation of the fluorescent intensity values obtained from microarray pore array with *E. coli* cultures harbouring split GFP fragments using a fluorescent microscope.

Example XII

In Solution Assays—FRET Demonstration

Experiment: Demonstration of in solution DNA binding assay in the micropore array using FRET.

Aim: The aim of this experiment was to demonstrate an in-solution binding assay in the array, using the FRET detection based on the reassembly two complimentary DNA probes labelled with Cy5 and Cy5.5. Once DNA hybridisation occurs, the Cy5 and Cy5.5 dyes are brought in close proximity with each other so that fluorescence energy transfer can occur between the Cy5 donor and Cy5.5 acceptor. Due to the transfer of energy, the intensity of emitted light from Cy5 is reduced in the presence of bind Cy5.5 held in close proximity by the bound DNA.

Details of System:

```
DNA probe 1: 5'-Cy5-TTACggTTggTggCgTCTCTg

DNA probe 2: 5'-AATgCCAAC CAC CgCAgA gAC-Cy5.5
```

Both DNA probes were purchased from TIB MOLBIOL, Berlin, Germany.

Method:

In order to measure the energy transfer between the donor and acceptor in solution, $1\times10^{-8}$M solutions of the donor labeled oligonucleotide was mixed 1:1 (v/v) with hybridisation buffer alone or with hybridisation buffer containing $1\times10^{-8}$M acceptor labelled complementary oligonucleotide. Acceptor labelled oligonucleotide was also mixed 1:1(v/v) with buffer results in three final solutions containing donor alone, donor and acceptor mixed and acceptor alone. 100 µL of each solution was immediately added to wells of a black Nunc 96 well plate and 2 µL of each solution added to different regions of a 40 nm diameter micropore arrays. Both array and micotitre were incubated at 37° C. for 30 mins before analysis. The micotitre plate was analysed using a TecanStaphire II (Ex 610 nm and em 650-750 scan) fluorescent plate reader and the array analysed using a fluorescent microscope with Cy5 filter.

Figure 31:
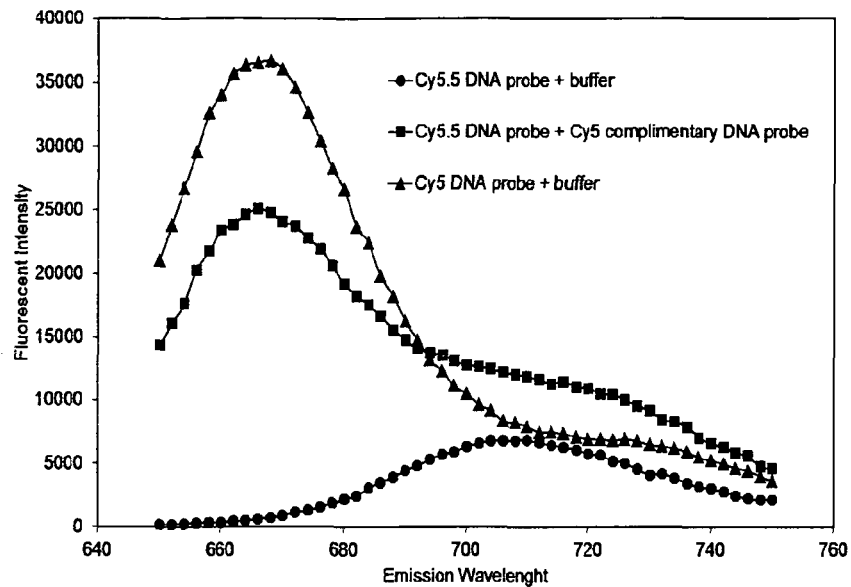
FIG. 31 presents exemplary data showing an emission scan of the DNA-FRET due to binding of complimentary 21 bp DNA probes labelled with Cy5 (donor) and Cy5.5 (acceptor).
Figure 32:
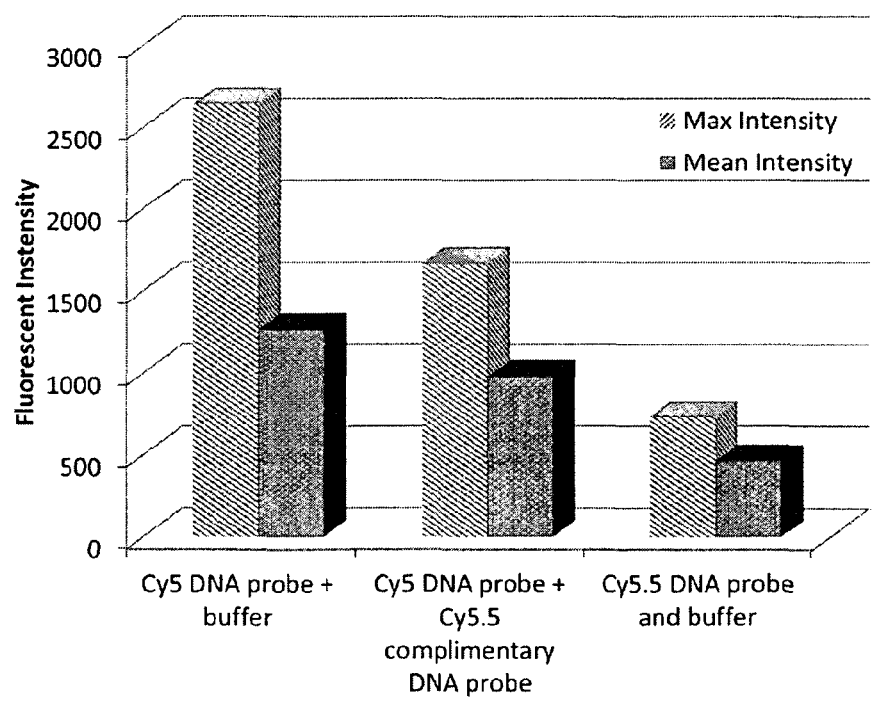
FIG. 32 presents exemplary data showing mean and maximum emission intensities of the DNA-FRET due to binding of complimentary 21 bp DNA probes labelled with Cy5 (donor) and Cy5.5 (acceptor) in a 40 μm diameter micropore array.

Results:

DNA-FRET was successfully demonstrated using fluorescence intensity measurements from spectral analysis in a microtitre plate (FIG. 31) and in a 40 µm diameter micropore array (FIG. 32). Binding of the two complementary DNA probes is detected by a clear decrease in Cy5 emission due fluorescent energy transfer with the Cy5.5 acceptor.

The invention claimed is:

1. A method for identifying a sub-population of at least one biological cell from a heterogeneous population of biological cells, said method comprising:
   a) contacting the heterogeneous population of biological cells with a solid substrate attached to at least one binding partner such that a sub-population comprising at least one of said biological cells settles into at least one micro-pores of an array of micro-pores, the array comprising a plurality of longitudinally fused fibers each having opposed openings and an internal diameter in a range of between approximately 1.0 micrometers and 500 micrometers, the fibers being reversibly attached to the solid substrate;
   b) incubating said array under conditions to promote the secretion of molecules from said biological cells;
   c) detecting desired secreted molecules in association with said at least one binding partner on the solid substrate; and
   d) sealing a polymeric film to the longitudinally fused fibers and positioning at least one hole in the film over at least one longitudinally fused fiber containing the sub-population of at least one cell secreting desired molecules, and removing the longitudinally fused fiber array from the solid substrate, to thereby identify said sub-population of at least one cell.

2. The method of claim 1, said method further comprising providing a pressure source or electrolytic expulsion source configured proximal to at least one of said openings.

3. The method of claim 2, wherein said pressure source is a source of positive or negative pressure.

4. The method of claim 1, said method further comprising collecting said subpopulation of at least one biological cell from said at least one longitudinally fused fiber.

5. The method of claim 1, wherein said heterogeneous population of biological cells releases at least one biological compound having affinity for said at least one binding partner.

6. The method of claim 1, wherein said at least one binding partner comprises at least one selected from the group consisting of antigens, antibodies, proteins, peptides, nucleic acids, deoxyribonucleic acids, ribonucleic acids, lipids, and carbohydrates.

SEQUENCE LISTING

<160> NUMBER OF SEQ ID NOS: 2

<210> SEQ ID NO 1
<211> LENGTH: 21
<212> TYPE: DNA
<213> ORGANISM: Artificial sequence
<220> FEATURE:
<223> OTHER INFORMATION: synthetic DNA probe

<400> SEQUENCE: 1
ttacggttgg tggcgtctct g                                    21

<210> SEQ ID NO 2
<211> LENGTH: 21
<212> TYPE: DNA
<213> ORGANISM: Artificial sequence
<220> FEATURE:
<223> OTHER INFORMATION: synthetic DNA probe

<400> SEQUENCE: 2
aatgccaacc accgcagaga c                                    21

7. The method of claim 1, wherein said detecting comprises a labeled reagent having affinity for a complex formed between said at least one binding partner and said secreted molecules.

8. The method of claim 4, wherein said collecting comprises cultivating said sub-population of at least one biological cell.

9. The method of claim 1, wherein said array comprises between approximately 300 to 1,150,000 of said fused fibers per cm$^2$ of said array.

10. The method of claim 1, wherein said plurality of longitudinally fused fibers ranges between approximately 300,000 and 5,000,000,000 longitudinally fused fibers.

11. The method of claim 1, wherein the solid support is degassed.

12. The method of claim 1, wherein the heterogenous population of biological cells is in a solution or suspension when contacting the solid support.

\* \* \* \* \*